(12) United States Patent
Vadivelu

(10) Patent No.: US 11,938,143 B2
(45) Date of Patent: Mar. 26, 2024

(54) COMPOSITIONS COMPRISING 2'-DEOXYCYTIDINE ANALOGS AND USE THEREOF FOR THE TREATMENT OF SICKLE CELL DISEASE, THALASSEMIA, AND CANCERS

(71) Applicant: AkiraBio, Inc., Wellesley, MA (US)

(72) Inventor: Santhosh Vadivelu, Wellesley, MA (US)

(73) Assignee: AkiraBio, Inc., Wellesley, MA (US)

( * ) Notice: Subject to any disclaimer, the term of this patent is extended or adjusted under 35 U.S.C. 154(b) by 0 days.

(21) Appl. No.: 17/969,192

(22) Filed: Oct. 19, 2022

(65) Prior Publication Data

US 2023/0122664 A1 Apr. 20, 2023

Related U.S. Application Data

(60) Provisional application No. 63/257,541, filed on Oct. 19, 2021.

(51) Int. Cl.
| | |
|---|---|
| *A61K 31/7068* | (2006.01) |
| *A61K 9/20* | (2006.01) |
| *A61K 9/48* | (2006.01) |
| *A61K 31/53* | (2006.01) |
| *A61K 35/28* | (2015.01) |
| *A61P 7/00* | (2006.01) |

(52) U.S. Cl.
CPC ........ *A61K 31/7068* (2013.01); *A61K 9/2009* (2013.01); *A61K 9/2013* (2013.01); *A61K 9/4825* (2013.01); *A61K 9/485* (2013.01); *A61K 9/4858* (2013.01); *A61K 31/53* (2013.01); *A61K 35/28* (2013.01); *A61P 7/00* (2018.01)

(58) Field of Classification Search
CPC .. A61K 31/7068; A61K 31/53; A61K 9/2207; A61K 9/2013; A61K 9/4825; A61K 9/485; A61K 9/4858; A61K 35/28; A61P 7/08
USPC .......................................................... 514/49
See application file for complete search history.

(56) References Cited

U.S. PATENT DOCUMENTS

| | | | |
|---|---|---|---|
| 4,822,821 | A | 4/1989 | Perrine |
| 4,997,815 | A | 3/1991 | Perrine et al. |
| 5,025,029 | A | 6/1991 | Perrine |
| 5,439,939 | A | 8/1995 | Perrine |
| 5,591,722 | A | 1/1997 | Montgomery et al. |
| RE36,080 | E | 2/1999 | Perrine |
| 6,011,000 | A | 1/2000 | Perrine et al. |
| 6,136,791 | A | 10/2000 | Nyce |
| 6,231,880 | B1 | 5/2001 | Perrine |
| 7,910,624 | B1 | 3/2011 | Perrine et al. |
| 7,927,785 | B2 | 4/2011 | Milhem et al. |
| 8,329,666 | B2 | 12/2012 | Belyakov et al. |
| 8,618,068 | B2 | 12/2013 | Perrine et al. |
| 8,618,075 | B2 | 12/2013 | Hamilton et al. |
| 8,759,378 | B2 | 6/2014 | Perrine et al. |
| 8,846,628 | B2 | 9/2014 | Etter et al. |
| 9,018,176 | B2 | 4/2015 | Perrine et al. |
| 9,095,565 | B2 | 8/2015 | Perrine |
| 9,895,391 | B2 | 2/2018 | DeSimone et al. |
| 10,517,884 | B2 | 12/2019 | DeSimone et al. |
| 11,376,270 | B2 | 7/2022 | Saunthararajah et al. |
| 2007/0117776 | A1 | 5/2007 | Lyons |
| 2011/0218170 | A1* | 9/2011 | Thottassery ....... A61K 31/7068 514/49 |
| 2012/0225836 | A1 | 9/2012 | DeSimone et al. |
| 2015/0231077 | A1 | 8/2015 | Egusa et al. |
| 2017/0253589 | A1 | 9/2017 | Saunthararajah et al. |
| 2018/0325932 | A1 | 11/2018 | DeSimone et al. |
| 2019/0194166 | A1 | 6/2019 | Adams et al. |
| 2022/0031671 | A1 | 2/2022 | Ericsson et al. |
| 2022/0152075 | A1 | 5/2022 | Saunthararajah et al. |
| 2022/0226355 | A1 | 7/2022 | Saunthararajah et al. |
| 2023/0055298 | A1 | 2/2023 | Vadivelu |
| 2023/0122664 | A1 | 4/2023 | Vadivelu |

(Continued)

FOREIGN PATENT DOCUMENTS

| | | | | |
|---|---|---|---|---|
| EP | 0421777 | A1 | 4/1991 | |
| EP | 1123111 | B1 * | 9/2004 | ......... C12N 15/1137 |
| EP | 3191104 | A1 | 7/2017 | |

(Continued)

OTHER PUBLICATIONS

The Merck Manual , 1992, pp. 1263, 1266-1269.*
EMSWorld, Aug. 2005, pp. 1-8.*
Yoshida et al, Chem. Pharm. Bull. 1982, 30(3), 1018-1023.*
Ho et al, Cancer Research, 1980, 40, 2441-2446.*
Senkevitch et al, Cytokine, 2017, 98, 33-41.*
Roth et al, Journal of the National Cancer Institute, 1997, 89(1), 21-39.*
Thottassery et al, Cancer Chemother Pharmacol, 2014, 74, 291-302.*
Atweh et al, Current Opinion in Hematology, 2001, 8, 123-130.*
Jacob et al, Indian Journal of Pharmaceutical Sciences, 2007, 69(5), 633-639.*

(Continued)

*Primary Examiner* — Ganapathy Krishnan
(74) *Attorney, Agent, or Firm* — Wolf, Greenfield & Sacks, P.C.

(57) ABSTRACT

In one aspect, the disclosure relates to pharmaceutical compositions comprising 2'-deoxycytidine analogs, oral and other dosage formulations containing the same, and methods of making the same. In another aspect, the disclosure relates to methods of treating hematological disorders and diseases associated with abnormal cell proliferation using the same. In a still further aspect, the disclosure relates to kits comprising 2'-deoxycytidine analogs useful for treating hematological disorders and diseases associated with abnormal cell proliferation. In still another aspect, the disclosure relates to methods for increasing fetal hemoglobin levels in a subject. This abstract is intended as a scanning tool for purposes of searching in the particular art and is not intended to be limiting of the present disclosure.

20 Claims, 12 Drawing Sheets

(56) References Cited

U.S. PATENT DOCUMENTS

2023/0123277 A1    4/2023    Vadivelu et al.

FOREIGN PATENT DOCUMENTS

| EP | 2766041 | B1 | 12/2018 |
|---|---|---|---|
| WO | WO 2008/028193 | A2 | 3/2008 |
| WO | WO 2009/052287 | A1 | 4/2009 |
| WO | WO 2017/096357 | A1 | 6/2017 |
| WO | WO 2019/152459 | A1 | 8/2019 |
| WO | WO 2021/211890 | A1 | 10/2021 |
| WO | WO 2021/216936 | A1 | 10/2021 |

OTHER PUBLICATIONS

U.S. Appl. No. 17/918,748, filed Oct. 13, 2022, Vadivelu.
U.S. Appl. No. 17/966,388, filed Oct. 14, 2022, Vadivelu et al.
PCT/US2022/047146, Jan. 16, 2023, International Search Report and Written Opinion.
PCT/US2021/027548, Jul. 14, 2021, International Search Report and Written Opinion.
PCT/US2021/027548, Oct. 27, 2022, International Preliminary Report on Patentablility.
International Preliminary Report on Patentability for Application No. PCT/US2021/027548, dated Oct. 27, 2022.
International Search Report and Written Opinion for Application No. PCT/US2022/047146, dated Jan. 16, 2023.
International Search Report and Written Opinion for Application No. PCT/US2021/027548, dated Jun. 14, 2021.
Atweh et al., Pharmacologic induction of fetal hemoglobin: raising the therapeutic bar in sickle cell disease. Current opinion in hematology. Mar. 1, 2001;8(2):123-30. doi:10.1097/00062752-200103000-00010.
Belcher et al., Haptoglobin and hemopexin inhibit vaso-occlusion and inflammation in murine sickle cell disease: Role of heme oxygenase-1 induction. PLoS One. Apr. 25, 2018;13(4):e0196455(1-20). doi: 10.1371/journal.pone.0196455.
Cesta M.F., Normal structure, function, and histology of the spleen. Toxicol Pathol. 2006;34(5):455-65. doi: 10.1080/01926230600867743.
Charache et al., Investigators of the Multicenter Study of Hydroxyurea in Sickle Cell Anemia. Effect of hydroxyurea on the frequency of painful crises in sickle cell anemia. New England Journal of Medicine. May 18, 1995;332(20):1317-22. doi:10.1056/NEJM199505183322001.
Covey et al., Differences in DNA damage produced by incorporation of 5-aza-2'-deoxycytidine or 5, 6-dihydro-5-azacytidine into DNA of mammalian cells. Cancer Research. Nov. 1986;46(11):5511-7.
Cui et al.. Nuclear receptors TR2 and TR4 recruit multiple epigenetic transcriptional corepressors that associate specifically with the embryonic β-type globin promoters in differentiated adult erythroid cells. Molecular and cellular biology. Aug. 15, 2011;31(16):3298-311. doi:10.1128/MCB.05310-11.
Desimone et al., Maintenance of elevated fetal hemoglobin levels by decitabine during dose interval treatment of sickle cell anemia. Blood, The Journal of the American Society of Hematology. Jun. 1, 2002;99(11):3905-8. doi:10.1182/blood.v99.11.3905.
Estepp et al., Safety and efficacy of voxelotor in pediatric patients with sickle cell disease aged 4 to 11 years. Pediatr Blood Cancer. Aug. 2022;69(8):e29716(1-10). doi: 10.1002/pbc.29716. Epub Apr. 21, 2022.
Ferraris et al., Design, Synthesis, and Pharmacological Evaluation of Fluorinated Tetrahydrouridine Derivatives as Inhibitors of Cytidine Deaminase. J Med Chem. Mar. 27, 2014;57(6):2582-8. doi: 10.1021/jm401856k. Epub Feb. 24, 2014.
Goldberg et al., Participation of hemoglobins A and F in polymerization of sickle hemoglobin. J Biol Chem. May 25, 1977;252(10):3414-21.
Guarnone et al., Performance characteristics of Hemox-Analyzer for assessment of the hemoglobin dissociation curve. Haematologica. Sep.-Oct. 1995;80(5):426-30.
Johnson et al., Fetal hemoglobin induction by the histone deacetylase inhibitor, scriptaid. Cell Mol Biol (Noisy-le-grand). Sep. 5, 2005;51(2):229-38. Abstract only.
Jones et al., Adverse effects of a clinically relevant dose of hydroxyurea used for the treatment of sickle cell disease on male fertility endpoints. International journal of environmental research and public health. Mar. 2009;6(3):1124-44. doi:10.3390/ijerph6031124.
Junker et al., Novel histone deacetylase inhibitor CT-101 induces γ-globin gene expression in sickle erythroid progenitors with targeted epigenetic effects. Blood Cells Mol Dis. Mar. 2022;93:102626. doi: 10.1016/j.bcmd.2021.102626. Epub Nov. 17, 2021. Author Manuscript, 19 pages.
Karponi et al. Gene Therapy for Beta-Thalassemia: Updated Perspectives. Appl Clin Genet. Sep. 23, 2019;12:167-180. doi: 10.2147/TACG.S178546. eCollection 2019.
Koulnis et al., Identification and analysis of mouse erythroid progenitors using the CD71/TER119 flow-cytometric assay. J Vis Exp. Aug. 5, 2011;(54):2809(1-6). doi: 10.3791/2809.
Krishnamoorthy et al., Dimethyl fumarate increases fetal hemoglobin, provides heme detoxification, and corrects anemia in sickle cell disease. JCI Insight. Oct. 19, 2017;2(20):e96409(1-16). doi: 10.1172/jci.insight.96409.
Lanaro et al., A thalidomide-hydroxyurea hybrid increases HbF production in sickle cell mice and reduces the release of proinflammatory cytokines in cultured monocytes. Exp Hematol. Feb. 2018;58:35-38. doi: 10.1016/j.exphem.2017.10.003. Epub Nov. 3, 2017.
Lemaire, Anti-leukemic action of DNA methylation inhibitors and histone deacetylation. University of Montreal. Thesis presentation. Apr. 2009. 242 pages.
Li et al., Fetal hemoglobin induction in sickle erythroid progenitors using a synthetic zinc finger DNA-binding domain. Haematologica. Sep. 2018;103(9):e384-e387. doi: 10.3324/haematol.2017.185967. Epub Apr. 5, 2018.
Li et al., MIR-144-mediated NRF2 gene silencing inhibits fetal hemoglobin expression in sickle cell disease. Exp Hematol. Feb. 2019;70:85-96.e5. doi: 10.1016/j.exphem.2018.11.002. Epub Nov. 6, 2018.
Lopez et al., Salubrinal induces fetal hemoglobin expression via the stress-signaling pathway in human sickle erythroid progenitors and sickle cell disease mice. PLoS One. May 31, 2022;17(5):e0261799(1-18). doi: 10.1371/journal.pone.0261799.
Lukusa et al., Bone marrow transplantation or hydroxyurea for sickle cell anemia: long-term effects on semen variables and hormone profiles. Pediatric hematology and oncology. Jan. 1, 2009;26(4):186-94. doi: 10.1080/07357900902892780.
Marquez et al., Zebularine: a unique molecule for an epigenetically based strategy in cancer chemotherapy. Ann N Y Acad Sci. Nov. 2005;1058:246-54. doi: 10.1196/annals.1359.037.
Mavilio et al., Molecular mechanisms of human hemoglobin switching: selective undermethylation and expression of globin genes in embryonic, fetal, and adult erythroblasts. Proceedings of the National Academy of Sciences. Nov. 1983;80(22):6907-11. doi:10.1073/pnas.80.22.6907.
Metcalf et al., Discovery of GBT440, an Orally Bioavailable R-State Stabilizer of Sickle Cell Hemoglobin. ACS Med Chem Lett. Jan. 23, 2017;8(3):321-326. doi: 10.1021/acsmedchemlett.6b00491.
Mitchell et al., Novel approaches to treatment of sickle cell anaemia. Expert Opinion on Investigational Drugs. Nov. 1, 1999;8(11):1823-36. doi:10.1517/13543784.8.11.1823.
Momparler et al., In vitro cytotoxic and biochemical effects of 5-aza-2'-deoxycytidine. Cancer Research. Jun. 1977;37(6):1636-9.
Nagel et al., Structural bases of the inhibitory effects of hemoglobin F and hemoglobin A2 on the polymerization of hemoglobin S. Proc Natl Acad Sci U S A. Feb. 1979;76(2):670-2. doi: 10.1073/pnas.76.2.670. doi:10.1073/pnas.76.2.670.
Oksenberg et al., GBT440 increases haemoglobin oxygen affinity, reduces sickling and prolongs RBC half-life in a murine model of sickle cell disease. Br J Haematol. Oct. 2016;175(1):141-53. doi: 10.1111/bjh.14214. Epub Jul. 5, 2016.

(56) References Cited

OTHER PUBLICATIONS

Oseghale et al., Conjugate prodrug AN-233 induces fetal hemoglobin expression in sickle erythroid progenitors and β-YAC transgenic mice. Blood Cells Mol Dis. Nov. 2019;79:102345. doi: 10.1016/j.bcmd.2019.102345. Epub Jul. 9, 2019.

Pace et al., alpha-Amino butyric acid cannot reactivate the silenced gamma gene of the beta locus YAC transgenic mouse. Blood. Dec. 15, 1994;84(12):4344-53.

Parker et al., 5-Aza-4'-thio-2'-deoxycytidine, a New Orally Bioavailable Nontoxic "Best-in-Class": DNA Methyltransferase 1-Depleting Agent in Clinical Development. J Pharmacol Exp Ther. Nov. 2021;379(3):211-222. doi: 10.1124/jpet.121.000758. Epub Sep. 9, 2021.

Patel et al., Targeting of 5-aza-2'-deoxycytidine residues by chromatin-associated DNMT1 induces proteasomal degradation of the free enzyme. Nucleic acids research. Jul. 1, 2010;38(13):4313-24. doi:10.1093/nar/gkq187.

Platt et al., Mortality in sickle cell disease—life expectancy and risk factors for early death. New England Journal of Medicine. Jun. 9, 1994;330(23):1639-44. doi:10.1056/NEJM199406093302303.

Platt et al., Pain in sickle cell disease: rates and risk factors. New England Journal of Medicine. Jul. 4, 1991;325(1):11-6. doi:10.1056/NEJM199107043250103.

Poh et al., DNA Methyltransferase Activity Assays: Advances and Challenges. Theranostics. Jan. 6, 2016;6(3):369-91. doi: 10.7150/thno.13438. eCollection 2016.

Rivers et al., Oral administration of the LSD1 inhibitor ORY-3001 increases fetal hemoglobin in sickle cell mice and baboons. Exp Hematol. Nov. 2018;67:60-64.e2. doi: 10.1016/j.exphem.2018.08.003. Epub Aug. 17, 2018. Author Manuscript, 8 pages.

Ruiz et al., Hydroxymethylcytosine and demethylation of the γ-globin gene promoter during erythroid differentiation. Epigenetics. 2015;10(5):397-407. doi: 10.1080/15592294.2015.1039220.

Saunthararajah et al., Clinical effectiveness of decitabine in severe sickle cell disease. British journal of haematology. Apr. 2008;141(1):126-9. doi:10.1111/j.1365-2141.2008.07027.x.

Saunthararajah et al., Effects of 5-aza-2'-deoxycytidine on fetal hemoglobin levels, red cell adhesion, and hematopoietic differentiation in patients with sickle cell disease. Blood. Dec. 1, 2003;102(12):3865-70. doi:10.1182/blood-2003-05-1738.

Saunthararajah, Key clinical observations after 5-azacytidine and decitabine treatment of myelodysplastic syndromes suggest practical solutions for better outcomes. Hematology Am Soc Hematol Educ Program. 2013;2013:511-21. doi: 10.1182/asheducation-2013.1.511.

Schermelleh et al., Dynamics of Dnmt1 interaction with the replication machinery and its role in postreplicative maintenance of DNA methylation. Nucleic acids research. Jul. 1, 2007;35(13):4301-12. doi:10.1093/nar/gkm432.

Secrist et al., Synthesis and biological activity of 2'-deoxy-4'-thio pyrimidine nucleosides. J Med Chem. Aug. 1991;34(8):2361-6. doi: 10.1021/jm00112a007.

Shi et al., Sustained treatment of sickle cell mice with haptoglobin increases HO-1 and H-ferritin expression and decreases iron deposition in the kidney without improvement in kidney function. Br J Haematol. Nov. 2016;175(4):714-723. doi: 10.1111/bjh.14280. Epub Aug. 10, 2016.

Steinberg et al., Effect of hydroxyurea on mortality and morbidity in adult sickle cell anemia: risks and benefits up to 9 years of treatment. Jama. Apr. 2, 2003;289(13):1645-51. doi:10.1001/jama.289.13.1645.

Steinberg et al., Fetal hemoglobin in sickle cell anemia: determinants of response to hydroxyurea. Multicenter Study of Hydroxyurea. Blood. Feb. 1, 1997;89(3):1078-88.

Takemura et al., Zebularine exerts its antiproliferative activity through S phase delay and cell death in human malignant mesothelioma cells. Biosci Biotechnol Biochem. Jul. 2018;82(7):1159-1164. doi: 10.1080/09168451.2018.1459466. Epub Apr. 24, 2018.

Teicher et al., Abstract LB-B12: Pediatric Preclinical Testing Consortium evaluation of 4'-thio-2'-deoxycytidine (TdCyd) and 5-aza-4'-thio-2'-deoxycytidine { Aza-TdCyd}. Mol Cancer Ther. 2018; 17(1_Supplement): 1-2. https://doi.org/10.1158/1535-7163.TARG-17-LB-812.

Tiwari et al., Synthesis and anti-cancer activity of some novel 5-azacytosine nucleosides. Nucleosides Nucleotides Nucleic Acids. Dec. 2003;22(12):2161-70. doi: 10.1081/ncn-120026872.

Van Der Ploeg et al., DNA methylation in the human γδβ-globin locus in erythroid and nonerythroid tissues. Cell. Apr. 1, 1980;19(4):947-58. doi:10.1016/0092-8674(80)90086-0.

Vichinsky et al., A Phase 3 Randomized Trial of Voxelotor in Sickle Cell Disease. N Engl J Med. Aug. 8, 2019;381(6):509-519. doi: 10.1056/NEJMoa1903212. Epub Jun. 14, 2019.

West et al., Laboratory profile of sickle cell disease: a cross-sectional analysis. The Cooperative Study of Sickle Cell Disease. J Clin Epidemiol. Aug. 1992;45(8):893-909. doi: 10.1016/0895-4356(92)90073-v.

Wu et al., Correction of sickle cell disease by homologous recombination in embryonic stem cells. Blood. Aug. 15, 2006;108(4):1183-8. doi: 10.1182/blood-2006-02-004812. Epub Apr. 25, 2006.

Xu et al., Corepressor-dependent silencing of fetal hemoglobin expression by BCL11A. Proceedings of the National Academy of Sciences. Apr. 16, 2013;110(16):6518-23. doi:10.1073/pnas.1303976110.

Zhou et al., Hydroxycarbamide adherence and cumulative dose associated with hospital readmission in sickle cell disease: a 6-year population-based cohort study. Br J Haematol. Jul. 2018;182(2):259-270. doi: 10.1111/bjh.15396. Epub May 16, 2018.

Zhu et al., Loss of NRF2 function exacerbates the pathophysiology of sickle cell disease in a transgenic mouse model. Blood. Feb. 1, 2018;131(5):558-562. doi: 10.1182/blood-2017-10-810531. Epub Dec. 18, 2017.

Zhu et al., NRF2 mediates γ-globin gene regulation and fetal hemoglobin induction in human erythroid progenitors. Haematologica. Aug. 2017;102(8):e285-e288. doi: 10.3324/haematol.2016.160788. Epub May 4, 2017.

Lavelle et al., Effects of tetrahydrouridine on pharmacokinetics and pharmacodynamics of oral decitabine. Blood. Feb. 2, 2012;119(5):1240-7. doi: 10.1182/blood-2011-08-371690. Epub Dec. 7, 2011.

Molokie et al., Oral tetrahydrouridine and decitabine for non-cytotoxic epigenetic gene regulation in sickle cell disease: A randomized phase 1 study. PLoS Med. Sep. 7, 2017;14(9):e1002382. doi: 10.1371/journal.pmed.1002382. eCollection Sep. 2017.

Sohal et al., A pilot clinical trial of the cytidine deaminase inhibitor tetrahydrouridine combined with decitabine to target DNMT1 in advanced, chemorefractory pancreatic cancer. Am J Cancer Res. Sep. 1, 2020;10(9):3047-3060. eCollection 2020.

Guo et al., Stability of 5-fluoro-2'-deoxycytidine and tetrahydrouridine in combination. AAPS PharmSciTech. Mar. 2010;11(1):247-52. doi: 10.1208/s12249-010-9383-2. Epub Feb. 12, 2010.

Voytek et al., Comparative studies of the cytostatic action and metabolism of 5-azacytidine and 5,6-dihydro-5-azacytidine. Cancer Res. Jul. 1977;37(7 Pt 1):1956-61.

\* cited by examiner

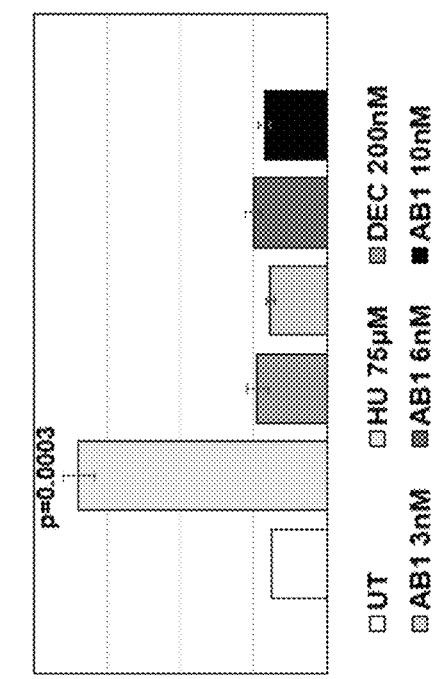
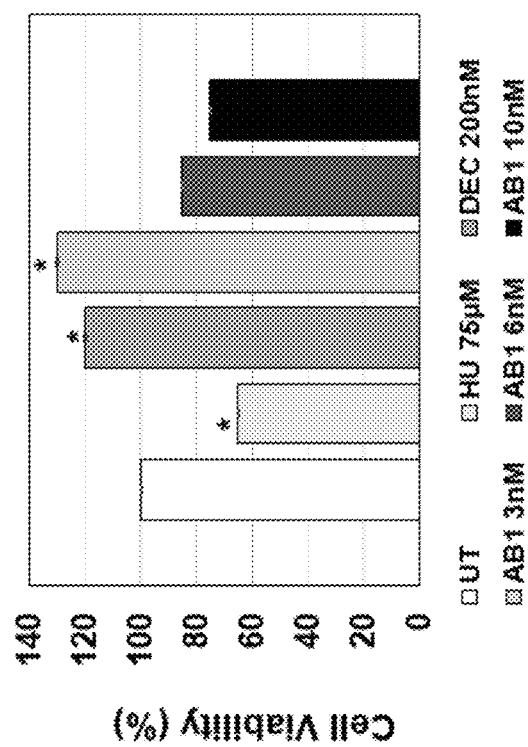
FIG. 6A
FIG. 6B

COMPOSITIONS COMPRISING 2'-DEOXYCYTIDINE ANALOGS AND USE THEREOF FOR THE TREATMENT OF SICKLE CELL DISEASE, THALASSEMIA, AND CANCERS

CROSS REFERENCE TO RELATED APPLICATIONS

This patent application claims the benefit of U.S. Provisional Patent Application No. 63/257,541, filed Oct. 19, 2021, which is incorporated herein by reference in its entirety.

BACKGROUND

Sickle cell disease is an inherited condition in which mutated hemoglobin polymerizes in red blood cells. This polymerization causes red blood cells to adopt a sickle or crescent shape which can lead to premature death of red blood cells and thus insufficient numbers of healthy red blood cells, in turn causing pain, increased susceptibility to infection, fatigue, and blockage of blood vessels. Individuals with sickle cell disease are at increased risk of stroke and clotting disorders, blindness, gallstones, pulmonary hypertension, pregnancy complications, and organ damage and many of those affected die prematurely.

Thalassemia is another inherited blood disorder in which abnormal hemoglobin, or an inadequate amount of hemoglobin is produced. Various forms of thalassemia are possible depending on where the mutation in hemoglobin is found (e.g., α-globin or β-globin chain proteins) and whether a person has one or two defective genes; these forms vary in the severity of symptoms. Children born with thalassemia can appear normal at birth but may later develop anemia, bone deformities, fatigue, shortness of breath, stunted growth, and/or jaundice. In some cases, thalassemia can result in stillbirth.

During the development of a fetus, fetal hemoglobin (HbF) is the predominant form of hemoglobin. After birth, adult hemoglobin (HbA) is normally produced, while HbF genes are silenced by DNA methylation enzymes including DNA methyltransferase 1 (DNMT1). Induction of HbF production has typically been effective in the amelioration of clinical symptoms of sickle cell disease and thalassemia.

DNA methylation is also widely studied as an epigenetic modification in mammals and can be implicated in the development of certain cancers. For example, aberrant DNMT activity may result in hypermethylation of tumor-suppressor genes, of DNA that relates to the expression noncoding microRNAs, or in the promoter regions of other genes related to DNA repair. Thus, regulation of DNMT activity can be a useful approach for cancer therapy and/or the treatment of diseases associated with abnormal cell proliferation.

Cytidine analogs, including 5-aza-4'-thio-2'-deoxycytidine and 5-fluoro-2'-deoxycytidine, have been evaluated in cancer clinical trials for anti-DNMT activity. 5-aza-4'-thio-2'-deoxycytidine and 5-fluoro-2'-deoxycytidine have not been evaluated as therapeutic agents for Sickle cell disease, Thalassemia or anemia disorders. Although these compounds have shown potent in vitro activity and in vivo pharmacokinetic properties, they have shown no significant therapeutic response in pediatric brain tumor models and have thus been deprioritized for certain cancer treatments. However, treatments with cytidine analogs have traditionally been carried out intravenously, which can lead to lack of patient compliance and exhibit severe genotoxic and cytotoxic effects. Furthermore, IV administration may not result in a sustained exposure to the analogs over a given time-course of treatment and results in limited or negligible distribution of effective therapeutic dose to diseased tissues, like spleen and liver. Furthermore, current dosage forms of cytidine analogs administered concurrently with tetrahydrouridine have exhibited cytotoxic effects.

Despite advances in hematology and cancer research, there is still a scarcity of compounds and compositions that are potent, efficacious, and selective inhibitors of DNA methyltransferase 1 enzymes and also effective in the treatment of hematological disorders associated with DNMT1 activity and diseases associated with abnormal cell proliferation in which DNMT1 is involved. Additionally, existing treatments may require hardships such as traveling to medical facilities for infusions, which may decrease patient compliance. Ideally, a treatment for a blood disorder such as sickle cell disease or thalassemia could be administered to a subject at home in a single dosage form, would be acid-stable, would be in a low dose with few or no side effects including no cytotoxic effects, and would be capable of timed or sequential release of separate ingredients for maximum synergistic therapeutic effects. These needs and other needs are satisfied by the present disclosure.

SUMMARY

In accordance with the purpose(s) of the present disclosure, as embodied and broadly described herein, the disclosure, in one aspect, relates to pharmaceutical compositions comprising 2'-deoxycytidine analogs, oral and other dosage formulations containing the same, and methods of making the same. In another aspect, the disclosure relates to methods of treating hematological disorders and diseases associated with abnormal cell proliferation using the same. In a still further aspect, the disclosure relates to kits comprising 2'-deoxycytidine analogs useful for treating hematological disorders and diseases associated with abnormal cell proliferation. In still another aspect, the disclosure relates to methods for increasing fetal hemoglobin levels in a subject.

Disclosed herein are pharmaceutical compositions comprising a therapeutically effective amount of at least one DNMT1 inhibitor, e.g., at least one 2'-deoxycytidine analog, as disclosed herein; and at least one pharmaceutically acceptable excipient.

Also disclosed herein are pharmaceutical compositions comprising a therapeutically effective amount of a first therapeutic agent; and at least one pharmaceutically acceptable excipient.

Also disclosed herein are pharmaceutical compositions comprising a therapeutically effective amount of a first therapeutic agent; and at least one pharmaceutically acceptable excipient; wherein the first therapeutic agent is 5-aza-4'-thio-2'-deoxycytidine, 5-fluoro-2'-deoxycytidine, a pharmaceutically acceptable salt thereof, or combinations thereof.

Also disclosed herein are pharmaceutical compositions comprising a therapeutically effective amount of a first therapeutic agent; a second therapeutic agent; and at least one pharmaceutically acceptable excipient.

Also disclosed herein are pharmaceutical compositions comprising a therapeutically effective amount of a first therapeutic agent and a second therapeutic agent; wherein the first therapeutic agent is a at least one DNMT1 inhibitor, e.g., at least one 2'-deoxycytidine analog; and wherein the second therapeutic agent is at least one CDA inhibitor as disclosed herein; and at least one pharmaceutically acceptable excipient.

Also disclosed herein are pharmaceutical compositions comprising a therapeutically effective amount of a first therapeutic agent and a second therapeutic agent; wherein the first therapeutic agent is a at least one DNMT1 inhibitor, e.g., at least one 2'-deoxycytidine analog; and wherein the second therapeutic agent is at least one CDA inhibitor as disclosed herein; and at least one pharmaceutically acceptable excipient; wherein the first therapeutic agent is 5-aza-4'-thio-2'-deoxycytidine, 5-fluoro-2'-deoxycytidine, a pharmaceutically acceptable salt thereof, or combinations thereof; and wherein the second therapeutic agent comprises a tetrahydrouridine derivative, a 2'-fluorinated tetrahydrouridine derivative, a pharmaceutically acceptable salt thereof, or combinations thereof.

Also disclosed herein are pharmaceutical compositions comprising a therapeutically effective amount of at least one DNMT1 inhibitor, e.g., at least one 2'-deoxycytidine analog, as disclosed herein; optionally at least one CDA inhibitor as disclosed herein; and at least one pharmaceutically acceptable excipient.

Also disclosed herein are methods for treating a hematological disorder in a subject, the method comprising administering a first therapeutic agent, wherein the first therapeutic agent is 5-aza-4'-thio-2'-deoxycytidine, 5-fluoro-2'-deoxycytidine, a pharmaceutically acceptable salt thereof, or combinations thereof.

Also disclosed herein are methods for treating a hematological disorder in a subject, the method comprising administering a first therapeutic agent and a second therapeutic agent; wherein the first therapeutic agent is 5-aza-4'-thio-2'-deoxycytidine, 5-fluoro-2'-deoxycytidine, a pharmaceutically acceptable salt thereof, or combinations thereof; and wherein the second therapeutic agent comprises a tetrahydrouridine derivative, a 2'-fluorinated tetrahydrouridine derivative, a pharmaceutically acceptable salt thereof, or combinations thereof.

Also disclosed herein are products for use in the treatment of a hematological disorder in a subject, the method comprising administering a first therapeutic agent, wherein the first therapeutic agent is 5-aza-4'-thio-2'-deoxycytidine, 5-fluoro-2'-deoxycytidine, a pharmaceutically acceptable salt thereof, or combinations thereof.

Also disclosed herein are products for use in the treatment of a hematological disorder in a subject, the method comprising administering a first therapeutic agent and a second therapeutic agent; wherein the first therapeutic agent is 5-aza-4'-thio-2'-deoxycytidine, 5-fluoro-2'-deoxycytidine, a pharmaceutically acceptable salt thereof, or combinations thereof; and wherein the second therapeutic agent comprises a tetrahydrouridine derivative, a 2'-fluorinated tetrahydrouridine derivative, a pharmaceutically acceptable salt thereof, or combinations thereof.

Also disclosed herein are methods for treating a hematological disorder in a subject, the method comprising administering a first therapeutic agent and optionally a second therapeutic agent; (a) wherein the first therapeutic agent is 5-aza-4'-thio-2'-deoxycytidine, 5-fluoro-2'-deoxycytidine, a pharmaceutically acceptable salt thereof, or combinations thereof; and (b) wherein the second therapeutic agent is tetrahydrouridine, a 2'-fluorinated tetrahydrouridine derivative, a pharmaceutically acceptable salt thereof, or combinations thereof.

Also disclosed herein are uses of products for treatment of a hematological disorder in a subject, the use comprising administering a therapeutically effective amount of a disclosed pharmaceutical composition or a disclosed therapeutic agent to a subject. In a further aspect, the use comprises administering a therapeutically effective amount of a disclosed pharmaceutical composition comprising a 2'-deoxycytidine analog.

Also disclosed herein are uses of products for treatment of a disorder to increase fetal hemoglobin expression in a subject, the use comprising administering a therapeutically effective amount of a disclosed pharmaceutical composition or a disclosed therapeutic agent to a subject.

Also disclosed herein are uses of uses of products for treatment of a disease associated with abnormal cell proliferation in a subject, the use comprising administering a therapeutically effective amount of a disclosed pharmaceutical composition to a subject, e.g., a disclosed pharmaceutical composition comprising a 2'-deoxycytidine analog.

Also disclosed herein are kits comprising at least one disclosed compound, or a pharmaceutically acceptable salt, hydrate, solvate, or polymorph thereof, and one or more of: (a) at least one agent known to decrease DNMT1 activity; (b) at least one agent known to treat a disorder associated with DNMT1 activity; (c) instructions for treating a disorder associated with DNMT1 activity; or (d) instructions for administering the compound in connection with another sickle cell disease, thalassemia, or anti-cancer therapy.

Also disclosed herein are methods of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Still another aspect of the invention relates to a method of studying a biological system, e.g., a model animal for a clinical condition, or biological sample comprising a DNMT1 protein, the method comprising: (a) contacting the biological system or sample with a compound of the invention; and (b) determining the effects caused by the compound on the biological system or sample.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 5A shows representative data relating to induction by treatment with AB1 of HbF expression in K562 cells. To determine the optimal concentration of disclosed compound AB1 that activates γ-globin and HbF expression K562 cells were treated with AB1 3-200 nM for 24-96 hours and cell viability analyzed by trypan blue exclusion staining. Shown in the graph is the mean±standard error of mean (SEM) for n=3 replicates. p<0.05 was considered statistically significant. FIG. 5B shows representative data relating to mRNA expression levels as determined by RT-qPCR analysis to measure γ-globin mRNA levels. FIG. 5C shows representative data relating to F-cell levels as measured by flow cytometry with anti-HbF FITC antibody. FIG. 5D shows representative data relating to mean fluorescence intensity (MFI) used to measure the level of HbF per cells after treatment with the various agents shown. Each of FIGS. 5A-5D shows therein the key to the shading of the bars.

FIG. 6A shows representative data relating to cell viability that was analyzed by trypan blue exclusion. Shown in the graph is the mean±SEM for n=6. FIG. 6A shows representative data relating to the level of CD71$^+$ cells quantified by flow cytometry. FIG. 6A shows representative data relating to the level of erythroid differentiation quantified by CD235a$^+$ cells using flow cytometry. Each of FIGS. 6A-6C shows therein the key to the shading of the bars.

FIG. 7A shows representative data relating to the level of γ-globin mRNA quantified by RT-qPCR analysis. FIG. 7A shows representative data relating to β-globin mRNA quantified by RT-qPCR analysis. Shown in the graph is the mean±SEM for n=3 replicates. Each of FIGS. 7A-7B shows therein the key to the shading of the bars.

FIG. 8A shows representative data relating to the levels of F-cells were determined by flow cytometry. Shown in the graph is the mean±SEM for n=6 replicates. FIG. 8B shows representative data relating to the mean fluorescence intensity (MFI) measured the level of HbF per cell. FIG. 8C shows representative data relating to Western blot analysis was completed to quantify HbF and HbS protein levels under the various treatment conditions. FIG. 8D shows representative data relating to Western blot analysis to measure protein levels of DNMT1, n=2. Each of FIGS. 8A-8B shows therein the key to the shading of the bars. In FIGS. 8C-8D, "UT" indicates untreated cells; "HU" indicates hydroxyurea; "DEC" indicates decitabine; and "AB1" indicates disclosed compound AB1; the concentrations are indicated above the graph below the text indicating treatment compound.

FIG. 9A shows representative contrast microscopy images relating to various treatments and reduction of the level of sickle erythroid progenitors. FIG. 9B shows representative quantitative data (from image data such as that shown in FIG. 9A) for the number of sickled cells as a percent of a total of 500 cells counted, n=3. In FIGS. 9A-9B, "UT" indicates untreated cells; "HU" indicates hydroxyurea; "DEC" indicates decitabine; and "AB1" indicates disclosed compound AB1; the concentrations are indicated, and concentration used is adjacent to the text indicating treatment compound.

Figure 1:
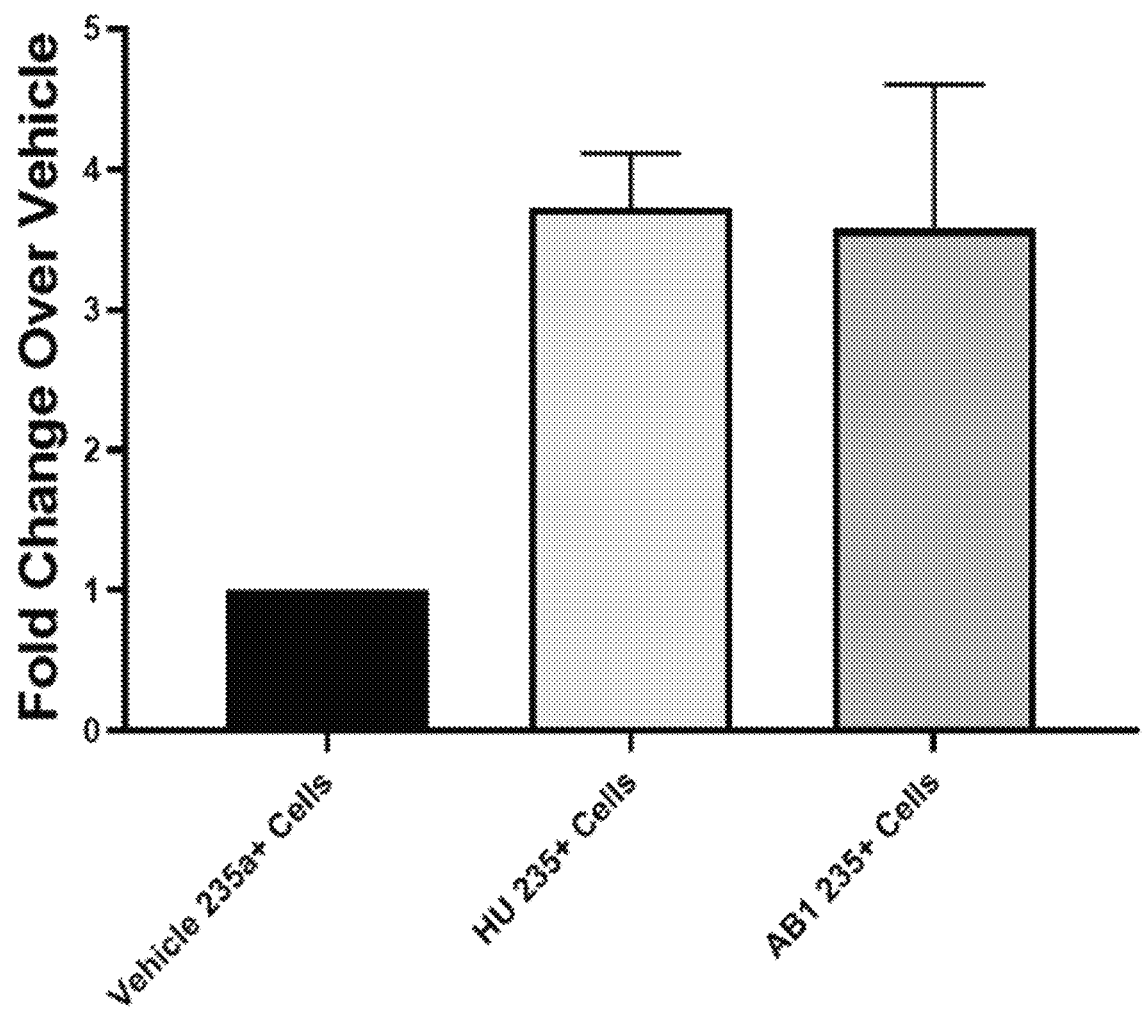
FIG. 1 shows representative data for change in 235+ cells in sickle erythroid progenitors after treatment with hydroxyurea (HU, 75 µM) or disclosed compound AB1 (10 nM).
Figure 2:
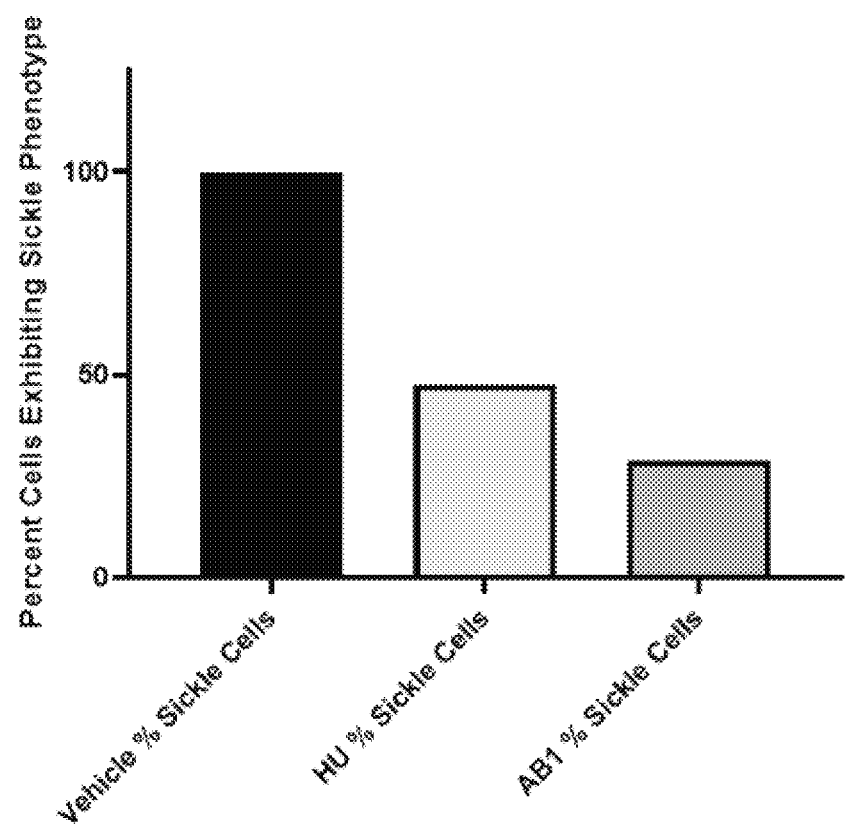
FIG. 2 shows representative data for the percent sickled erythrocytes exposed to 2% oxygen after treatment with hydroxyurea (HU, 75 µM) or disclosed compound AB1 (10 nM).
Figure 3:
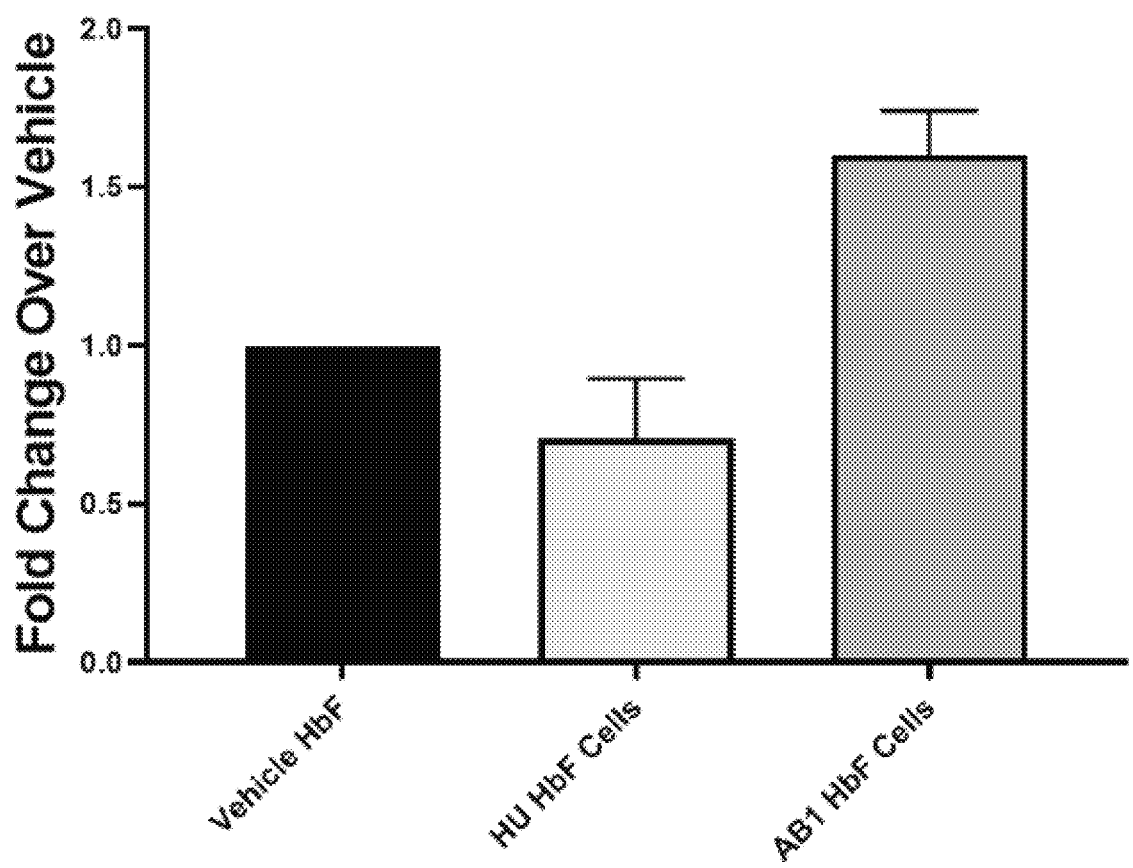
FIG. 3 shows representative data for HbF cell response of sickle erythroid progenitors to treatment with hydroxyurea (HU, 75 µM) or disclosed compound AB1 (10 nM).
Figure 4:
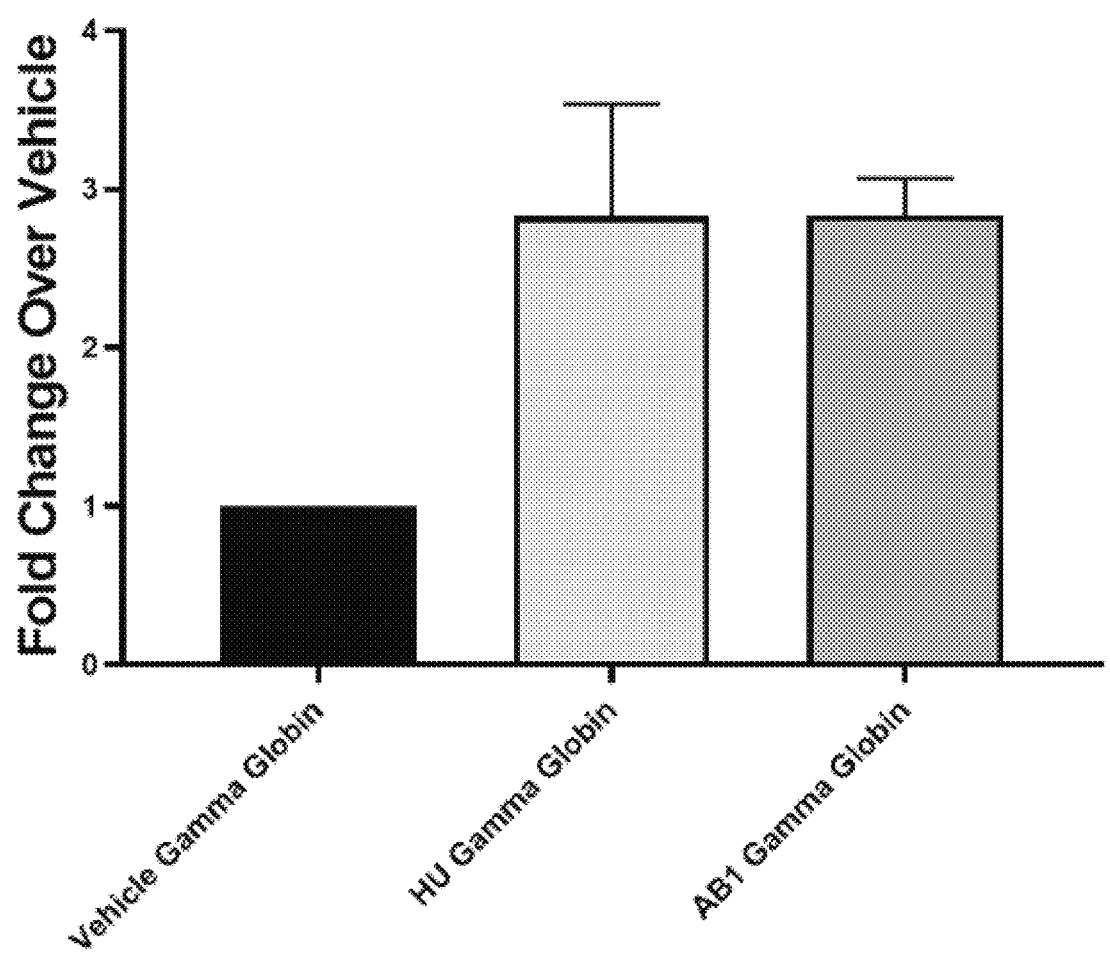
FIG. 4 shows representative data for the gamma globin induction in sickle erythroid progenitors in response to treatment with hydroxyurea (HU, 75 µM) or disclosed compound AB1 (10 nM).

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a filler," "a 2'-deoxycytidine analog," or "an excipient," includes, but is not limited to, combinations of two or more such fillers, 2'-deoxycytidine analogs, or excipients, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "DNA methyltransferase 1" and "DNMT1" can be used interchangeably and refer to an enzyme encoded by a gene in humans with a cytogenetic location of 19p13.2 and a molecular location of base pairs 10,133,345-10,194,952 on chromosome 19 (*Homo sapiens* Annotation Release 109.20190607, GRCh38.p13). The gene structure in humans has at least 37, and possibly as many as 40, exons. DNMT1 has an EC classification of 2.1.1.37, an intracellular location within the nucleus, and catalyzes the transfer of methyl groups to specific CpG structures in DNA. It is the most abundant DNA methyltransferase in mammalian cells and believed to be a key maintenance methyltransferase in mammals. It predominantly methylates hemimethylated CpG di-nucleotides in the mammalian genome via catalyzing the transfer of methyl groups to specific CpG structures in DNA and is responsible for maintaining methylation patterns established in development. The enzyme is about 1620 amino acids long, the first 1100 amino acids constituting the regulatory domain, and the remaining residues constituting the catalytic domain. These are joined by Gly-Lys repeats. Both domains are required for the catalytic function of DNMT1. DNMT1 has also been referred to as CXXC-type zinc finger protein 9, DNA (cytosine-5-)-methyltransferase 1, DNA methyltransferase HsaI, and MCMT.

The term "DNA methyltransferase 1 inhibitor" and "DNMT1 inhibitor" can be used interchangeably and refer to a composition that selectively blocks or inactivates DNMT1. The term "DNA methyltransferase 1 inhibitor" and "DNMT1 inhibitor" also refer to a compound that selectively blocks or inactivates the transfer of methyl groups to specific CpG structures in DNA by the DNMT1. As used herein, the term "selectively blocks or inactivates" refers to a compound that preferentially binds to and blocks or inactivates DNMT1 with a greater affinity and potency, respectively, than its interaction with the other sub-types of the methyltransferase family. Compounds that block or inactivate DNMT1, but that may also block or inactivate other methyltransferase sub-types, as partial or full inhibitors, are contemplated. The term "DNMT1 inhibitor" also refers to a compound that inhibits DNMT1 expression. Typically, a DNMT1 inhibitor compound is a small organic molecule, a polypeptide, an aptamer, an antibody, an intra-antibody, an oligonucleotide or a ribozyme. Tests and assays for determining whether a compound is a DNMT1 inhibitor are well known by the skilled person in the art such as described in Poh et al., Theranostics (2016) 6(3): 369-391. In some instances, the DNMT1 inhibitor can be a 2'-deoxycytidine analog.

As used herein, the term "cytidine deaminase" and "CDA" refers to cytidine deaminase "CDA", a key enzyme of the pyrimidine salvage pathway that catalyzes the hydrolytic deamination of cytidine and deoxycytidine to uridine and deoxyuridine, respectively 9. Because of the structural similarity to cytidine, several nucleoside-based drugs are also subject to deamination by CDA (Ferraris et al, 2014). In Pancreatic ductal adenocarcinoma, cytidine deaminase "CDA" inactivates gemcitabine via CDA-mediated conversion to difluorodeoxyuridine.

The term "cytidine deaminase inhibitor" or "CDA inhibitor" can be used interchangeably and refer to a composition that selectively blocks or inactivates the cytidine deaminase. The term "cytidine deaminase inhibitor" also refers to a compound that selectively blocks or inactivates hydrolytic deamination mediated by the cytidine deaminase. As used herein, the term "selectively blocks or inactivates" refers to a compound that preferentially binds to and blocks or inactivates CDA with a greater affinity and potency, respectively, than its interaction with the other sub-types of the deaminase family. Compounds that block or inactivate CDA, but that may also block or inactivate other deaminase sub-types, as partial or full inhibitors, are contemplated. The term "CDA inhibitor" also refers to a compound that inhibits CDA expression. Typically, a CDA inhibitor compound is a small organic molecule, a polypeptide, an aptamer, an antibody, an intra-antibody, an oligonucleotide or a ribozyme. Tests and assays for determining whether a compound is a CDA inhibitor are well known by the skilled person in the art such as described in Ferraris et al, 2014; U.S. Pat. No. 6,136,791; WO2009/052287.

As used herein, "AN-233" and "1-(butyryloxy)ethyl-5-amino-4-oxopentanoate" can be used interchangeably and refer to a conjugate prodrug having a structure represented by the formula:

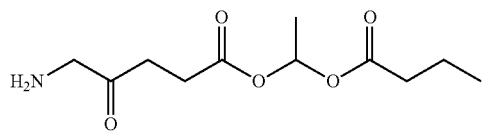

As used herein, "administering" can refer to an administration to a subject of one or more therapeutic agents by a route of administration that can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used interchangeably herein, "subject," "individual," or "patient" can refer to a vertebrate organism, such as a mammal (e.g., human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as sickle cell disease, thalassemia, and/or a cancer. The effect can be therapeutic in terms of a partial or complete cure of a disease, condition, symptom or adverse effect attributed to the disease, disorder, or condition. The term "treatment" as used herein can include any treatment of sickle cell disease, thalassemia, and/or a cancer in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain. In one aspect, treatment of sickle cell disease or thalassemia can increase total hemoglobin or increase fetal hemoglobin or reduce anemia or reduce clumping among misshapen erythrocytes.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, "therapeutic" can refer to treating, healing, and/or ameliorating a disease, disorder, condition, or side effect, or to decreasing in the rate of advancement of a disease, disorder, condition, or side effect.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. As used herein, "therapeutically effective amount" refers to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function. In general, a "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

As used herein, the term "prophylactically effective amount" refers to an amount effective for preventing onset or initiation of a disease or condition.

As used herein, the term "effective amount" can refer to an amount of an inactive ingredient that is sufficient to achieve the desired modification of a physical property of the composition or material. For example, an "effective amount" of a binder refers to an amount that is sufficient to achieve the desired improvement in the property modulated by the formulation component, The specific level in terms of wt % in a composition required as an effective amount will depend upon a variety of factors including the amount and type of binder, amount and type of active ingredient, presence of other components in the formulation, and delivery mechanism of the pharmaceutical composition disclosed herein.

As used herein, a "hematological disorder" refers to a disease or disorder that primarily affects blood and/or blood-forming organs. In a further aspect, hematological disorders include genetic disorders such as, for example, sickle cell disease, thalassemia, methemoglobinemia, and the like. In another aspect, hematological disorders can further include anemias, myelodysplastic syndrome, myeloproliferative disorders, coagulopathies, hematological malignancies including, but not limited to, Hodgkin's disease, non-Hodgkin's lymphoma, multiple myeloma, and leukemias. In still another aspect, hematological disorders can include hemochromatosis. In any of these aspects, the methods and compositions disclosed herein can be useful for treating hematological disorders.

As used here, "abnormal cell proliferation" refers to a condition in which cell cycle regulation is disrupted such as that which occurs, for example, when a proto-oncogene, DNA repair gene, or tumor suppressor gene undergoes a mutation. In a further aspect, abnormal cell proliferation can lead to an accumulation of abnormal cell numbers and a condition such as, for example, cancer. In one aspect, the methods and compositions disclosed herein can be useful for treating diseases associated with abnormal cell proliferation including, but not limited to, bladder cancer, breast cancer, brain cancer, an endocrine cancer, retinoblastoma, cervical cancer, colon cancer, rectal cancer, endometrial cancer, renal cell carcinoma, renal pelvis carcinoma, Wilms tumor, a cancer of the oral cavity, liver cancer, gall bladder cancer, cholangiocarcinoma, melanoma, mesothelioma, myelodysplastic syndrome, acute myelogenous leukemia, non-small cell lung cancer, basal cell skin cancer, squamous cell skin cancer, ovarian cancer, pancreatic cancer, prostate cancer, soft tissue sarcoma, osteosarcoma, small cell lung cancer, thyroid cancer, other cancers, or a combination thereof.

As used herein, "area-under-the-curve value" describes drug concentration in blood plasma overtime. In one aspect, drug concentration is measured at discrete time points and area-under-the-curve is estimated using the trapezoid rule (i.e., a technique for approximating the definite integral of a curve). In one aspect, area-under-the-curve value is useful for approximating bioavailability of a drug over time.

"Maximum plasma concentration" is the peak concentration of a pharmaceutical or drug achieved in the plasma of a subject to whom a drug has been administered. Maximum plasma concentration is typically measured after a first dose but before a second dose is administered.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, troubleshooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents and are meant to include future updates.

As used herein, "dose" or "dosage" can refer to physically discrete units suitable for use in a subject, each unit containing a predetermined quantity of a disclosed compound and/or a pharmaceutical composition thereof calculated to produce the desired response or responses in association with its administration. The dose can be administered in a single dosage or in multiple dosages, for example from 1 to 4 or more times per day. When multiple dosages are used, the amount of each dosage can be the same or different. Moreover, a dose comprising a first therapeutic agent and a second therapeutic agent can be in separate dosage forms or combined in a single dosage form.

As used herein, "single dosage form", "single dose", "unit dosage form", "unit dose", and "single dose form" can be used interchangeably and refer to a single drug administration entity combining at least one disclosed therapeutic agent, e.g., a DNMT1 inhibitor such as one or more 2'-deoxycytidine analog, in a therapeutically effective amount, optionally additional disclosed therapeutic agents, a pharmaceutically acceptable carrier, and other excipients, inactive ingredients, and the like as disclosed herein. In various instances, the single dosage form can be a single tablet, capsule, or liquid. That is, "single dosage form" refers to a presentation form comprising a defined amount of at least one disclosed therapeutic agent, with the intention of applying the total of such amount as a single dosage. As an illustration, a representative single dosage of the present disclosure can be a tablet or a capsule comprising at least 2'-deoxycytidine analog in an amount to provide a therapeutically effective dose as disclosed herein below. This aforementioned list of single dosage forms is not intended to be limiting in any way, but merely to represent typical examples of single dosage forms.

It is further understood that a single dosage form refers to physically discrete units suitable as unitary dosages, each unit containing a predetermined quantity of active ingredient calculated to produce the desired therapeutic effect in association with the required pharmaceutical carrier. That is, a "single dosage form" can be a single dose wherein all active and inactive ingredients are combined in a suitable system, such that the patient or person administering the drug to the patient can open a single container or package with the entire dose contained therein. In some instances, a "single dosage form" can be a powder in a packet or container comprising a therapeutically effective amount of one or more therapeutic agents that can be mixed with a specified volume of liquid. Typical examples of unit dosage forms are tablets (including scored or coated tablets), capsules or pills for oral administration; powder packets; wafers; and segregated multiples thereof. This list of unit dosage forms is not intended to be limiting in any way, but merely to represent typical examples of unit dosage forms.

As used herein, "combined formulation" refers to the mixture of two or more isolated pharmaceutical compositions comprising, e.g., a 2'-deoxycytidine analog and a CDA inhibitor in a representative non-limiting example, into a single dosage form.

As used herein, "combined administration" or "co-administration" refers to administration of two or more isolated pharmaceutical compositions, e.g., a 2'-deoxycytidine analog and a CDA inhibitor in a representative non-limiting example, in separate dosage forms (e.g., separate pills) that can be taken together (simultaneous administration) or in a particular sequence (sequential administration).

As used herein, the terms "mixture" and "combination", e.g., a combination therapeutic agent, can refer to multiple components or ingredients formed into one resulting component, e.g., a single dosage form comprising components that can be separate but contained in a single dosage form. A combination therapeutic is also inclusive of components that can be administered in the same treatment regimen even if not physically formed into a single component or contained in a single dosage form. As used herein, the terms "mixture" and "combination" may be used interchangeably.

The term "pharmaceutically acceptable" describes a material that is not biologically or otherwise undesirable, i.e., without causing an unacceptable level of undesirable biological effects or interacting in a deleterious manner.

The term "pharmaceutically acceptable carrier" is used herein to refer to a carrier that is useful in preparing a pharmaceutical composition that is generally safe, non-toxic and neither biologically nor otherwise-undesirable, and is acceptable for veterinary use as well as human pharmaceutical use. A "pharmaceutically acceptable carrier" as used in the specification and claims can include both one and more than one such carrier. By "pharmaceutically acceptable" it is meant the carrier must be compatible with the other ingredients of the formulation and not deleterious to the recipient thereof.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C1 to C6 alkyl esters and C5 to C7 cycloalkyl esters, although C1 to C4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C1 to C6 alkyl amines and secondary C1 to C6 dialkyl amines. In the case of secondary amines, the amine can also be in the form of a 5- or 6-membered heterocycle containing one nitrogen atom. Amides derived from ammonia, C1 to C3 alkyl primary amides and C1 to C2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

As used herein, "oral administration" or "orally" refers to the introduction of a pharmaceutical composition into a subject by way of the oral cavity (e.g., in liquid or solid form), e.g., a capsule or tablet, although other oral dosage forms are contemplated and disclosed herein. Oral administration is inclusive of dosage forms that are swallowed or ingested by the oral cavity, and transit, in some form, the gastro-intestinal tract such that therapeutic agents are absorbed, at least in part, from the gastro-intestinal tract. It is understood that oral administration is also inclusive of any mode of administration that is by way of the oral cavity, including, but not limited to, sublingual administration and buccal administration.

As used herein, "sublingual administration" or "sublingually" refers to the introduction of a pharmaceutical composition into a subject by application to the mucosal surface under the tongue (within the oral cavity) such that the composition is absorbed into the subject.

As used herein, "buccal administration" or "buccal" refers to the introduction of a pharmaceutical composition into a subject by application to the mucosal surface lining the cheek (within the oral cavity) such that the composition is disintegrated, dissolved and absorbed into the subject. In some instances, disintegration and dissolution occurs in the buccal cavity, followed by absorption of all or a portion of the pharmaceutically active ingredient through the buccal mucosa. The remaining pharmaceutically active ingredient, if any, is then swallowed and absorbed enterally. As used herein, "intranasal administration" or "intranasally" refers to the introduction of a pharmaceutical composition within the nasal cavity.

Therapeutic Agents.

The disclosed pharmaceutical compositions utilize disclosed therapeutic agents, alone and in various combinations as contemplated herein.

In one aspect, the pharmaceutical compositions disclosed herein comprise a therapeutic agent comprising at least one DNMT1 inhibitor. A disclosed DNMT1 inhibitor can be at least one 2'-deoxycytidine analog as disclosed herein, an non-nucleoside analogue DNMT1 inhibitor, e.g., not a 2'-deoxycytidine analog, and combinations thereof. In some instances, the DNMT1 inhibitor, e.g., at least one 2'-deoxycytidine analog, can be referred to as a first therapeutic agent.

It is understood herein throughout that unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. For example, in the disclosed 2'-deoxycytidine analog compounds, such as a compound of Formula I, comprises one or more of the 8 ring stereoisomers, individually or mixtures of each, e.g., such as (2R, 4S, 4R).

In one aspect, the pharmaceutical compositions disclosed herein comprise a DNMT1 inhibitor comprising at least one 2'-deoxycytidine analog. In a further aspect, the at least one 2'-deoxycytidine analog has a structure represented by a formula, Formula I:

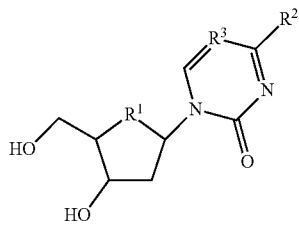

Formula I wherein $R^1$ is selected from S and O; wherein $R^2$ is selected from OH and NH; wherein $R^3$ is selected from N and $CR^4$; and wherein $R^4$ is selected from H, aliphatic acyl, aromatic acyl, halo, alkyl, haloalkyl, alkoxy, alkenyl, haloalkenyl, alkynyl, amino, monoalkylamino, dialkylamino, cyano, aryl, and nitro. In a still further aspect, when $R^4$ is halo, $R^4$ can be selected from fluoro, chloro, bromo, or iodo.

In a further aspect, a compound of Formula I can in a particular aspect can be a compound have structure represented by a formula:

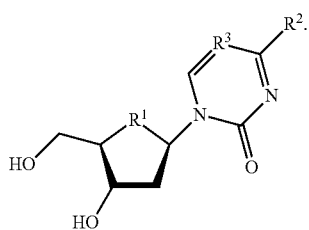

In various aspects, the at least one 2'-deoxycytidine analog is selected from a structure represented by a formula:

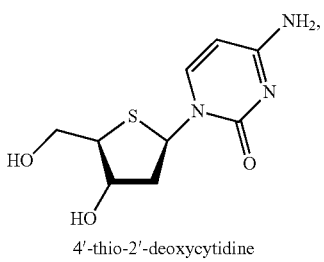

4'-thio-2'-deoxycytidine

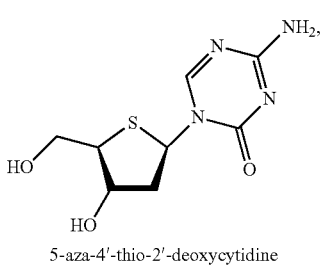

5-aza-4'-thio-2'-deoxycytidine

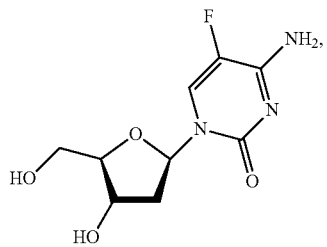

5-fluoro-2'-deoxycytidine or combinations thereof.

In various aspects, the at least one 2'-deoxycytidine analog can be decitabine or 5-aza-2'-deoxycytidine (trade name Dacogen) is the compound 4-amino-1-(2-deoxy-b-D-erythro-pentofuranosyl)-1,3,5-triazin-2(1H)-one, having the structure given by the formula shown immediately below.

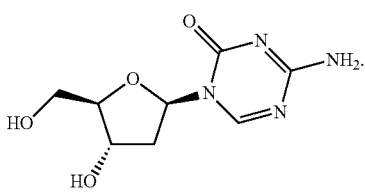 [SMILES: Nc1ncn([C@H]2C[C@H](O)[C@@H](CO)O2)c(=O)n1]

Decitabine is believed to exert its effects after phosphorylation and direct incorporation into DNA. However, decitabine also inhibits DNA methyltransferase, causing hypomethylation of DNA and cellular differentiation or apoptosis. It is believed that decitabine-induced hypomethylation in neoplastic cells may restore normal function to genes that are critical for the control of cellular differentiation and proliferation. In rapidly dividing cells, the cytotoxicity of decitabine may also be attributed to the formation of covalent adducts between DNA methyltransferase and compound that has been incorporated into DNA. Non-proliferating cells are relatively insensitive to decitabine.

In a further aspect, the at least one 2'-deoxycytidine analog is 4'-thio-2'-deoxycytidine, which is also referred to herein as AB1, and has the structure represented by the formula:

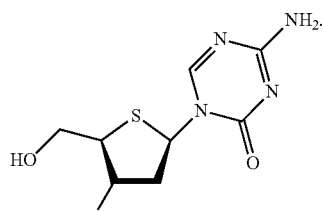

In various aspects, the DNMT1 inhibitor can be a nucleoside analog that is not a 2'-deoxycytidine analog such as 5-azacitidine (tradename: Vidaza), having the chemical name 4-amino-1-β-D-ribofuranosyl-s-triazin-2(1H)-one, having a structure represented by the formula immediately below.

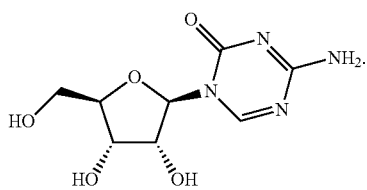 [SMILES: Nc1ncn([C@@H]2O[C@H](CO)[C@@H](O)[C@H]2O)c(=O)n1]

Azacytidine is believed to act by causing hypomethylation of DNA. The concentration of azacytidine required for maximum inhibition of DNA methylation in vitro does not cause major suppression of DNA synthesis.

In various aspects, the DNMT1 inhibitor can be a nucleoside analog that is not a 2'-deoxycytidine analog such as zebularine, also known as 1-(β-D-ribofuranosyl)-1,2-dihydropyrimidin-2-one or 2-pyrimidone-1-β-D-riboside, having a structure represented by the formula immediately below.

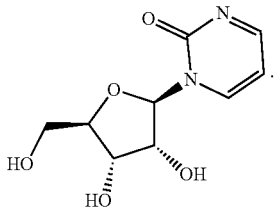 [SMILES: O=c1ncccn1[C@@H]1O[C@H](CO)[C@@H](O)[C@H]1O]

In a further aspect, a DNMT1 inhibitor is a non-nucleoside analogue, including, but not limited to, procainamide, procaine, hydralazine, RG108, and ((−)-epigallocatechin-3-gallate (EGCG).

Procainamide (trade names Pronestyl, Procan, Procanbid) is the compound 4-amino-N-(2-diethylaminoethyl)benzamide having a structure represented by the formula shown immediately below.

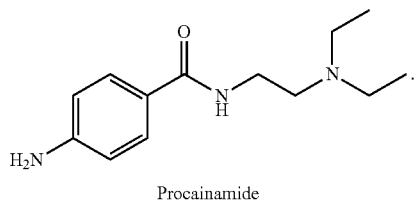 [SMILES: CCN(CC)CCNC(=O)c1ccc(N)cc1]

Procainamide

Procainamide is believed to inhibit the hemimethylase activity of DNA methyltransferase 1 (DNMT1), the mammalian enzyme thought to be responsible for maintaining DNA methylation patterns during replication.

Procaine is the compound 2-(diethylamino)ethyl-4-aminobenzoic acid. Procaine is a DNA-demethylating agent that is understood to inhibit DNA methyltransferases by interfering with enzyme activity having a structure represented by the formula shown immediately below.

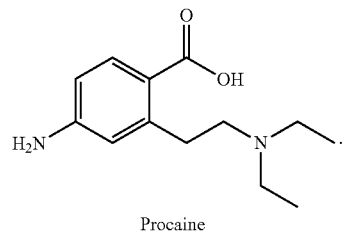 [SMILES: CCN(CC)CCc1cc(N)ccc1C(=O)O]

Procaine

Hydralazine (Apresoline) is the compound 1-hydrazinophthalazine monohydrochloride having a structure represented by the formula shown immediately below.

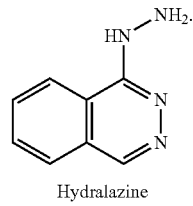

Hydralazine ((−)-Epigallocatechin-3-gallate (EGCG) is a catechin analogue having a structure represented by the formula shown immediately below.

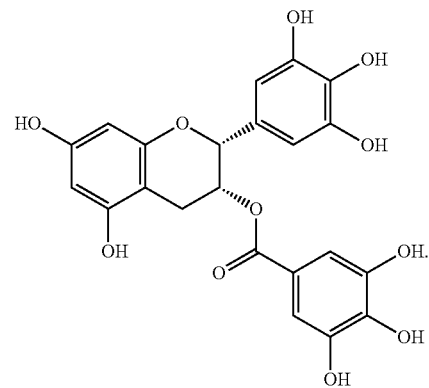 [SMILES: O=C(O[C@@H]1Cc2c(O)cc(O)cc2O[C@@H]1c1cc(O)c(O)c(O)c1)c1cc(O)c(O)c(O)c1]

EGCG is understood to inhibit DNMT activity and reactivate methylation-silenced genes in cancer cells.

RG108, also known as N-phthalyl-1-tryptophan, is the compound (2S)-2-(1,3-dioxoisoindol-2-yl)-3-(1H-indol-3-yl)propanoic acid having a structure represented by the formula shown immediately below.

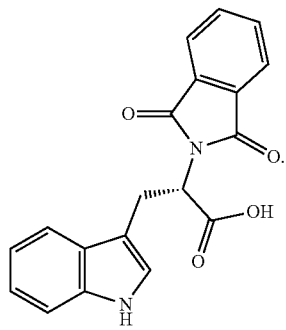

RG108

RG108 is a DNA methyltransferase inhibitor that is understood to inhibit DNA methyltransferases by interfering with enzyme activity.

In a further aspect, a therapeutic agent such as a DNMT1 inhibitor, e.g., at least one 2'-deoxycytidine analog, which can in some aspects be a first therapeutic agent, can be used in combination with one or more other therapeutic agents, which in some instances can be referred to as a second therapeutic agent. In a still further aspect, the further therapeutic agent or the second therapeutic agent can be a disclosed therapeutic agent such as THU, fluorinated THU, or any disclosed therapeutic agent that is associated with reduction or mitigation of the severity or frequency of a sickle pain crisis, such as a vaso-occlusive crisis (VOC) or vaso-occlusive episode (VOE). In a yet further aspect, the further therapeutic agent or the second therapeutic agent can be a disclosed therapeutic agent such as THU, fluorinated THU, or a therapeutic agent that is known to the skilled artisan or as approved by a regulatory agency, e.g., the U.S. Food and Drug Administration or the European Union European Medicines Agency, for clinical use for reduction or mitigation of the severity or frequency of a sickle pain crisis, such as a vaso-occlusive crisis (VOC) or vaso-occlusive episode (VOE). The second therapeutic agent can also be a therapeutic agent that is known to the skilled artisan or as approved by a regulatory agency, e.g., the U.S. Food and Drug Administration or the European Union European Medicines Agency, for clinical use for treatment, prevention, or amelioration of well-known sickle cell complications caused by damaged kidney, gall bladder, liver, lungs, heart, and the like.

In a further aspect, the DNMT1 inhibitor, e.g., at least one 2'-deoxycytidine analog, can optionally be used in combination a second therapeutic agent; and wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity such as Voxelotor (GBT440); AN-233; a P-selectin binder such as, for example, crizanlizumab or inclacumab, a pyruvate kinase M2 activator such as, for example, AG348 or FT-4202; a PDE9 inhibitor such as, for example, IMR-687; a stimulator of soluble guanylate cyclase such as, for example, olinciguat; an anti-hepcidin therapy such as, for example, PGT-300 or siRNA-GalNAc, or the like; an iron chelator such as, for example, desferasirox or deferiprone; and combinations thereof.

In various aspects, the HDAC inhibitor can be any suitable HDAC inhibitor known to inhibit HDAC activity in a subject, including, but not limited to, suberoylanilide hydroxamic acid (SAHA, also marketed as Vorinostat), amide analogues of trichostatin A, hydroxamic acid analogs of trapoxin, and scriptaid (6-(1,3-Dioxo-1H, 3H-benzo[de] isoquinolin-2-yl)-hexanoic acid hydroxyamide) and analogs. In a further aspect, the HDAC inhibitor can be selected from the group consisting of suberoylanilide hydroxamic acid (SAHA), N-hydroxy-7-(4-dimethylaminobenzoyl)-aminoheptanamide (M344), N-hydroxy-8-(4-dimethylaminobenzoyl)-aminooctanamide (M360), N-hydroxy-6-(4-biphenylcarbonyl)-aminocapramide (M355), N-hydroxy-6-(4-dimethylaminobenzoylamino)-capramide (MD85), (S)-octanedioic acid hydroxyamide (1-phenethylcarbamoyl-2-phenyl-ethyl)-amide (SW68), (S)-octanedioic acid hydroxyamide (1-benzylcarbamoyl-2-phenyl-ethyl)-amide (SW70), (S)-3-(4-methoxyphenyl)-2-(7-hydroxycarbamoyl-heptanoylamino)-propionic acid methyl ester (SW99), (S)-2-(7-hydroxycarbamoyl-heptanoylamino)-3-thiophen-2-yl-propionic acid methyl ester (SW86), (S)-3-(4'-chlorobiphenyl-4-yl)-2-(7-hydroxycarbamoylheptanoylamino)-propionic acid methyl ester (SW183), (S)-3-(3', 4'-dichlorobiphenyl-4-yl)-2-(7-hydroxycarbamoylheptanoylamino)-propionic acid methyl ester (SW187), (S)-2-(7-hydroxycarbamoylheptanoylamino)-3-(4-methoxybiphenyl-4-yl)-propionic acid methyl ester (SW188), (S)-2-(7-hydroxycarbamoylheptanoylamino)-3-(4'-methylbiphenyl-4-yl)-propionic acid methyl ester (SW189), (S)-3-(phenyl)-2-(7-hydroxycarbamoyl-heptanoylamino)-propionic acid methyl ester (M232), 6-(1,3-dioxo-1H,3H-benzo[de]isoquinolin-2-yl)-hexanoic acid hydroxyamide (HR13), 6-(4,5,6,7-tetrachloro-1,3-dioxo-1, 3-dihydroisoindol-2-yl) hexanoic acid hydroxyamide (HR10), 6-(1,3-dioxo-1,3-dihydroisoindol-2-yl) hexanoic acid hydroxyamide (HR11), and combinations thereof.

In various aspects, the PD1 inhibitor can be any suitable PD1 inhibitor known to inhibit PD1 activity in a subject, including, but not limited to, pembrolizumab, nivolumab, pidilizumab, lambrolizumab, spartalizumab, cemiplimab, tislelizumab, atezolizumab, avelumab, durvalumab, AK104, AMP-224, AMP-514, AK105, ALN-PDL, AUNP12, BCD-100, BGB108, BGBA317, BGB-A333, BI 754091, BMS-936559, CK-301, FAZ053, JS001, KD033, KY1003, KN035, LZMO09, M7824, MCLA134, MDX-1105, MEDI-4736, MEDI-0680, MGA012, MGD013, MPDL3280A, MSB0010718C, MSB2311, PDROO1, PF-06801591, REGN2810, SHR1210, SHR-1316, Sym021, STIA100X, STIA1010, STIA1011, STIA1012, STIA1014, TSR-042, XmAb20717, and combinations thereof.

In various aspects, the JAK inhibitor can be any suitable JAK inhibitor known to inhibit PD1 activity in a subject, including, but not limited to, abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and/or upadacitinib; combinations thereof and/or pharmaceutically acceptable salts thereof. In a further aspect, the JAK inhibitor can be any suitable JAK inhibitor known to inhibit PD1 activity in a subject, including, but not limited to, ruxolitinib, tofacitinib, oclacitinib, baricitinib, filgotinib, gandotinib, lestaurtinib, momelotinib, pacritinib, PF-04965842, upadacitinib, peficitinib, fedratinib, cucurbitacin I, decernotinib, INCB018424, AC430, BMS-0911543, GSK2586184, VX-509, R348, AZD1480, CHZ868, PF-956980, AG490, WP-1034, JAK3 inhibitor IV, atiprimod, FM-381, SAR20347, AZD4205, ARN4079, NIBR-3049, PRN371, PF-06651600, JAK3i, JAK3 inhibitor 31, PF-06700841, NC1153, EP009, Gingerenone A, JANEX-1, cercosporamide, JAK3-IN-2, PF-956980, Tyk2-IN-30, Tyk2-IN-2, JAK3-IN1, WHI-P97, TG-101209, AZ960, NVP-BSK805, NSC 42834, FLLL32, SD 1029, WIH-P154, WHI-P154, TCS21311, JAK3-IN-1, JAK3-IN-6, JAK3-IN-7, XL019, MS-1020, AZD1418, WP1066, CEP33779, ZM 449829, SHR0302, JAK1-IN-31, WYE-151650, EXEL-8232, solcitinib, itacitinib, cerdulatinib, PF-06263276, delgotinib, AS2553627, JAK-IN-35, ASN-002, AT9283, diosgenin, JAK inhibitor 1, JAK-IN-I, LFM-A13, NS-018, RGB-286638, SB 1317, curcumol, Go6976, JAK2 inhibitor G5-7, myricetin, and/or pyridine 6; combinations thereof and/or pharmaceutically acceptable salts thereof.

In a further aspect, the DNMT1 inhibitor, e.g., at least one 2'-deoxycytidine analog, can optionally be used in combination with a second therapeutic agent such as at least one cytidine deaminase inhibitor ("CDA inhibitor(s)) in the disclosed pharmaceutical compositions. Suitable CDA inhibitors include those as disclosed herein, as well as those described by Ferraris et al, 2014; U.S. Pat. No. 6,136,791; WO2009/052287, which is incorporated herein in its entirety.

In a further aspect, the disclosed CDA inhibitors include, but are not limited to, tetrahydrouridine analogs, such as tetrahydrouridine (THU), fluorinated tetrahydrouridine analogs and derivatives thereof.

Non-limiting examples of suitable fluorinated tetrahydrouridines are 2'-fluorinated tetrahydrouridine derivatives, including, but not limited to, at least one of the following:
2'-Deoxy-2',2'-difluoro-5,6-dihydrouridine;
(4R)-2'-Deoxy-2',2'-difluoro-3,4,5,6-tetrahydrouridine;
(4S)-2'-Deoxy-2',2'-difluoro-3,4,5,6-tetrahydrouridine;
1-(2-Deoxy-2,2-difluoro-β-D-erythro-pentofuranosyl)-tetrahydro-2(1H)-pyrimidinone;
2'-Deoxy-2'-fluoro-5,6-dihydrouridine;
(4R)-2'-Deoxy-2'-fluoro-3,4,5,6-tetrahydrouridine;
(4S)-2'-Deoxy-2'-fluoro-3,4,5,6-tetrahydrouridine;
1-(2-Deoxy-2-fluoro-(3-D-ribofuranosyl)tetrahydro-2(1H)-pyrimidinone;
1-(2-Deoxy-2-fluoro-β-D-arabinofuranosyl)dihydro-2,4-(1H,3H)-pyrimidinedione;
(4R)-1-(2-Deoxy-2-fluoro-(3-D-arabinofuranosyl)tetrahydro-4-hydroxy-2(1H)-pyrimidinone; and/or
(4S)-1-(2-Deoxy-2-fluoro-(3-D-arabinofuranosyl)tetrahydro-4-hydroxy-2(1H)-pyrimidinone.

Further non-limiting examples of suitable fluorinated tetrahydrouridines are difluorotetrahydrouridine derivatives such as 2'-fluoro-2'-deoxytetrahydrouridines derivatives, including, but not limited to, at least one of the following:
2'2'-difluoro-dihydro-uridine (DFDHU);
2'2'-difluoro-tetrahydrouridine (DFTHU);
2'(R)-fluoro-2'deoxy-tetrahydrouridines;
2'(R)-Fluoro-2'deoxy-dihydrouridine ((R)-FDHU);
2'(S)-fluoro-2'deoxy-tetrahydrouridines;
2'(S)-fluoro-2'deoxy-dihydrouridine ((S)-FDHU); and/or
2'(S)-fluoro-2'deoxy-tetrahydrouridine ((S)-FTHU).

In a further aspect, the disclosed CDA inhibitors include, but are not limited to, ASTX727 (E7727); 5-methyl-2',3'-dideoxy-3'-azidocytidine (5mAZC); 5-methyl-2',3'-dideoxycytidine; 5-ethyl-2',3'dideoxy-3'-azidocytidine; 5-propyl-2',3'-dideoxycytidine; 5-propyl-2',3'-dideoxy-3'-azidocytidine; 5-propene-2',3'-dideoxy-3'-azidocytidine; 5-propyne-2',3'-dideoxy-3'-azidocytidine; and 5-propyne-2', 3'-dideoxy-3'-azidocytidine; analogues thereof or a pharmaceutically effective salt thereof, and compounds described in U.S. Pat. No. 6,136,791; and Zebularine (1-(β-D-Ribofuranosyl)-2(1H)-pyrimidinone) (Lemaire et al., 2009; Marquez et al., 2005).

In a further aspect, the therapeutic agent herein can be a fetal hemoglobin inducer ("HbF inducer") for increasing HbF levels in hematopoietic progenitor cells. Suitable HbF inducers for the disclosed compositions and methods include, but are not limited to, at least one inhibitor of DNA methylation, e.g., a DNMT1 inhibitor; and optionally at least one inhibitor of CDA (cytidine deaminase); optionally at least one HDAC (histone deacetylase) inhibitor; optionally at least one PK2 activator; and combinations thereof of the various optional therapeutic agents. The DNMT1 inhibitor, HDAC (histone deacetylase) inhibitor, PK2 activator, or CDA inhibitor can be any such inhibitor as disclosed herein.

Pharmaceutical Compositions.

In various aspects, the present disclosure relates pharmaceutical compositions comprising a therapeutically effective amount of at least one DNMT1 inhibitor, e.g., at least one 2'-deoxycytidine analog, as disclosed herein and at least one pharmaceutically acceptable excipient. In a further aspect, the present disclosure relates pharmaceutical compositions comprising a therapeutically effective amount of at least one DNMT1 inhibitor, e.g., at least one 2'-deoxycytidine analog, as disclosed herein, optionally at least one CDA inhibitor as disclosed herein, and at least one pharmaceutically acceptable excipient. In a yet further aspect, the disclosed pharmaceutical compositions can be an orally available, low dose, fixed dose, delayed release combination product thus providing an easy-to-use product for a patient to use at home.

Heretofore, a pharmaceutical composition for concomitant oral administration of a DNMT1 inhibitor, e.g., 2'-deoxycytidine analog and optionally a CDA inhibitor has not been reported. Conventionally, administration of a DNMT1 inhibitor and/or a CDA inhibitor has been by intravenous administration, which has severe limitations such as lack of use of use by patients at home, increased cost, and requirement for expensive in-patient or hospital treatment. For example, FdCyd and THU have been evaluated in phase II clinical studies that use an IV route of administration. However, oral administration of this combination has not been reported or suggested, and the use of the disclosed pharmaceutical compositions can allow for more prolonged exposure to FdCyd, which is desirable in the disclosed methods of treatment, e.g., hypomethylating therapy. In addition, the disclosed pharmaceutical compositions can significantly improve clinical efficacy of DNMT1 inhibitors with less cytotoxic effects, enable use of low dose of DNMT1 inhibitor to induce HbF, be more convenient by requiring fewer office visits, thereby reducing travel to and waiting in the clinic.

Moreover, a physician needs to be trained to administer existing IV formulations in different doses, sequences and combinations. The present disclosure (orally available, fixed dose, delayed release combination product) reduces the cost of administration, provides a pharmaceutical composition that a subject can use it at home, requires less physician training needed, allows for a fixed dose combination reduces inter-patient variability in therapeutic response, and as an oral formulation it avoids injection making it easier to administer to children or subjects with a phobia of needles.

In a further aspect, the present disclosure relates to pharmaceutical compositions comprising a therapeutically effective amount of at least one disclosed 2'-deoxycytidine analog, or a pharmaceutically acceptable salt thereof, and optionally at least one disclosed CDA inhibitor, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed 2'-deoxycytidine analog, or a pharmaceutically acceptable salt thereof, and optionally at least one disclosed CDA inhibitor, or a pharmaceutically acceptable salt thereof, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a still further aspect, the disclosed pharmaceutical composition can be formulated to allow administration orally.

In various aspects, the present disclosure also relates to a pharmaceutical composition comprising a pharmaceutically acceptable carrier or diluent and, as active ingredient, a therapeutically effective amount of at least one disclosed 2'-deoxycytidine analog, or a pharmaceutically acceptable salt, a hydrate thereof, a solvate thereof, a polymorph thereof, or a stereochemically isomeric form thereof, and optionally, at least one CDA inhibitor, or a pharmaceutically acceptable salt, a hydrate thereof, a solvate thereof, a polymorph thereof, or a stereochemically isomeric form thereof. In a further aspect, at least one disclosed 2'-deoxycytidine analog, or a pharmaceutically acceptable salt, a hydrate thereof, a solvate thereof, a polymorph thereof, or a stereochemically isomeric form thereof, and optionally, at least one disclosed CDA inhibitor, or a pharmaceutically acceptable salt, a hydrate thereof, a solvate thereof, a polymorph thereof, or a stereochemically isomeric form thereof, may be formulated into various pharmaceutical forms for administration purposes.

Pharmaceutical compositions of the present disclosure encompass any composition made by admixing the active ingredients and a pharmaceutically acceptable carrier. The carrier may take a wide variety of forms depending on the form of preparation desired for administration, e.g., oral administration. Thus, the pharmaceutical composition of the invention can be presented as discrete units suitable for oral administration such as capsules, cachets or tablets each containing a predetermined amount of the active ingredients. Further, the composition can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the composition may also be administered by controlled release means and/or delivery devices. The foregoing list is illustrative only and is not intended to be limiting in any way.

Pharmaceutically acceptable salts can be prepared from pharmaceutically acceptable non-toxic bases or acids. For therapeutic use, salts of the disclosed therapeutic agents are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed therapeutic agent comprising an acidic group or moiety, e.g., a carboxylic acid group, can be used to prepare a pharmaceutically acceptable salt. For example, such a disclosed therapeutic agent may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base therapeutic agents are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed therapeutic agent comprising a protonatable group or moiety, e.g., an amino group, can be used to prepare a pharmaceutically acceptable salt. For example, such a disclosed therapeutic agent may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base therapeutic agent are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the therapeutic agents of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the disclosed pharmaceutical compositions in a single dosage form for ease of administration and uniformity of dosage.

The pharmaceutical compositions disclosed herein comprise a therapeutic agent of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present disclosure may be prepared by any of the methods well known in the art of pharmacy. Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The therapeutic agents described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form for the disclosed pharmaceutical compositions, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like. In a further aspect, the pharmaceutically acceptable excipient can be mannitol, microcrystalline cellulose, crospovidone, magnesium stearate, another excipient as disclosed herein, or a combination thereof.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalyethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed therapeutic agent that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated, or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made from Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethylcellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are chelate formers such as ethylene diamine tetraacetic acid, nitrilotriacetic acid, diethylene triamine pentaacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g., 2-hydroxypropyl-β-cyclodextrin or sulfobutyl-β-cyclodextrin. Also, co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

In another aspect, the pharmaceutical composition further includes a coating. In a further aspect, the coating is an enteric coating. In still another aspect, the coating can be a sugarcoating, a film coating, a compression coating, or a combination thereof. In aspects where the coating is a film coating, it can be a cellulose ether polymer such as, for example, a hydroxypropyl methylcellulose, hydroxypropyl cellulose, or methylcellulose polymer or a combination thereof.

Depending on the particular dosage form, a disclosed pharmaceutical composition can comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In a further aspect, the disclosed pharmaceutical composition has a unit dose form comprising from about 0.01 to 1000 mg per kg patient body weight per day of a disclosed therapeutic agent and can be administered in single or multiple doses. In various aspects, the dosage level of a disclosed therapeutic agent will be about 0.1 to about 500 mg/kg per day, about 0.1 to 250 mg/kg per day, or about 0.5 to 100 mg/kg per day. A suitable dosage level of a disclosed therapeutic agent can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day; or from about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16, mg/kg about 17 mg/kg, about 18 mg/kg, about 19 mg/kg, and/or about 20 mg/kg. In an aspect, the prior listing of doses from about 1 to about 20 mg/kg includes any range therein, for example, from about 2 to about 8 mg/kg. For oral administration, the disclosed pharmaceutical compositions can be provided in the form of tablets containing a disclosed therapeutic agent of from about 1.0 to about 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. In one aspect, the tablets contain 40, 400, or 1000 mg of a disclosed therapeutic agent. The unit dose form can be administered on a regimen of 1 to 4 times per day, preferably once or twice per day. The unit dose form can be adjusted to provide the optimal therapeutic response. In a still further aspect, the unit dose form is administered once per week or is administered 2-3 times per week.

Disclosed unit doses as described can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular subject will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical unit dose can be taken once a day, or can be taken multiple times per day, or can be one time-release capsule or tablet taken once a day and containing a proportionally higher content of active ingredient. Alternatively, the unit dose can be taken once per week or 2-3 times per week. The time-release effect can be obtained by capsule materials that dissolve at different pH values, by capsules that release slowly by osmotic pressure, or by any other known means of controlled release.

In a further aspect, the disclosed pharmaceutical composition has a unit dose form comprising at least one 2'-deoxycytidine analog from about 1 to about 60 mg, or at least one 2'-deoxycytidine analog from about 1.5 to about 15 mg, or at least one 2'-deoxycytidine analog in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 mg, or a combination of any of the foregoing values, or a range encompassing any of the foregoing values. In a still further aspect, the foregoing pharmaceutical composition is formulated for oral administration.

a further aspect, the disclosed pharmaceutical composition has a unit dose form comprising at least one 2'-deoxycytidine analog of from about 1 to 600 mg per m² patient body surface area per day and can be administered in single or multiple doses. In various aspects, the dosage level will be about 1 to about 500 mg/m² per day, about 1 to 250 mg/m² per day, or about 1 to 150 mg/m² per day. A suitable dosage level can be about 1 to 600 mg/m² per day, about 1 to 250 mg/m² per day, about 1 to 150 mg/m² per day, about 1 to 100 mg/m² per day, or about 1 to 50 mg/m² per day. Within this range the dosage can be 1 to 50, 50 to 100, 100 to 150, 150 to 250, or 250 to 500 mg/m² per day. In a still further aspect, the disclosed pharmaceutical composition has a unit dose form comprising at least one 2'-deoxycytidine analog of from about 5 mg/m² to about 135 mg/m², or can be about 5, 10, 15, 20, 25, 30, 35, 40, 45, 50, 55, 60, 65, 70, 75, 80, 85, 90, 95, 100, 105, 110, 115, 120, 125, 130, or about 135 mg/m², or a combination of any of the foregoing values, or a range encompassing any of the foregoing values. In one aspect the dose of the cytidine analog is 134 mg/m².

In a further aspect, a disclosed pharmaceutical composition comprises at least one 2'-deoxycytidine analog in a unit dose that can be administered more than once a day, for example, 2, 3, 4, 5 or 6 times a day. In various aspects, a disclosed pharmaceutical composition comprises at least one 2'-deoxycytidine analog in a unit dose that can be administered 1 or 2 times per day, so that the total dosage for a 70 kg adult is in the range of 0.001 to about 15 mg per kg weight of subject per administration. In a further aspect, a disclosed pharmaceutical composition comprises at least one 2'-deoxycytidine analog in a unit dose that is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

In a further aspect, the disclosed pharmaceutical composition has a unit dose form comprising at least one 2'-deoxycytidine analog that when administered to a subject provides an area-under-the-curve value for the at least one 2'-deoxycytidine of from about 100 ng·hr/mL to about 400 ng·hr/mL, or of about 100, 150, 200, 225, 250, 275, 300, 325, 350, 375, or about 400 ng·hr/mL, or a combination of any of the foregoing values, or a range encompassing any of the foregoing values. In a still further aspect, the foregoing pharmaceutical composition is formulated for oral administration.

In a further aspect, the disclosed pharmaceutical composition has a unit dose form comprising at least one 2'-deoxycytidine analog that when administered to a subject a maximum plasma concentration of the at least one 2'-deoxycytidine analog from about 0.005 to about 0.05 µM following administration to the subject, or of about 0.005, 0.005, 0.01, 0.025, or about 0.05 µM, or a combination of any of the foregoing values, or a range encompassing any of the foregoing values. In another aspect, the disclosed pharmaceutical composition has a unit dose form comprising at least one 2'-deoxycytidine analog that when administered to a subject achieves a maximum plasma concentration at from about 60 minutes to about 180 minutes following administration to a subject, or at about 60, 75, 90, 105, 120, 135, 150, 165, or about 180 minutes following administration to a subject, or a combination of any of the foregoing values, or a range encompassing any of the foregoing values. In a still further aspect, the foregoing pharmaceutical composition is formulated for oral administration.

In one aspect, the disclosed pharmaceutical compositions optionally comprise a disclosed CDA inhibitor such as, for example, tetrahydrouridine, is administered by intravenous infusion or subcutaneous injection or the like, wherein the CDA inhibitor can be administered in a dosage of from about 10 to about 500 mg/m² of body surface area, or at about 10, 25, 50, 75, 100, 150, 200, 250, 300, 350, 400, 450, or about 500 mg/m² of body surface area, or a combination of any of the foregoing values, or a range encompassing any of the foregoing values.

In a further aspect, the disclosed pharmaceutical compositions optionally comprise a disclosed CDA inhibitor that is administered in tablet or capsule form, wherein the CDA inhibitor is administered in dosage of from about 1 to about 400 mg/kg of body weight, or at about 1, 5, 10, 15, 20, 25, 50, 75, 100, 125, 150, 175, 200, 225, 250, 275, 300, 325, 350, 375, or about 400 mg/kg of body weight, or a combination of any of the foregoing values, or a range encompassing any of the foregoing values.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

In a further aspect, the disclosed pharmaceutical composition can have a unit dose form comprising a therapeutically effective amount of at least one tetrahydrouridine analog for treating a subject. In a still further aspect, the disclosed pharmaceutical composition has a unit dose form comprising at least one tetrahydrouridine analog at a therapeutically effective dose of from about 100 to about 600 mg/m² or can be about 100, 150, 200, 250, 300, 350, 400, 450, 500, 550, or about 600 mg/m², or a combination of any of the foregoing values, or a range encompassing any of the foregoing values. In a yet further aspect, the disclosed pharmaceutical composition has a unit dose form comprising at least one tetrahydrouridine analog at a therapeutically effective dose of from about 50 to about 350 mg/m², or can be about 50, 100, 150, 200, 250, 300, or about 350 mg/m², or a combination of any of the foregoing values, or a range encompassing any of the foregoing values. In one aspect, the combinatorial compositions disclosed herein can include 145 mg/m² cytidine analog and 350 mg/m² tetrahydrouridine.

In a still further aspect, the disclosed pharmaceutical composition can have a unit dose form comprising at least one tetrahydrouridine analog that when administered to a subject is bioavailable from about 1 to about 180 minutes, or from about 15 to about 60 minutes, before at least one 2'-deoxycytidine analog, or about 15, 30, 45, 60, 75, 90, 105, 120, 135, 150, 165, or about 180 minutes before the at least one 2'-deoxycytidine analog, or a combination of any of the foregoing values, or a range encompassing any of the foregoing values. In a yet further aspect, the at least one tetrahydrouridine analog is not acid stable and is encapsulated in an enteric coating in the formulations disclosed herein in order to preserve its activity when administered to the subject. In a further aspect, the enteric coating can be formulated such that extended release of at least one tetrahydrouridine analog is possible by means such as, for example, microencapsulation, embedding in a matrix of a single layer or of different layers, or the like.

In various aspects, the disclosed pharmaceutical compositions can be oral formulations comprising both a 2'-deoxycytidine analog and optionally a therapeutic agent to inhibit cytidine deaminase. It is believed that a cytidine deaminase can inhibit rapid conversion of 2'-deoxycytidine analogs to unwanted less-effective metabolites. For example, a cytidine deaminase can inhibit metabolism of 5-fluoro-2'-deoxycytidine to metabolites such as 5-fluoro-2'-deoxyuridine, 5-fluorouracil, and 5-fluorouridine. Without wishing to be bound by a particular theory, it is believed that 5-fluoro-2'-deoxyuridine, 5-fluorouracil, and 5-fluorouridine do not effectively inhibit DNMT1. In one aspect, this phenomenon can lead to increased exposure to the cytidine analogs and decreased exposure to the ineffective metabolites.

In a further aspect, the disclosed pharmaceutical compositions can be a pharmaceutical composition for oral administration comprising at least one 2'-deoxycytidine analog as disclosed herein including, but not limited to, 5-fluoro-2'-deoxycytidine, and optionally at least one CDA inhibitor, including, but not limited to, a tetrahydrouridine derivative such as, for example, a 2'-fluorinated tetrahydrouridine derivative.

In another aspect, the disclosed pharmaceutical composition is formulated such that the optional tetrahydrouridine or tetrahydrouridine derivative is released more quickly than the cytidine analog. In one aspect, "differential release" or "dual release" as used herein refers to the release at different time points of two or more active ingredients from a formulation containing more than one active ingredient or drug. In a further aspect, "differential" and "dual release" also refer to bioavailability of two or more active ingredients at different time points after administration by ingestion or other means.

As used herein, "bioavailable" refers to absorption and use by the body of an active ingredient in a pharmaceutical. Thus, an "orally bioavailable" drug can be taken by mouth and absorbed without being destroyed in the digestive tract. In one aspect, the pharmaceutical compositions disclosed herein can produce at least about 10-fold improvement in the oral bioavailability of cytidine analog and optional tetrahydrouridine analog. In a further aspect, the pharmaceutical compositions exhibit low $C_{max}$ and a multi-hour $T_{max}$, thus resulting in non-cytotoxic DNMT1 depletion by the cytidine analog. In a further aspect, the pharmaceutical compositions can result in peak cytidine analog concentrations of from about $0.05 \mu m$ to about $0.5 \mu m$ in a human subject, or of about 0.05, 0.1, 0.15, 0.2, 0.25, 0.3, 0.35, 0.4, 0.45, or about $0.5 \mu m$ in a human subject, or a combination of any of the foregoing values, or a range encompassing any of the foregoing values.

In one aspect, in order to accomplish differential release with faster release of the optional tetrahydrouridine or a tetrahydrouridine analog, the tetrahydrouridine or analog can be located at the surface of an oral administration form such as a tablet, for example, as an outer layer. In an alternative aspect, binders, excipients, fillers, coatings, and the like, can be formulated to allow for different dissolution rates for the tetrahydrouridine or analog as opposed to the cytidine analog. Further in this aspect, the cytidine analog can be located at the center of an oral administration form, or the binders, excipients, fillers, coatings, and the like for the cytidine analog portion of the oral administration form can be formulated to allow for a slower dissolution rate. In a further aspect, the cytidine analog can be coated with or embedded in a polymer to facilitate delayed release. In one aspect, the tetrahydrouridine or tetrahydrouridine analog is bioavailable from about 1 minute to about 180 minutes before the cytidine analog, or from about 15 minutes to about 60 minutes before the cytidine analog, or from about 30 minutes to about 60 minutes before the cytidine analog, or about 1, 5, 10, 15, 20, 25, 30, 35, 40, 45, 50, 55, 60, 70, 80, 90, 100, 110, 120, 130, 140, 150, 160, 170, or about 180 minutes before the cytidine analog, or a combination of the foregoing values, or a range encompassing any of the foregoing values. In an alternative aspect, the tetrahydrouridine or tetrahydrouridine analog can be formulated in a separate dosage form (e.g., pill, tablet, capsule, etc.) from the cytidine analog, which can be administered separately. In a further aspect, the active ingredients disclosed herein can be packaged in microspheres and/or microparticles, including microspheres and/or microparticles having different matrices with different dissolution rates such that delayed release is facilitated.

In a further aspect, delayed release can be accomplished with a matrix or coating that includes or consists of a poorly soluble polymer. In a further aspect, the poorly soluble polymer can be polyvinyl chloride, polyethylene, a vinyl polymer or copolymer, hydroxypropyl methyl cellulose, shellac, ammoniated shellac, shellac-acetyl alcohol, shellac n-butyl stearate, copolymers of acrylic and methacrylic acid esters having low content of quaternary ammonium groups, and combinations thereof. In a further aspect, the vinyl polymers and/or copolymers can be polyvinyl pyrrolidone, polyvinyl acetate, polyvinylacetate phthalate, vinylacetate crotonic acid copolymer, ethylene-vinyl acetate copolymer, and combinations thereof.

In a further aspect, the disclosed pharmaceutical compositions can comprise at least one 2'-deoxycytidine analog and at least one fetal hemoglobin expression inducer, and optionally at least one tetrahydrouridine analog. In a further aspect, the disclosed pharmaceutical composition can comprise at least one 2'-deoxycytidine analog and at least one fetal hemoglobin inducer, and at least one tetrahydrouridine analog.

Methods for Treating a Hematological Disorder.

In one aspect, disclosed herein is a method for treating a hematological disorder in a subject, the method comprising administering a therapeutically effective amount of a disclosed pharmaceutical composition or a disclosed therapeutic agent to a subject. In a further aspect, the method comprises administering a therapeutically effective amount of a disclosed pharmaceutical composition comprising a 2'-deoxycytidine analog. In a still further aspect, the method comprises administering a disclosed pharmaceutical composition comprising a therapeutically effective amount of comprising a 2'-deoxycytidine analog and optionally a therapeutically effective amount of a CDA inhibitor. In a yet further aspect, the method comprises administering a therapeutically effective amount of at least one disclosed 2'-deoxycytidine analog. In an even further aspect, the method comprises administering a therapeutically effective amount of at least one 2'-deoxycytidine analog, and optionally a therapeutically effective amount of at least one CDA inhibitor.

In various aspects, the disclosed methods comprise treating a hematological disorder in a subject, the method comprising administering a therapeutically effective amount of a compound of a first therapeutic agent, an optional second therapeutic agent, and at least one pharmaceutically acceptable excipient; wherein the first therapeutic agent is 5-aza-4'-thio-2'-deoxycytidine, 5-fluoro-2'-deoxycytidine, a pharmaceutically acceptable salt thereof, or combinations thereof; and wherein the second therapeutic agent is a therapeutic agent disclosed herein, a pharmaceutically acceptable salt thereof, or combinations thereof.

In a further aspect, the method for treating a hematological disorder further comprises the step of identifying a subject having a hematological disorder. In a yet further aspect, the subject in the method for treating a hematological disorder has already been identified as having a hematological disorder. In a still further aspect, the hematological disorder can be sickle cell disease or thalassemia.

In a further aspect, the method for treating a hematological disorder comprises administering a therapeutically effective amount of a 2'-deoxycytidine analog of from about 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values. In a still further aspect, In a further aspect, the method for treating a hematological disorder comprises administering a therapeutically effective amount of a 2'-deoxycytidine analog of from about 5 mg/m$^2$ to about 135 mg/m$^2$, or can be about 5, 10, 15, 20, 25, 30, 35, 40, 45, 50, 55, 60, 65, 70, 75, 80, 85, 90, 95, 100, 105, 110, 115, 120, 125, 130, or about 135 mg/m$^2$, or a combination of any of the foregoing values, or a range encompassing any of the foregoing values. In a yet further aspect, the dose of the cytidine analog is 134 mg/m$^2$.

In a further aspect, the method for treating a hematological disorder optionally further comprises administering a therapeutically effective amount of a CDA inhibitor, e.g., a tetrahydrouridine analog, to the subject. In a still further aspect, the therapeutically effective amount of the tetrahydrouridine analog, when optionally included as a step in the disclosed method for treating a hematological disorder, can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In a yet further aspect, the therapeutically effective amount of the optionally included tetrahydrouridine analog can be from about 50 to about 350 mg/m$^2$, or can be about 50, 100, 150, 200, 250, 300, or about 350 mg/m$^2$, or a combination of any of the foregoing values, or a range encompassing any of the foregoing values. In one aspect, the pharmaceutical compositions disclosed herein can include 145 mg/m$^2$ cytidine analog and optionally 350 mg/m$^2$ tetrahydrouridine.

In a further aspect, tetrahydrouridine is optionally administered before administering the 2'-deoxycytidine analog, concurrently with the 2'-deoxycytidine analog, or after the 2'-deoxycytidine analog. In any of these aspects, the tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a further aspect, tetrahydrouridine is not administered to the subject. In a further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

Methods for Increasing Fetal Hemoglobin Expression.

In one aspect, disclosed herein is a method for increasing fetal hemoglobin expression in a subject, the method comprising administering a therapeutically effective amount of a disclosed pharmaceutical composition or a disclosed therapeutic agent to a subject. In a further aspect, the method comprises administering a therapeutically effective amount of a disclosed pharmaceutical composition comprising at least one DNMT1 inhibitor, e.g., at least one, 2'-deoxycytidine analog and at least one HbF inducer. In a still further aspect, the method comprises administering a pharmaceutical composition comprising a therapeutically effective amount of a disclosed pharmaceutical composition comprising at least one DNMT1 inhibitor, e.g., at least one 2'-deoxycytidine analog, at least on HbF inducer, and optionally at least one CDA inhibitor. In a yet further aspect, the method comprises administering a therapeutically effective amount of at least one DNMT1 inhibitor, e.g., at least one 2'-deoxycytidine analog and at least one HbF inducer. In an even further aspect, the method comprises administering a therapeutically effective amount of at least one DNMT1 inhibitor, e.g., at least one 2'-deoxycytidine analog, a therapeutically effective amount of at least one HbF inducer, and optionally a therapeutically effective amount of at least one CDA inhibitor.

In various aspects, the disclosed methods comprise increasing fetal hemoglobin expression in a subject, the method comprising administering a therapeutically effective amount of a compound of a first therapeutic agent, an optional second therapeutic agent, and at least one pharmaceutically acceptable excipient; wherein the first therapeutic agent is 5-aza-4'-thio-2'-deoxycytidine, 5-fluoro-2'-deoxycytidine, a pharmaceutically acceptable salt thereof, or combinations thereof; and wherein the second therapeutic agent is a therapeutic agent disclosed herein, a pharmaceutically acceptable salt thereof, or combinations thereof.

In a further aspect, the method for increasing fetal hemoglobin expression further comprises the step of identifying a subject having a need for increasing fetal hemoglobin expression. In a yet further aspect, the subject in the method for increasing fetal hemoglobin expression has already been identified as having a need for increasing fetal hemoglobin expression.

In a further aspect, the need for increasing fetal hemoglobin expression is associated with a hemoglobinopathy. In a still further aspect, the method further comprises the step of identifying a subject having a hemoglobinopathy. In a yet further aspect, the subject has already been identified as having a hemoglobinopathy. In an even further aspect, the hemoglobinopathy is associated with sickle cell disease or thalassemia.

In a further aspect, the method for increasing fetal hemoglobin expression comprises administering a therapeutically effective amount of at least one DNMT1 inhibitor, e.g., at least one 2'-deoxycytidine analog, of from about 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values. In a still further aspect, In a further aspect, the method for increasing fetal hemoglobin expression comprises administering a therapeutically effective amount of at least one DNMT1 inhibitor, e.g., at least one 2'-deoxycytidine analog, of from about 5 mg/m$^2$ to about 135 mg/m$^2$, or can be about 5, 10, 15, 20, 25, 30, 35, 40, 45, 50, 55, 60, 65, 70, 75, 80, 85, 90, 95, 100, 105, 110, 115, 120, 125, 130, or about 135 mg/m$^2$, or a combination of any of the foregoing values, or a range encompassing any of the foregoing values. In a yet further aspect, the dose of the cytidine analog is 134 mg/m2.

In a further aspect, the method for increasing fetal hemoglobin expression comprises administering a therapeutically effective amount of at least one DNMT1 inhibitor, e.g., at least one 2'-deoxycytidine analog, of from 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values.

In a further aspect, the HbF inducer comprises one or more epigenetic modifiers as described herein can be administered in a therapeutically effective or therapeutically synergistic amount. As used herein, a "therapeutically-effective amount" is an amount such that coadministration of the one or more DNMT1 inhibitors and the one or more HbF inducers (which can include epigenetic modifiers), or administration of a single therapeutic composition or formulation including both classes of drug, as described herein, results in an increase or upregulation of HbF, or results in inhibition of a blood disorder as disclosed herein, or both. Meanwhile, as used herein, a "therapeutically synergistic amount" is the amount of one or more DNMT1 inhibitors and the one or more HbF chemical inducers necessary to significantly reduce or eliminate conditions or symptoms associated with a blood disorder as disclosed herein, and/or to increase or upregulate HbF levels.

In a further aspect, the at least one HbF chemical inducer can be an epigenetic modifier such as, for example, at least one DNA methylation inhibitor, at least one histone deacetylase (HDAC) inhibitor, at least one DNA methylation inhibitor, at least one PK2 inhibitor, or a combination thereof, that can increase HbF levels in hematopoietic progenitor cells. In a further aspect, the DNA methylation inhibitor can be 5-aza-2'-deoxycytidine. In another aspect, the HDAC inhibitor can be selected from suberoylanilide hydroxamic acid (SAHA, also marketed as Vorinostat), amide analogues of trichostatin A, hydroxamic acid analogs of trapoxin, and scriptaid (6-(1,3-Dioxo-1H, 3H-benzo[de]isoquinolin-2-yl)-hexanoic acid hydroxyamide) and analogs.

In a further aspect, a first pharmaceutical composition can comprise a DNMT1 inhibitor, and a second pharmaceutical composition can comprise a HbF chemical inducer, and the first and second pharmaceutical compositions can be co-administered. Coadministration can be sequentially or simultaneously.

In a further aspect, the method for increasing fetal hemoglobin expression further comprises optionally administering a therapeutically effective amount of a CDA inhibitor, e.g., a tetrahydrouridine analog, to the subject. In a still further aspect, the therapeutically effective amount of the optional tetrahydrouridine analog can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In a yet further aspect, the therapeutically effective amount of the optional tetrahydrouridine analog can be from about 50 to about 350 mg/m$^2$, or can be about 50, 100, 150, 200, 250, 300, or about 350 mg/m$^2$, or a combination of any of the foregoing values, or a range encompassing any of the foregoing values. In one aspect, the combinatorial compositions disclosed herein can include 145 mg/m$^2$ cytidine analog and optionally 350 mg/m$^2$ tetrahydrouridine.

In a further aspect, the method further comprises optionally administering a therapeutically effective amount of tetrahydrouridine analog to the subject. In one aspect, the therapeutically effective amount of optionally administered tetrahydrouridine can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In any of these aspects, the tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a further aspect, tetrahydrouridine is not administered to the subject. In a further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In a further aspect, tetrahydrouridine is optionally administered before administering the 2'-deoxycytidine analog, concurrently with the 2'-deoxycytidine analog, or after the 2'-deoxycytidine analog. In any of these aspects, the tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a still further aspect, tetrahydrouridine is not administered to the subject. In a yet further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In one aspect, method for increasing total hemoglobin or fetal hemoglobin expression in a subject can comprise administration of an additional therapeutic agent such as a AN-233 a prodrug conjugate of butyric acid (BA) and δ-aminolevulinate (ALA), Janus kinase (JAK) inhibitor, hydroxyurea, a hemoglobin oxygen-affinity modulator such as, for example, voxelotor sold under the trade name OXBRYTA®, luspatercept sold under the trade name REBLOZYL®, a P-selectin binder such as, for example, crizanlizumab or inclacumab, a pyruvate kinase M2 activator such as, for example, AG348 or FT-4202, a PDE9 inhibitor such as, for example, IMR-687, an HDAC inhibitor, a stimulator of soluble guanylate cyclase such as, for example, olinciguat, an anti-hepcidin therapy such as for example, PGT-300 or siRNA-GalNAc, or the like. In another aspect, the additional therapy can be an iron chelator such as, for example, desferasirox (sold under the trade name EXIADE®) or deferiprone (sold under the trade name FERRIPROX®. In still another aspect, the additional therapy can be a gene therapy product including, but not limited to, ZYNTEGLO®, ARU-1801, EDIT-301, ST-400, CTX001, ET-01, or a combination thereof.

In another aspect, method for increasing total hemoglobin or fetal hemoglobin expression includes administration of an activator of erythrocyte pyruvate kinase-R (PKR), i.e., a PKR activator compound. Pyruvate kinase R (PKR) is the isoform of pyruvate kinase expressed in RBCs and is a key enzyme in glycolysis. The PKR activator can be a compound having an $AC_{50}$ value of less than 1 µM using a suitable assay as known to the skilled artisan (e.g., see the Luminescence Assay in Example 2 in U.S. Pat. Publ. 2022/0031671), In a further aspect, a suitable PKR activator is Etavopival (also known as FT-4202), i.e., the compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)yl)-3-hydroxy-2-phenylpropan-1-one, or a stereoisomer thereof, or a pharmaceutically acceptable salt and/or other solid form thereof, as shown below:

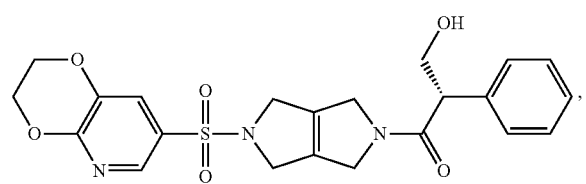 [SMILES: O=C([C@H](CO)c1ccccc1)N1CC2=C(C1)CN(S(=O)(=O)c1cnc3c(c1)OCCO3)C2]

In a further aspect, a suitable PKR activator can be selected from one or more of the compounds disclosed in FIG. 1 of U.S. Pat. Publ. 2022/0031671.

In a further aspect, a suitable PKR activator is mitapivat, i.e., the compound N-[4-[4-(cyclopropylmethyl)piperazine-1-carbonyl]phenyl]quinoline-8-sulfonamide, or a pharmaceutically acceptable salt and/or other solid form thereof, as shown below:

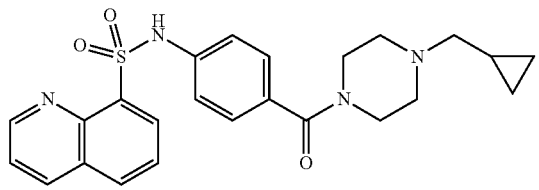 [SMILES: O=C(c1ccc(NS(=O)(=O)c2cccc3cccnc23)cc1)N1CCN(CC2CC2)CC1]

In a further aspect, a suitable PKR activator is rucaparib (AG-014699, PF-01367338), or a pharmaceutically acceptable salt and/or other solid form thereof, as shown below:

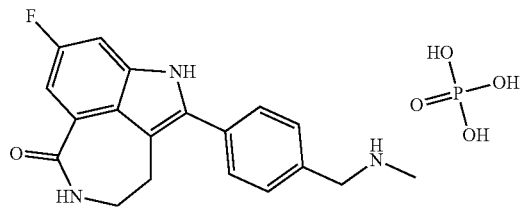 [SMILES: CNCc1ccc(-c2[nH]c3cc(F)cc4c3c2CCNC4=O)cc1 ; O=P(O)(O)O]

In a further aspect, method for increasing total hemoglobin or fetal hemoglobin expression includes administration of a proton pump inhibitor, e.g., famotidine or omeprazole. In a still further aspect, the proton pump inhibitor is selected from the group consisting essentially of omeprazole, lansoprazole, esomeprazole, rabeprazole, pantoprazole, pariprazole, tenatoprazole, leminoprazole, hydroxyomeprazole, dontoprazole, habeprazole, periprazole, or a free base, free acid, salt, hydrate, ester, amide, enantiomer, isomer, tautomer, polymorph, prodrug thereof, and combinations thereof.

In one aspect, method for increasing total hemoglobin or fetal hemoglobin expression in a subject can comprise administration of an Gardos channel blocker selected from the group consisting of imidazole antimycotics, clotrimazole, metronidazole, econazole, arginine, Tram-34, harybdotoxin, nifedipine, 2,2-Bis(4-fluorophenyl)-N-methoxy-2-phenylacetamidine, 2-(2-Chlorophenyl)-2,2-diphenylacetaldehyde oxime, 2-(2-Chlorophenyl)-2,2-bis(4-fluorophenyl)-N-hydroxyacetamidine, 2,2,2-Tris(4-fluorophenyl)-N-hydroxyacetamidine, 2-(2-Fluorophenyl)-2-(4-fluorophenyl)-N-hydroxy-2-phenylacetamidine, phosphoric acid 3-(2-oxazolyl)-4-[3-(trifluoromethyl)phenylsulfonamido]phenyl monoester, N-[2-(4,5-Dihydrooxazol-2-yl)phenyl]-3-(trifluoromethyl)benzenesulfonamide, N-[4-Methoxy-2-(2-oxazolyl)phenyl]benzene sulfonamide, N-[4,5-Dimethoxy-2-(3-methyl-1,2,4-oxadiazol-5-yl)phenyl]-3-(trifluoromethyl)benzenesulfon-amide, N-[2-(2-Furyl)phenyl]-3-(trifluoromethyl)benzenesulfonamide, N-[4-Methyl-2-(2-oxazolyl)phenyl]-3-(trifluoromethyl) benzenesulfonamide and senicapoc, preferably senicapoc or Tram-34.

In various aspects, also disclosed herein are methods for increasing the amount of fetal hemoglobin in the blood of a subject, the method including the steps of administering to a subject (a) a therapeutically effective amount of a 2'-deoxycytidine analog as disclosed herein and optionally, (b) a therapeutically effective amount of tetrahydrouridine.

In a further aspect, the cytidine analog and the optional tetrahydrouridine can be packaged in two separate dosage forms and administered simultaneously. In another aspect, the optional tetrahydrouridine is administered before or after the cytidine analog. In yet another aspect, the cytidine analog and the optional tetrahydrouridine are packaged in the same dosage form. Further in this aspect, the dosage form can be an oral dosage form such as, for example, a layered tablet, a tablet-in-tablet, a tablet-in-capsule, or a capsule-in-capsule. In any of these aspects, the dosage form enables fast release of the tetrahydrouridine and delayed release of the cytidine analog.

In a further aspect, the method further includes step (c) or administering an additional chemotherapeutic agent to the subject. In one aspect, the additional chemotherapeutic agent can be an anti-metabolite, hydroxyurea, decitabine, a prokineticin 2 activator, irinotecan, doxorubicin, a histone deacetylase inhibitor, an anti-viral agent, an anti-retroviral agent, or a combination thereof.

In a further aspect, the cytidine analog and optional tetrahydrouridine are packaged in a first dosage form and the additional chemotherapeutic agent is packaged in a second dosage form. In one aspect, the first dosage form can be administered before, after, or simultaneously with the second dosage form. In other aspects, the cytidine analog, optimal tetrahydrouridine, and additional chemotherapeutic agent are packaged in the same dosage form, which can be, In a further aspect, a layered tablet, a tablet-in-tablet, a tablet-in-capsule, a capsule-in-capsule, or another dosage form. In any of these aspects, a single dosage form can be prepared in order to enable fast release of optional tetrahydrouridine and delayed release of the cytidine analog and additional chemotherapeutic agent. In one aspect, the additional chemotherapeutic agent can be 5-aza-4'-thio-2'-deoxycytidine or a combination of 5-aza-4'-thio-2'-deoxycytidine and tetrahydrouridine.

In any of these aspects, after administration of the formulations disclosed herein to a subject in need thereof, fetal hemoglobin level in the blood of the subject increases to at least 5, 7.5, 10, 12.5, 15, 17.5, or 20%, or a combination of any of the foregoing values, or a range encompassing any of the foregoing values, compared to fetal hemoglobin levels in the subject prior to treatment. In another aspect, prior to performance of the method, the subject can have a fetal hemoglobin level of less than 1 g/dL, whereas after the performance of the method, the subject can have a fetal plus total hemoglobin level of greater than 1 g/dL. In a further aspect, the fetal plus total hemoglobin level remains greater than 1 g/dL for at least 6 months.

Methods for Treating a Disease Associated with Abnormal Cell Proliferation.

In one aspect, disclosed herein is a method for treating a disease associated with abnormal cell proliferation in a subject, the method comprising administering a therapeutically effective amount of a disclosed pharmaceutical composition to a subject, e.g., a disclosed pharmaceutical composition comprising a 2'-deoxycytidine analog. In a further aspect, the disease associated with abnormal cell proliferation can be bladder cancer, breast cancer, brain cancer, an endocrine cancer, retinoblastoma, cervical cancer, colon cancer, rectal cancer, endometrial cancer, renal cell carcinoma, renal pelvis carcinoma, Wilms tumor, a cancer of the oral cavity, liver cancer, gall bladder cancer, cholangiocarcinoma, melanoma, mesothelioma, myelodysplastic syndrome, acute myelogenous leukemia, non-small cell lung cancer, basal cell skin cancer, squamous cell skin cancer, ovarian cancer, pancreatic cancer, prostate cancer, soft tissue sarcoma, osteosarcoma, small cell lung cancer, thyroid cancer, or a combination thereof. In a still further aspect, the method further comprises the step of identifying a subject having an abnormal cell proliferation. In a yet further aspect, the subject has already been identified as having an abnormal cell proliferation.

In a further aspect, the method comprises administering a therapeutically effective amount of a 2'-deoxycytidine analog can be from about 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values.

In a further aspect, the method further comprises optionally administering a therapeutically effective amount of tetrahydrouridine analog to the subject. In one aspect, the therapeutically effective amount of optionally administered tetrahydrouridine can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In one aspect, tetrahydrouridine is optionally administered before administering the 2'-deoxycytidine analog, concurrently with the 2'-deoxycytidine analog, or after the 2'-deoxycytidine analog. In any of these aspects, the optionally administered tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a further aspect, tetrahydrouridine is not administered to the subject. In a further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In a further aspect, the method disclosed herein can be administered in combination with an additional therapy including, but not limited to, surgery, radiation, chemotherapy, or a combination thereof. In a further aspect, chemotherapy can include administering a cytotoxic compound to the subject. In a further aspect, the cytotoxic compound can be an anti-metabolite, hydroxyurea, decitabine, a prokineticin 2 activator, irinotecan, doxorubicin, a histone deacetylase inhibitor, an anti-viral agent, an anti-retroviral agent, or a combination thereof. In any of these aspects, the additional therapy can be administered before, during, or after the method disclosed herein.

In one aspect, the additional therapy can be a PD1 inhibitor, a Janus kinase (JAK) inhibitor, hydroxyurea, a DNMT1 inhibitor, a hemoglobin oxygen-affinity modulator such as, for example, voxelotor sold under the trade name OXBRYTA®, luspatercept sold under the trade name REBLOZYL®, a P-selectin binder such as, for example, crizanlizumab or inclacumab, a pyruvate kinase M2 activator such as, for example, AG348 or FT-4202, a PDE9 inhibitor such as, for example, IMR-687, an HDAC inhibitor, a stimulator of soluble guanylate cyclase such as, for example, olinciguat, an anti-hepcidin therapy such as for example, PGT-300 or siRNA-GalNAc, or the like. In another aspect, the additional therapy can be an iron chelator such as, for example, desferasirox (sold under the trade name EXIADE®) or deferiprone (sold under the trade name FERRIPROX®. In still another aspect, the additional therapy can be a gene therapy product including, but not limited to, ZYNTEGLO®, ARU-1801, EDIT-301, ST-400, CTX001, ET-01, or a combination thereof.

Product for Use in the Treatment of a Disease or Disorder.

In one aspect, disclosed herein are products for use in the treatment of a disease or disorder; the product comprising (a) a first therapeutic agent and optionally a second therapeutic agent; wherein the first therapeutic agent is a compound of Formula I, a pharmaceutically acceptable salt thereof, or combinations thereof; and wherein, when present, the optional second therapeutic agent is tetrahydrouridine, a 2'-fluorinated tetrahydrouridine derivative, a pharmaceutically acceptable salt thereof, or combinations thereof; or (b) a disclosed pharmaceutical composition. In a further aspect, the product comprises a therapeutically effective amount of a disclosed pharmaceutical composition comprising a 2'-deoxycytidine analog.

In a further aspect, disclosed herein are products for use in the treatment of a hematological disorder; the product comprising (a) a first therapeutic agent and optionally a second therapeutic agent; wherein the first therapeutic agent is a compound of Formula I, a pharmaceutically acceptable salt thereof, or combinations thereof; and wherein, when present, the optional second therapeutic agent is tetrahydrouridine, a 2'-fluorinated tetrahydrouridine derivative, a pharmaceutically acceptable salt thereof, or combinations thereof; or (b) a disclosed pharmaceutical composition. In a still further aspect, the product comprises a disclosed pharmaceutical composition comprising a therapeutically effective amount of comprising a 2′-deoxycytidine analog and optionally a therapeutically effective amount of a CDA inhibitor. In a yet further aspect, the product comprises a therapeutically effective amount of at least one disclosed 2′-deoxycytidine analog. In an even further aspect, the use comprises administering a therapeutically effective amount of at least one 2′-deoxycytidine analog, and optionally a therapeutically effective amount of at least one CDA inhibitor. In various aspects, the hematological disorder is sickle cell anemia or a thalassemia.

In various aspects, the disclosed products for treatment of a disease or disorder comprise a therapeutically effective amount of a compound of a first therapeutic agent, an optional second therapeutic agent, and at least one pharmaceutically acceptable excipient; wherein the first therapeutic agent is 5-aza-4′-thio-2′-deoxycytidine, 5-fluoro-2′-deoxycytidine, a pharmaceutically acceptable salt thereof, or combinations thereof; and wherein the second therapeutic agent is a therapeutic agent disclosed herein, a pharmaceutically acceptable salt thereof, or combinations thereof.

In a further aspect, the disclosed products for treatment of a disease or disorder comprise a therapeutically effective amount of a 2′-deoxycytidine analog from about 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values.

In a further aspect, the disclosed products for treatment of a disease or disorder comprise a therapeutically effective amount of a 2′-deoxycytidine analog of from about 5 mg/m$^2$ to about 135 mg/m$^2$, or can be about 5, 10, 15, 20, 25, 30, 35, 40, 45, 50, 55, 60, 65, 70, 75, 80, 85, 90, 95, 100, 105, 110, 115, 120, 125, 130, or about 135 mg/m$^2$, or a combination of any of the foregoing values, or a range encompassing any of the foregoing values. In a yet further aspect, the dose of the cytidine analog is 134 mg/m$^2$.

In a further aspect, the disclosed products for treatment of a disease or disorder comprise a therapeutically effective amount of a CDA inhibitor, e.g., a tetrahydrouridine analog, to the subject. In a still further aspect, the therapeutically effective amount of the tetrahydrouridine analog, when optionally included with the disclosed product for treatment of a disease or disorder, can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In a yet further aspect, the therapeutically effective amount of the optionally included tetrahydrouridine analog can be from about 50 to about 350 mg/m$^2$, or can be about 50, 100, 150, 200, 250, 300, or about 350 mg/m$^2$, or a combination of any of the foregoing values, or a range encompassing any of the foregoing values. In one aspect, the products disclosed herein can include 145 mg/m$^2$ cytidine analog and optionally 350 mg/m$^2$ tetrahydrouridine.

In a further aspect, the disclosed products for treatment of a disease or disorder comprise a product such that tetrahydrouridine is optionally administered before administering the 2′-deoxycytidine analog, concurrently with the 2′-deoxycytidine analog, or after the 2′-deoxycytidine analog. In any of these aspects, the tetrahydrouridine is bioavailable from about 1 to about 180 minutes, or from about 15 to about 60 minutes, before the 2′-deoxycytidine analog, or about 15, 30, 45, 60, 75, 90, 105, 120, 135, 150, 165, or about 180 minutes before the 2′-deoxycytidine analog, or a combination of any of the foregoing values, or a range encompassing any of the foregoing values. In a further aspect, tetrahydrouridine is not administered to the subject. In a further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In one aspect, the disclosed products for treatment of a disease or disorder comprise an additional therapeutic agent such as a AN-233 a prodrug conjugate of butyric acid (BA) and δ-aminolevulinate (ALA), Janus kinase (JAK) inhibitor, hydroxyurea, a hemoglobin oxygen-affinity modulator such as, for example, voxelotor sold under the trade name OXBRYTA®, luspatercept sold under the trade name REBLOZYL®, a P-selectin binder such as, for example, crizanlizumab or inclacumab, a pyruvate kinase M2 activator such as, for example, AG348 or FT-4202, a PDE9 inhibitor such as, for example, IMR-687, an HDAC inhibitor, a stimulator of soluble guanylate cyclase such as, for example, olinciguat, an anti-hepcidin therapy such as for example, PGT-300 or siRNA-GalNAc, or the like. In another aspect, the additional therapy can be an iron chelator such as, for example, desferasirox (sold under the trade name EXIADE®) or deferiprone (sold under the trade name FERRIPROX®. In still another aspect, the additional therapy can be a gene therapy product including, but not limited to, ZYNTEGLO®, ARU-1801, EDIT-301, ST-400, CTX001, ET-01, or a combination thereof.

In another aspect, the disclosed products for treatment of a disease or disorder comprise an activator of erythrocyte pyruvate kinase-R (PKR), i.e., a PKR activator compound. Pyruvate kinase R (PKR) is the isoform of pyruvate kinase expressed in RBCs and is a key enzyme in glycolysis. The PKR activator can be a compound having an AC$_{50}$ value of less than 1 μM using a suitable assay as known to the skilled artisan (e.g., see the Luminescence Assay in Example 2 in U.S. Pat. Publ. 2022/0031671), In a further aspect, a suitable PKR activator is Etavopivat (also known as FT-4202), i.e., the compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a stereoisomer thereof, or a pharmaceutically acceptable salt and/or other solid form thereof, as shown below:

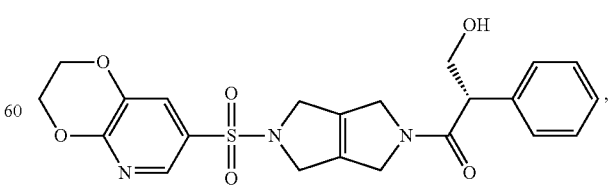

In a further aspect, a suitable PKR activator can be selected from one or more of the compounds disclosed in FIG. 1 of U.S. Pat. Publ. 2022/0031671.

In a further aspect, a suitable PKR activator is mitapivat, i.e., the compound N-[4-[4-(cyclopropylmethyl)piperazine-1-carbonyl]phenyl]quinoline-8-sulfonamide, or a pharmaceutically acceptable salt and/or other solid form thereof, as shown below:

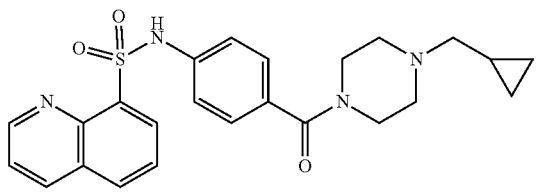 [SMILES: O=C(c1ccc(NS(=O)(=O)c2cccc3cccnc23)cc1)N1CCN(CC2CC2)CC1]

In a further aspect, a suitable PKR activator is rucaparib (AG-014699, PF-01367338), or a pharmaceutically acceptable salt and/or other solid form thereof, as shown below:

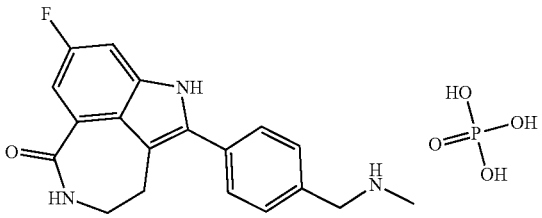 [SMILES: CNCc1ccc(-c2[nH]c3cc(F)cc4c3c2CCNC4=O)cc1 ; O=P(O)(O)O]

In a further aspect, the disclosed products for treatment of a disease or disorder comprise a proton pump inhibitor, e.g., famotidine or omeprazole. In a still further aspect, the proton pump inhibitor is selected from the group consisting essentially of omeprazole, lansoprazole, esomeprazole, rabeprazole, pantoprazole, pariprazole, tenatoprazole, leminoprazole, hydroxyomeprazole, dontoprazole, habeprazole, periprazole, or a free base, free acid, salt, hydrate, ester, amide, enantiomer, isomer, tautomer, polymorph, prodrug thereof, and combinations thereof.

In one aspect, the disclosed products for treatment of a disease or disorder comprise a Gardos channel blocker selected from the group consisting of imidazole antimycotics, clotrimazole, metronidazole, econazole, arginine, Tram-34, harybdotoxin, nifedipine, 2,2-Bis(4-fluorophenyl)-N-methoxy-2-phenylacetamidine, 2-(2-Chlorophenyl)-2,2-diphenylacetaldehyde oxime, 2-(2-Chlorophenyl)-2,2-bis(4-fluorophenyl)-N-hydroxyacetamidine, 2,2,2-Tris(4-fluorophenyl)-N-hydroxyacetamidine, 2-(2-Fluorophenyl)-2-(4-fluorophenyl)-N-hydroxy-2-phenylacetamidine, phosphoric acid 3-(2-oxazolyl)-4-[3-(trifluoromethyl)phenylsulfonamido]phenyl monoester, N-[2-(4,5-Dihydrooxazol-2-yl)phenyl]-3-(trifluoromethyl)benzenesulf onamide, N-[4-Methoxy-2-(2-oxazolyl)phenyl]benzene sulfonamide, N-[4,5-Dimethoxy-2-(3-methyl-1,2,4-oxadiazol-5-yl)phenyl]-3-(trifluoromethyl)benzenesulfon-amide, N-[2-(2-Furyl)phenyl]-3-(trifluoromethyl)benzenesulfonamide, N-[4-Methyl-2-(2-oxazolyl)phenyl]-3-(trifluoromethyl) benzenesulfonamide and senicapoc, preferably senicapoc or Tram-34.

Product for Use in the Treatment of a Disorder Associated with a Clinical Need to Increase Fetal Hemoglobin Expression.

In one aspect, disclosed herein are uses of products for treatment of a disease or disorder associated with a clinical need to increase fetal hemoglobin expression in a subject, the product comprising administering a therapeutically effective amount of a disclosed pharmaceutical composition or a disclosed therapeutic agent to a subject. In a further aspect, the product comprises a therapeutically effective amount of a disclosed pharmaceutical composition comprising at least one DNMT1 inhibitor, e.g., at least one, 2'-deoxycytidine analog and at least one HbF inducer. In a still further aspect, the product comprises a pharmaceutical composition comprising a therapeutically effective amount of a disclosed pharmaceutical composition comprising at least one DNMT1 inhibitor, e.g., at least one 2'-deoxycytidine analog, at least on HbF inducer, and optionally at least one CDA inhibitor. In a yet further aspect, the product comprises a therapeutically effective amount of at least one DNMT1 inhibitor, e.g., at least one 2'-deoxycytidine analog and at least one HbF inducer. In an even further aspect, the product comprises a therapeutically effective amount of at least one DNMT1 inhibitor, e.g., at least one 2'-deoxycytidine analog, a therapeutically effective amount of at least one HbF inducer, and optionally a therapeutically effective amount of at least one CDA inhibitor.

In various aspects, the disclosed products for use for in the treatment of a disease or disorder associated with a clinical need to increase fetal hemoglobin expression in a subject comprise a therapeutically effective amount of a compound of a first therapeutic agent, an optional second therapeutic agent, and at least one pharmaceutically acceptable excipient; wherein the first therapeutic agent is 5-aza-4'-thio-2'-deoxycytidine, 5-fluoro-2'-deoxycytidine, a pharmaceutically acceptable salt thereof, or combinations thereof; and wherein the second therapeutic agent is a therapeutic agent disclosed herein, a pharmaceutically acceptable salt thereof, or combinations thereof.

In a further aspect, the disclosed products for use for in the treatment of a disease or disorder associated with a clinical need to increase fetal hemoglobin expression in a subject, e.g., a subject having sickle cell anemia, thalassemia, or other blood disorder associated with a decreased amount of normal hemoglobin. In a further aspect, the need for increasing fetal hemoglobin expression is associated with a hemoglobinopathy. In a yet further aspect, the subject has already been identified as having a hemoglobinopathy. In an even further aspect, the hemoglobinopathy is associated with sickle cell disease or thalassemia.

In a further aspect, the disclosed products for use for in the treatment of a disease or disorder associated with a clinical need to increase fetal hemoglobin expression in a subject comprises a therapeutically effective amount of at least one DNMT1 inhibitor, e.g., at least one 2'-deoxycytidine analog, of from about 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values. In a still further aspect, In a further aspect, the disclosed products for use for in the treatment of a disease or disorder associated with a clinical need to increase fetal hemoglobin expression in a subject comprises a therapeutically effective amount of at least one DNMT1 inhibitor, e.g., at least one 2'-deoxycytidine analog, of from about 5 mg/m$^2$ to about 135 mg/m$^2$, or can be about 5, 10, 15, 20, 25, 30, 35, 40, 45, 50, 55, 60, 65, 70, 75, 80, 85, 90, 95, 100, 105, 110, 115, 120, 125, 130, or about 135 mg/m$^2$, or a combination of any of the foregoing values, or a range encompassing any of the foregoing values. In a yet further aspect, the dose of the cytidine analog is 134 mg/m$^2$. In a further aspect, the use for increasing fetal hemoglobin expression comprises administering a therapeutically effective amount of at least one DNMT1 inhibitor, e.g., at least one 2'-deoxycytidine analog, of from 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values.

In a further aspect, the HbF inducer comprises one or more epigenetic modifiers as described herein can be administered in a therapeutically effective or therapeutically synergistic amount. As used herein, a "therapeutically-effective amount" is an amount such that coadministration of the one or more DNMT1 inhibitors and the one or more HbF inducers (which can include epigenetic modifiers), or administration of a single therapeutic composition or formulation including both classes of drug, as described herein, results in an increase or upregulation of HbF, or results in inhibition of a blood disorder as disclosed herein, or both. Meanwhile, as used herein, a "therapeutically synergistic amount" is the amount of one or more DNMT1 inhibitors and the one or more HbF chemical inducers necessary to significantly reduce or eliminate conditions or symptoms associated with a blood disorder as disclosed herein, and/or to increase or upregulate HbF levels.

In a further aspect, the at least one HbF chemical inducer can be an epigenetic modifier such as, for example, at least one DNA methylation inhibitor, at least one histone deacetylase (HDAC) inhibitor, at least one DNA methylation inhibitor, at least one PK2 inhibitor, or a combination thereof, that can increase HbF levels in hematopoietic progenitor cells. In a further aspect, the DNA methylation inhibitor can be 5-aza-2'-deoxycytidine. In another aspect, the HDAC inhibitor can be selected from suberoylanilide hydroxamic acid (SAHA, also marketed as Vorinostat), amide analogues of trichostatin A, hydroxamic acid analogs of trapoxin, and scriptaid (6-(1,3-Dioxo-1H, 3H-benzo[de]isoquinolin-2-yl)-hexanoic acid hydroxyamide) and analogs.

In a further aspect, a first product can comprise a DNMT1 inhibitor and a second product can comprise a HbF chemical inducer, and the first and second pharmaceutical compositions can be co-administered. Coadministration can be sequentially or simultaneously.

In a further aspect, the disclosed products for use for in the treatment of a disease or disorder associated with a clinical need to increase fetal hemoglobin expression in a subject optionally comprises a product comprising a therapeutically effective amount of a CDA inhibitor, e.g., a tetrahydrouridine analog. In a still further aspect, the therapeutically effective amount of the optional tetrahydrouridine analog can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In a yet further aspect, the therapeutically effective amount of the optional tetrahydrouridine analog can be from about 50 to about 350 mg/m$^2$, or can be about 50, 100, 150, 200, 250, 300, or about 350 mg/m$^2$, or a combination of any of the foregoing values, or a range encompassing any of the foregoing values. In one aspect, the combinatorial compositions disclosed herein can include 145 mg/m$^2$ cytidine analog and optionally 350 mg/m$^2$ tetrahydrouridine.

In a further aspect, the disclosed products for use for in the treatment of a disease or disorder associated with a clinical need to increase fetal hemoglobin expression in a subject optionally comprises a therapeutically effective amount of tetrahydrouridine analog. In one aspect, the therapeutically effective amount of optionally administered tetrahydrouridine can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In any of these aspects, the tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a further aspect, tetrahydrouridine is not administered to the subject. In a further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In a further aspect, the product is formulated such that tetrahydrouridine is optionally administered before administering the 2'-deoxycytidine analog, concurrently with the 2'-deoxycytidine analog, or after the 2'-deoxycytidine analog. In any of these aspects, the tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a still further aspect, tetrahydrouridine is not administered to the subject. In a yet further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In one aspect, the disclosed products for use for in the treatment of a disease or disorder associated with a clinical need to increase fetal hemoglobin expression in a subject can comprise a product comprising an additional therapeutic agent such as a AN-233 a prodrug conjugate of butyric acid (BA) and δ-aminolevulinate (ALA), Janus kinase (JAK) inhibitor, hydroxyurea, a hemoglobin oxygen-affinity modulator such as, for example, voxelotor sold under the trade name OXBRYTA®, luspatercept sold under the trade name REBLOZYL®, a P-selectin binder such as, for example, crizanlizumab or inclacumab, a pyruvate kinase M2 activator such as, for example, AG348 or FT-4202, a PDE9 inhibitor such as, for example, IMR-687, an HDAC inhibitor, a stimulator of soluble guanylate cyclase such as, for example, olinciguat, an anti-hepcidin therapy such as for example, PGT-300 or siRNA-GalNAc, or the like. In another aspect, the additional therapy can be an iron chelator such as, for example, desferasirox (sold under the trade name EXIADE®) or deferiprone (sold under the trade name FERRIPROX®. In still another aspect, the additional therapy can be a gene therapy product including, but not limited to, ZYNTEGLO®, ARU-1801, EDIT-301, ST-400, CTX001, ET-01, or a combination thereof.

In another aspect, the disclosed products for use for in the treatment of a disease or disorder associated with a clinical need to increase fetal hemoglobin expression in a subject includes a product formulated for administration of an activator of erythrocyte pyruvate kinase-R (PKR), i.e., a PKR activator compound. Pyruvate kinase R (PKR) is the isoform of pyruvate kinase expressed in RBCs and is a key enzyme in glycolysis. The PKR activator can be a compound having an $AC_{50}$ value of less than 1 μM using a suitable assay as known to the skilled artisan (e.g., see the Luminescence Assay in Example 2 in U.S. Pat. Publ. 2022/0031671), In a further aspect, a suitable PKR activator is Etavopivat (also known as FT-4202), i.e., the compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a stereoisomer thereof, or a pharmaceutically acceptable salt and/or other solid form thereof, as shown below:

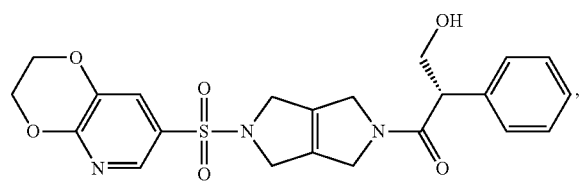 [SMILES: O=C([C@H](CO)c1ccccc1)N1CC2=C(C1)CN(S(=O)(=O)c1cnc3c(c1)OCCO3)C2]

In a further aspect, a suitable PKR activator can be selected from one or more of the compounds disclosed in FIG. 1 of U.S. Pat. Publ. 2022/0031671.

In a further aspect, a suitable PKR activator is mitapivat, i.e., the compound N-[4-[4-(cyclopropylmethyl)piperazine-1-carbonyl]phenyl]quinoline-8-sulfonamide, or a pharmaceutically acceptable salt and/or other solid form thereof, as shown below:

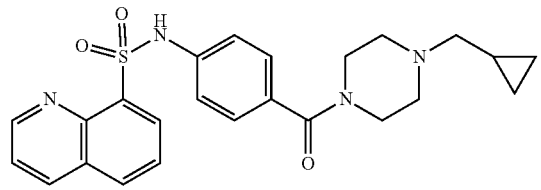 [SMILES: O=C(c1ccc(NS(=O)(=O)c2cccc3cccnc23)cc1)N1CCN(CC2CC2)CC1]

In a further aspect, a suitable PKR activator is rucaparib (AG-014699, PF-01367338), or a pharmaceutically acceptable salt and/or other solid form thereof, as shown below:

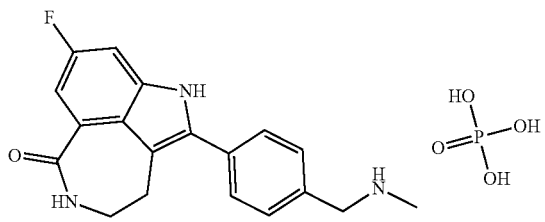 [SMILES: CNCc1ccc(-c2[nH]c3cc(F)cc4c3c2CCNC4=O)cc1 ; O=P(O)(O)O]

In a further aspect, the disclosed products for use for in the treatment of a disease or disorder associated with a clinical need to increase fetal hemoglobin expression in a subject includes a product formulated for administration of a proton pump inhibitor, e.g., famotidine or omeprazole. In a still further aspect, the proton pump inhibitor is selected from the group consisting essentially of omeprazole, lansoprazole, esomeprazole, rabeprazole, pantoprazole, pariprazole, tenatoprazole, leminoprazole, hydroxyomeprazole, dontoprazole, habeprazole, periprazole, or a free base, free acid, salt, hydrate, ester, amide, enantiomer, isomer, tautomer, polymorph, prodrug thereof, and combinations thereof.

In one aspect, the disclosed products for use for in the treatment of a disease or disorder associated with a clinical need to increase fetal hemoglobin expression in a subject can comprise a product formulate for administration of an Gardos channel blocker selected from the group consisting of imidazole antimycotics, clotrimazole, metronidazole, econazole, arginine, Tram-34, harybdotoxin, nifedipine, 2,2-Bis(4-fluorophenyl)-N-methoxy-2-phenylacetamidine, 2-(2-Chlorophenyl)-2,2-diphenylacetaldehyde oxime, 2-(2-Chlorophenyl)-2,2-bis(4-fluorophenyl)-N-hydroxyacetamidine, 2,2,2-Tris(4-fluorophenyl)-N-hydroxyacetamidine, 2-(2-Fluorophenyl)-2-(4-fluorophenyl)-N-hydroxy-2-phenylacetamidine, phosphoric acid 3-(2-oxazolyl)-4-[3-(trifluoromethyl)phenylsulfonamido]phenyl monoester, N-[2-(4,5-Dihydrooxazol-2-yl)phenyl]-3-(trifluoromethyl)benzenesulfonamide, N-[4-Methoxy-2-(2-oxazolyl)phenyl]benzene sulfonamide, N-[4,5-Dimethoxy-2-(3-methyl-1,2,4-oxadiazol-5-yl)phenyl]-3-(trifluoromethyl)benzenesulfon-amide, N-[2-(2-Furyl)phenyl]-3-(trifluoromethyl)benzenesulfonamide, N-[4-Methyl-2-(2-oxazolyl)phenyl]-3-(trifluoromethyl)benzenesulfonamide and senicapoc, preferably senicapoc or Tram-34.

In various aspects, also disclosed herein are products for use for in the treatment of a disease or disorder associated with a clinical need to increase fetal hemoglobin expression in a subject, the product formulated for administering to a subject (a) a therapeutically effective amount of a 2'-deoxycytidine analog as disclosed herein and optionally, (b) a therapeutically effective amount of tetrahydrouridine.

In a further aspect, the cytidine analog and the optional tetrahydrouridine can be packaged in two separate dosage forms and administered simultaneously. In another aspect, the optional tetrahydrouridine is administered before or after the cytidine analog. In yet another aspect, the cytidine analog and the optional tetrahydrouridine are packaged in the same dosage form. Further in this aspect, the dosage form can be an oral dosage form such as, for example, a layered tablet, a tablet-in-tablet, a tablet-in-capsule, or a capsule-in-capsule. In any of these aspects, the dosage form enables fast release of the tetrahydrouridine and delayed release of the cytidine analog.

In a further aspect, the disclosed products for use for in the treatment of a disease or disorder associated with a clinical need to increase fetal hemoglobin expression in a subject can be formulated to further includes step (c) or administering an additional chemotherapeutic agent to the subject. In one aspect, the additional chemotherapeutic agent can be an anti-metabolite, hydroxyurea, decitabine, a prokineticin 2 activator, irinotecan, doxorubicin, a histone deacetylase inhibitor, an anti-viral agent, an anti-retroviral agent, or a combination thereof.

In a further aspect, the cytidine analog and optional tetrahydrouridine are packaged in a first dosage form and the additional chemotherapeutic agent is packaged in a second dosage form. In one aspect, the first dosage form can be administered before, after, or simultaneously with the second dosage form. In other aspects, the cytidine analog, optimal tetrahydrouridine, and additional chemotherapeutic agent are packaged in the same dosage form, which can be, In a further aspect, a layered tablet, a tablet-in-tablet, a tablet-in-capsule, a capsule-in-capsule, or another dosage form. In any of these aspects, a single dosage form can be prepared in order to enable fast release of optional tetrahydrouridine and delayed release of the cytidine analog and additional chemotherapeutic agent. In one aspect, the additional chemotherapeutic agent can be 5-aza-4'-thio-2'-deoxycytidine or a combination of 5-aza-4'-thio-2'-deoxycytidine and tetrahydrouridine.

In any of these aspects, after administration of the formulations disclosed herein to a subject in need thereof, fetal hemoglobin level in the blood of the subject increases to at least 5, 7.5, 10, 12.5, 15, 17.5, or 20%, or a combination of any of the foregoing values, or a range encompassing any of the foregoing values, compared to fetal hemoglobin levels in the subject prior to treatment. In another aspect, prior to performance of the use, the subject can have a fetal hemoglobin level of less than 1 g/dL, whereas after the performance of the use, the subject can have a fetal plus total hemoglobin level of greater than 1 g/dL. In a further aspect, the fetal plus total hemoglobin level remains greater than 1 g/dL for at least 6 months.

Product for Use in the Treatment of a Disease Associated with Abnormal Cell Proliferation.

In one aspect, disclosed herein are products for use in the treatment of a disease associated with abnormal cell proliferation in a subject, the use comprising administering a therapeutically effective amount of a disclosed pharmaceutical composition to a subject, e.g., a disclosed pharmaceutical composition comprising a 2'-deoxycytidine analog. In a further aspect, the disease associated with abnormal cell proliferation can be bladder cancer, breast cancer, brain cancer, an endocrine cancer, retinoblastoma, cervical cancer, colon cancer, rectal cancer, endometrial cancer, renal cell carcinoma, renal pelvis carcinoma, Wilms tumor, a cancer of the oral cavity, liver cancer, gall bladder cancer, cholangiocarcinoma, melanoma, mesothelioma, myelodysplastic syndrome, acute myelogenous leukemia, non-small cell lung cancer, basal cell skin cancer, squamous cell skin cancer, ovarian cancer, pancreatic cancer, prostate cancer, soft tissue sarcoma, osteosarcoma, small cell lung cancer, thyroid cancer, or a combination thereof. In a still further aspect, the use further comprises the step of identifying a subject having an abnormal cell proliferation. In a yet further aspect, the subject has already been identified as having an abnormal cell proliferation.

In a further aspect, the products for use in the treatment of a disease associated with abnormal cell proliferation in a subject comprises a therapeutically effective amount of a 2'-deoxycytidine analog can be from about 0.1 to about 150 mg/m$^2$, or can be from about 10 to about 150 mg/m$^2$, or can be about 0.1, 0.5, 1, 5, 10, 15, 20, 25, 30, 35, 40, 45, 50, 55, 60, 65, 70, 76, 80, 85, 90, 95, 100, 105, 110, 115, 120, 125, 130, 135, 140, 145, or about 150 mg/m$^2$, or a combination of any of the foregoing values, or a range encompassing any of the foregoing values.

In a further aspect, the products for use in the treatment of a disease associated with abnormal cell proliferation in a subject optionally comprises a product formulating for administering a therapeutically effective amount of tetrahydrouridine analog to the subject. In one aspect, the therapeutically effective amount of optionally administered tetrahydrouridine can be from about 100 to about 600 mg/m$^2$ or can be about 100, 150, 200, 250, 300, 350, 400, 450, 500, 550, or about 600 mg/m$^2$, or a combination of any of the foregoing values, or a range encompassing any of the foregoing values. In one aspect, tetrahydrouridine is optionally administered before administering the 2'-deoxycytidine analog, concurrently with the 2'-deoxycytidine analog, or after the 2'-deoxycytidine analog. In any of these aspects, the optionally administered tetrahydrouridine is bioavailable from about 1 to about 180 minutes, or from about 15 to about 60 minutes, before the 2'-deoxycytidine analog, or about 15, 30, 45, 60, 75, 90, 105, 120, 135, 150, 165, or about 180 minutes before the 2'-deoxycytidine analog, or a combination of any of the foregoing values, or a range encompassing any of the foregoing values. In a further aspect, tetrahydrouridine is not administered to the subject. In a further aspect, the tetrahydrouridine is not acid stable and is encapsulated in an enteric coating in the formulations disclosed herein in order to preserve its activity when administered to the subject. In a further aspect, the enteric coating can be formulated such that extended release of tetrahydrouridine is possible by means such as, for example, microencapsulation, embedding in a matrix of a single layer or of different layers, or the like.

In a further aspect, the products for use in the treatment of a disease associated with abnormal cell proliferation in a subject can comprise a product formulated for administration of an additional therapy including, but not limited to, surgery, radiation, chemotherapy, or a combination thereof. In a further aspect, chemotherapy can include administering a cytotoxic compound to the subject. In a further aspect, the cytotoxic compound can be an anti-metabolite, hydroxyurea, decitabine, a prokineticin 2 activator, irinotecan, doxorubicin, a histone deacetylase inhibitor, an antiviral agent, an anti-retroviral agent, or a combination thereof. In any of these aspects, the additional therapy can be administered before, during, or after the use disclosed herein.

In one aspect, the additional therapy can be a PD1 inhibitor, a Janus kinase (JAK) inhibitor, hydroxyurea, a DNMT1 inhibitor, a hemoglobin oxygen-affinity modulator such as, for example, voxelotor sold under the trade name OXBRYTA®, luspatercept sold under the trade name REBLOZYL®, a P-selectin binder such as, for example, crizanlizumab or inclacumab, a pyruvate kinase M2 activator such as, for example, AG348 or FT-4202, a PDE9 inhibitor such as, for example, IMR-687, an HDAC inhibitor, a stimulator of soluble guanylate cyclase such as, for example, olinciguat, an anti-hepcidin therapy such as for example, PGT-300 or siRNA-GalNAc, or the like. In another aspect, the additional therapy can be an iron chelator such as, for example, desferasirox (sold under the trade name EXIADE®) or deferiprone (sold under the trade name FERRIPROX®. In still another aspect, the additional therapy can be a gene therapy product including, but not limited to, ZYNTEGLO®, ARU-1801, EDIT-301, ST-400, CTX001, ET-01, or a combination thereof.

Kits.

In a further aspect, the present disclosure relates to kits comprising at least one disclosed compound, or a pharmaceutically acceptable salt, hydrate, solvate, or polymorph thereof, and one or more of: (a) at least one agent known to decrease DNMT1 activity; (b) at least one agent known to treat a disorder associated with DNMT1 activity; (c) instructions for treating a disorder associated with DNMT1 activity; or (d) instructions for administering the compound in connection with another sickle cell disease, thalassemia, or anti-cancer therapy.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

In one aspect, disclosed herein is a kit for treating a hematological disorder or a disease associated with abnormal cell proliferation in a subject, the kit comprising a therapeutically effective amount of a 2'-deoxycytidine analog and a therapeutically effective amount of tetrahydrouridine. In a further aspect, the therapeutically effective amount of the 2'-deoxycytidine analog is from about 0.1 to about 150 mg\m$^2$ or is about 10 to 150 mg/m$^2$, or about 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, or about 150 mg/m$^2$, or a combination of any of the foregoing values, or a range encompassing any of the foregoing values. In another aspect, the therapeutically effective amount of the tetrahydrouridine is from about 100 to about 600 mg/m$^2$, or is about 100, 150, 200, 250, 300, 350, 400, 450, 500, 550, or about 600 mg/m$^2$, or a combination of any of the foregoing values, or a range encompassing any of the foregoing values.

In one aspect, the 2'-deoxycytidine analog and the optional tetrahydrouridine are packaged in two separate dosage forms (e.g., pills, tablets, lyophilized powders for resuspension and injection, etc.). In a further aspect, the two separate dosage forms can be the same or different (e.g., one tablet and one lyophilized powder for resuspension and injection). Further in this aspect, the 2'-deoxycytidine analog can be administered before, concurrently with, or after the tetrahydrouridine. In another aspect, the 2'-deoxycytidine analog and the tetrahydrouridine are packaged in the same dosage form. In a further aspect, when both ingredients are packaged in the same dosage form, that dosage form is selected from a layered tablet, a tablet-in-tablet form, a tablet-in-capsule form, a capsule-in-capsule form, or some combination thereof. In a further aspect, the single dosage form enables fast release of tetrahydrouridine and delayed release of the cytidine analog.

In a further aspect, the kits disclosed herein further include an additional chemotherapeutic agent such as, for example, an anti-metabolite, hydroxyurea, decitabine, a prokineticin 2 activator, irinotecan, doxorubicin, a histone deacetylase inhibitor, an anti-viral agent, an anti-retroviral agent, or a combination thereof.

In one aspect, disclosed herein is a kit for treating a tumor, refractory tumor, hematological malignancy, blood disorder, or combination thereof. In a further aspect, the kit can include a first dosage form such as, for example, a pill, tablet, capsule, or other oral dosage form including a cytidine analog such as, for example, 5-fluoro-2'-deoxycytidine, and optionally tetrahydrouridine or a tetrahydrouridine analog, and a carrier. In another aspect, the kit further includes a second dosage form such as, for example, a pill, tablet, capsule, or other oral dosage form including 5-azacytidine; optionally tetrahydrouridine or a tetrahydrouridine analog; and a carrier. In still another aspect, the kit can also include instructions. In any of these aspects, the kit can include oral dosage forms that contain microspheres or microparticles as disclosed herein. In one aspect, the second dosage form is administered simultaneously with the first dosage form, or before or after administration of the first dosage form. In a further aspect, the cytidine analog, optional tetrahydrouridine, and additional chemotherapeutic agent are all packaged in the same dosage form, which can be selected from a layered tablet, a tablet-in-tablet form, a tablet-in-capsule form, or a capsule-in-capsule form. Further in this aspect, the dosage form may enable fast release of tetrahydrouridine and delayed release of other compounds. In a further aspect, the additional chemotherapeutic agent can be 5-aza-4'-thio-2'-deoxycytidine or a combination of 5-aza-4'-thio-2'-deoxycytidine and optionally tetrahydrouridine.

In any of the above aspects, the kit further comprises instructions on using the kit.

Research Tools.

The disclosed compounds and pharmaceutical compositions have activity as inhibitors of DNMT1 As such, the disclosed compounds are also useful as research tools. Accordingly, one aspect of the present disclosure relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Still another aspect of the invention relates to a method of studying a biological system, e.g., a model animal for a clinical condition, or biological sample comprising a DNMT1 protein, the method comprising: (a) contacting the biological system or sample with a compound of the invention; and (b) determining the effects caused by the compound on the biological system or sample.

Aspects

The following listing of exemplary aspects supports and is supported by the disclosure provided herein.

Aspect 1. A pharmaceutical composition comprising a therapeutically effective amount of a compound of a first therapeutic agent, an optional second therapeutic agent, and at least one pharmaceutically acceptable excipient; wherein the first therapeutic agent is a compound of Formula I; and wherein, when present, the optional second therapeutic agent, a pharmaceutically acceptable salt thereof, or combinations thereof.

Aspect 2. The pharmaceutical composition of Aspect 1, wherein the first therapeutic agent is selected from 5-aza-4'-thio-2'-deoxycytidine, 5-fluoro-2'-deoxycytidine, a pharmaceutically acceptable salt thereof, and combinations thereof.

Aspect 3. The pharmaceutical composition of Aspect 1 or Aspect 2, wherein the first therapeutic agent has the following structure:

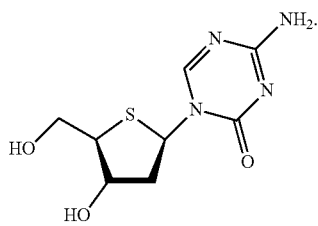 [SMILES: Nc1ncn([C@H]2C[C@@H](O)[C@@H](CO)S2)c(=O)n1]

Aspect 4. The pharmaceutical composition of Aspect 1 or Aspect 2, wherein the first therapeutic agent has the following structure:

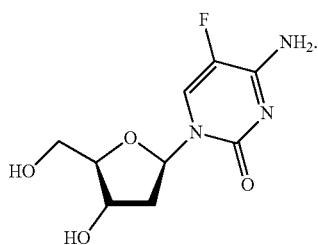

Aspect 5. The pharmaceutical composition of any of Aspect 1-Aspect 4, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity a P-selectin binder; a pyruvate kinase M2 activator; a PDE9 inhibitor; a stimulator of soluble guanylate cyclase; an anti-hepcidin therapy; an iron chelator; a tetrahydrouridine derivative; a 2'-fluorinated tetrahydrouridine derivative; pharmaceutically acceptable salts thereof and combinations thereof.

Aspect 6. The pharmaceutical composition of Aspect 5, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity such as Voxelotor (GBT440); AN-233; a P-selectin binder such as, for example, crizanlizumab or inclacumab, a pyruvate kinase M2 activator such as, for example, AG348 or FT-4202; a PDE9 inhibitor such as, for example, IMR-687; a stimulator of soluble guanylate cyclase such as, for example, olinciguat; an anti-hepcidin therapy such as, for example, PGT-300 or siRNA-GalNAc, or the like; an iron chelator such as, for example, desferasirox or deferiprone; a tetrahydrouridine derivative, a 2'-fluorinated tetrahydrouridine derivative, and combinations thereof.

Aspect 7. The pharmaceutical composition of Aspect 5, wherein the second therapeutic agent is selected from a tetrahydrouridine derivative, a 2'-fluorinated tetrahydrouridine derivative, and combinations thereof.

Aspect 8. The pharmaceutical composition of Aspect 7, wherein the second therapeutic agent is selected from tetrahydrouridine; 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl)tetra-hydro-2 (1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone, a pharmaceutically acceptable salt thereof, or combinations thereof.

Aspect 9. The pharmaceutical composition of Aspect 7, wherein the second therapeutic agent is a tetrahydrouridine derivative.

Aspect 10. The pharmaceutical composition of Aspect 7, wherein the second therapeutic agent is a 2'-fluorinated tetrahydrouridine derivative.

Aspect 11. The pharmaceutical composition of Aspect 7, wherein the second therapeutic agent is a 2'-fluorinated tetrahydrouridine derivative; and wherein the 2'-fluorinated tetrahydrouridine derivative is selected from 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl) tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone.

Aspect 12. The pharmaceutical composition of any one of Aspect 1-Aspect 11, wherein the therapeutically effective amount of the second therapeutic agent comprises from about 100 to about 600 mg/m$^2$.

Aspect 13. The pharmaceutical composition of any one of Aspect 1-Aspect 12, wherein the second therapeutic agent is bioavailable from about 1 to about 60 minutes before the first therapeutic agent.

Aspect 14. The pharmaceutical composition of any of Aspect 1-Aspect 13, wherein the first therapeutic agent is present in an amount of from about 1 mg to about 50 mg in a single dosage form.

Aspect 15. The pharmaceutical composition of any of Aspect 1-Aspect 14, wherein the pharmaceutical composition is administered orally.

Aspect 16. The pharmaceutical composition of Aspect 15, wherein the pharmaceutical composition for oral administration has a dosage form comprising a layered tablet, a tablet-in-tablet form, a tablet-in-capsule form, or a capsule-in-capsule form, granule, powder in sachet or bag, capsule, tablet, pill, or other oral solid dosage form.

Aspect 17. The pharmaceutical composition of any of Aspect 1-16, wherein the first therapeutic agent and the second therapeutic agent are formulated as a fixed dose combination.

Aspect 18. The pharmaceutical composition of any of Aspect 1-16, wherein the first therapeutic agent is formulated as a first pharmaceutical composition and the second therapeutic agent is formulated as a second pharmaceutical composition.

Aspect 19. A method for treating a hematological disorder in a subject, the method comprising either (A) administering a first therapeutic agent and optionally a second therapeutic agent; wherein the first pharmaceutical agent is a compound of Formula I, or a pharmaceutically acceptable salt thereof; and/or (B) administering the pharmaceutical composition of any one of Aspects 1-18.

Aspect 20. The method of Aspect 19, wherein the hematological disorder is selected from sickle cell disease, thalassemia, anemia, blood cancer, and combinations thereof.

Aspect 21. The method of Aspect 19 or Aspect 20, further comprising administrating a gene therapy product including, but not limited to, ZYNTEGLO®, ARU-1801, EDIT-301, ST-400, CTX001, ET-01, or a combination thereof.

Aspect 22. The method of any one of Aspect 19-21, wherein the first therapeutic agent is selected from 5-aza-4'-thio-2'-deoxycytidine, 5-fluoro-2'-deoxycytidine, a pharmaceutically acceptable salt thereof, and combinations thereof.

Aspect 23. The method of any one of Aspect 19-Aspect 22, wherein the first therapeutic agent has the following structure:

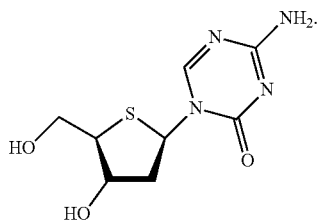 [SMILES: Nc1ncn([C@H]2C[C@@H](O)[C@@H](CO)S2)c(=O)n1]

Aspect 24. The method of any one of Aspect 19-Aspect 22, wherein the first therapeutic agent has the following structure:

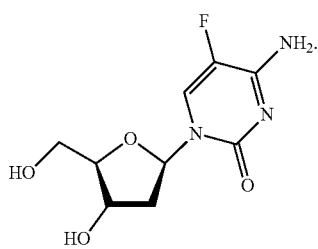 [SMILES: Nc1nc(=O)n([C@H]2C[C@@H](O)[C@@H](CO)O2)cc1F]

Aspect 25. The method of any one of Aspect 19-Aspect 24, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity a P-selectin binder; a pyruvate kinase M2 activator; a PDE9 inhibitor; a stimulator of soluble guanylate cyclase; an anti-hepcidin therapy; an iron chelator; a tetrahydrouridine derivative; a 2'-fluorinated tetrahydrouridine derivative; a pharmaceutically acceptable salt thereof, and combinations thereof.

Aspect 26. The method of Aspect 25, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity such as Voxelotor (GBT440); AN-233; a P-selectin binder such as, for example, crizanlizumab or inclacumab, a pyruvate kinase M2 activator such as, for example, AG348 or FT-4202; a PDE9 inhibitor such as, for example, IMR-687; a stimulator of soluble guanylate cyclase such as, for example, olinciguat; an anti-hepcidin therapy such as, for example, PGT-300 or siRNA-GalNAc, or the like; an iron chelator such as, for example, desferasirox or deferiprone; a tetrahydrouridine derivative, a 2'-fluorinated tetrahydrouridine derivative; a pharmaceutically acceptable salt thereof, and combinations thereof.

Aspect 27. The method of Aspect 25, wherein the second therapeutic agent is selected from a tetrahydrouridine derivative, a 2'-fluorinated tetrahydrouridine derivative; a pharmaceutically acceptable salt thereof, and combinations thereof.

Aspect 28. The method of Aspect 27, wherein the second therapeutic agent is selected from tetrahydrouridine; 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl)tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone; a pharmaceutically acceptable salt thereof, and combinations thereof.

Aspect 29. The method of Aspect 27, wherein the second therapeutic agent is a tetrahydrouridine derivative.

Aspect 30. The method of Aspect 27, wherein the second therapeutic agent is a 2'-fluorinated tetrahydrouridine derivative.

Aspect 31. The method of Aspect 27, wherein the second therapeutic agent is a 2'-fluorinated tetrahydrouridine derivative; and wherein the 2'-fluorinated tetrahydrouridine derivative is selected from 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-p-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl) tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone.

Aspect 32. The method of any one of Aspect 19-Aspect 31, wherein the first therapeutic agent and the second therapeutic agent are administered as the pharmaceutical composition of any one of Aspect 1-Aspect 18 to the subject.

Aspect 33. The method of any one of Aspect 19-Aspect 31, wherein the first therapeutic agent and the second therapeutic agent are administered sequentially or simultaneously.

Aspect 34. The method of any of Aspect 19-Aspect 33, wherein the subject is a human.

Aspect 35. The method of any of Aspect 19-Aspect 34, wherein the first therapeutic agent further comprises at least one at least one pharmaceutically acceptable excipient.

Aspect 36. The method of Aspect 35, wherein the at least one pharmaceutically acceptable excipient comprises mannitol, microcrystalline cellulose, crospovidone, or magnesium stearate.

Aspect 37. The method of any of Aspect 19-Aspect 36, wherein the second therapeutic agent further comprises at least one at least one pharmaceutically acceptable excipient.

Aspect 38. The method of Aspect 37, wherein the at least one pharmaceutically acceptable excipient comprises mannitol, microcrystalline cellulose, crospovidone, or magnesium stearate.

Aspect 39. The method of any of Aspect 19-Aspect 38, wherein the second pharmaceutical agent is administered as an enteric coated, stomach or gastric acid stable formulation.

Aspect 40. The method of any of Aspect 19-Aspect 39, wherein the first therapeutic agent is administered in an amount of from about 1 mg to about 50 mg in a single dosage form.

Aspect 41. The method of any of Aspect 19-Aspect 40, wherein the first therapeutic agent is administered orally.

Aspect 42. The method of Aspect 41, wherein the first therapeutic agent is administered orally as a dosage form comprising a layered tablet, a tablet-in-tablet form, a tablet-in-capsule form, or a capsule-in-capsule form, granule, powder in sachet or bag, capsule, tablet, pill, or other oral solid dosage form.

Aspect 43. The method of any of Aspect 19-Aspect 42, wherein the second therapeutic agent is administered in an amount of from about 100 to about 600 mg/m$^2$ in a single dosage form.

Aspect 44. The method of any of Aspect 19-Aspect 43, wherein the second therapeutic agent is bioavailable from about 1 to about 60 minutes before the first therapeutic agent.

Aspect 45. A kit for treating a hematological disorder, increasing fetal hemoglobin, or a disease associated with abnormal cell proliferation in a subject, the kit comprising: (a) a therapeutically effective amount of a first therapeutic agent, wherein the first therapeutic agent is a compound of formula I, a pharmaceutically acceptable salt thereof, or combinations thereof; (b) optionally a therapeutically effective amount of a second therapeutic agent, a pharmaceutically acceptable salt thereof, or combinations thereof; (c) a pharmaceutical composition of any one of Aspect 1-Aspect 18; and/or (d) instructions for treating a hematological disorder, a disorder to increase fetal hemoglobin in a subject, and/or a disease associated with abnormal cell proliferation, e.g., a cancer.

Aspect 46. The kit of Aspect 45, wherein the first therapeutic agent and the second therapeutic agent are packaged in two separate dosage or same dosage forms.

Aspect 47. The kit of Aspect 45 or Aspect 46, wherein the first therapeutic agent and the second therapeutic agent are packaged in the same dosage form.

Aspect 48. The kit of any one of Aspect 45-47, wherein dosage form enables fast release of the second therapeutic agent and delayed release of the first therapeutic agent.

Aspect 49. The kit of any one of Aspect 45-48, wherein the first therapeutic agent is selected from 5-aza-4'-thio-2'-deoxycytidine, 5-fluoro-2'-deoxycytidine, a pharmaceutically acceptable salt thereof, and combinations thereof.

Aspect 50. The kit of any one of Aspect 45-Aspect 49, wherein the first therapeutic agent has the following structure:

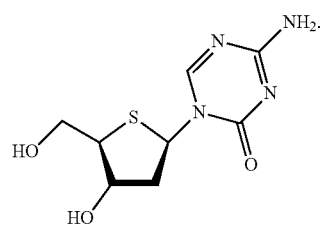 [SMILES: Nc1ncn([C@H]2C[C@@H](O)[C@@H](CO)S2)c(=O)n1]

Aspect 51. The kit of any one of Aspect 45-Aspect 50, wherein the first therapeutic agent has the following structure:

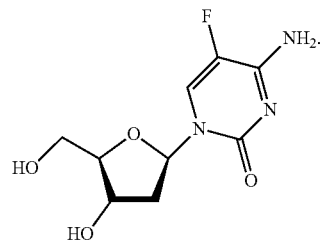 [SMILES: Nc1nc(=O)n([C@H]2C[C@@H](O)[C@@H](CO)O2)cc1F]

Aspect 52. The kit of any one of Aspect 45-Aspect 51, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity a P-selectin binder; a pyruvate kinase M2 activator; a PDE9 inhibitor; a stimulator of soluble guanylate cyclase; an anti-hepcidin therapy; an iron chelator; a tetrahydrouridine derivative; a 2'-fluorinated tetrahydrouridine derivative; pharmaceutically acceptable salts thereof and combinations thereof.

Aspect 53. The kit of Aspect 52, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity such as Voxelotor (GBT440); AN-233; a P-selectin binder such as, for example, crizanlizumab or inclacumab, a pyruvate kinase M2 activator such as, for example, AG348 or FT-4202; a PDE9 inhibitor such as, for example, IMR-687; a stimulator of soluble guanylate cyclase such as, for example, olinciguat; an anti-hepcidin therapy such as, for example, PGT-300 or siRNA-GalNAc, or the like; an iron chelator such as, for example, desferasirox or deferiprone; and combinations thereof.

Aspect 54. The kit of Aspect 52, wherein the second therapeutic agent is selected from a tetrahydrouridine derivative, a 2'-fluorinated tetrahydrouridine derivative, and combinations thereof.

Aspect 55. The kit of Aspect 54, wherein the second therapeutic agent is selected from tetrahydrouridine; 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl)tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone, a pharmaceutically acceptable salt thereof, or combinations thereof.

Aspect 56. The kit of Aspect 54, wherein the second therapeutic agent is a tetrahydrouridine derivative.

Aspect 57. The kit of Aspect 54, wherein the second therapeutic agent is a 2'-fluorinated tetrahydrouridine derivative.

Aspect 58. The kit of Aspect 54, wherein the second therapeutic agent is a 2'-fluorinated tetrahydrouridine derivative; and wherein the 2'-fluorinated tetrahydrouridine derivative is selected from 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl)tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone.

Aspect 59. The kit of any one of Aspect 45-Aspect 58, wherein the hematological disorder comprises sickle cell disease or thalassemia or anemia or blood cancer.

Aspect 60. The kit of any one of Aspect 45-Aspect 59, wherein the first therapeutic agent and the second therapeutic agent are present in the kit as the pharmaceutical composition of any one of Aspect 1-Aspect 18.

Aspect 61. The kit of any one of Aspect 45-Aspect 60, wherein the first therapeutic agent and the second therapeutic agent are administered sequentially or simultaneously.

Aspect 62. The kit of any of Aspect 45-Aspect 61, wherein the subject is a human.

Aspect 63. The kit of any of Aspect 45-Aspect 62, wherein the first therapeutic agent further comprises at least one at least one pharmaceutically acceptable excipient.

Aspect 64. The kit of Aspect 63, wherein the at least one pharmaceutically acceptable excipient comprises mannitol, microcrystalline cellulose, crospovidone, or magnesium stearate.

Aspect 65. The kit of any of Aspect 45-Aspect 64, wherein the second therapeutic agent further comprises at least one at least one pharmaceutically acceptable excipient.

Aspect 66. The kit of Aspect 65, wherein the at least one pharmaceutically acceptable excipient comprises mannitol, microcrystalline cellulose, crospovidone, or magnesium stearate.

Aspect 67. The kit of any of Aspect 45-Aspect 66, wherein the second pharmaceutical agent is administered as an enteric coated, stomach or gastric acid stable formulation.

Aspect 68. The kit of any of Aspect 45-Aspect 67, wherein the first therapeutic agent is administered in an amount of from about 1 mg to about 50 mg in a single dosage form.

Aspect 69. The kit of any of Aspect 45-Aspect 68, wherein the first therapeutic agent is administered orally.

Aspect 70. The kit of Aspect 69, wherein the first therapeutic agent is administered orally as a dosage form comprising a layered tablet, a tablet-in-tablet form, a tablet-in-capsule form, or a capsule-in-capsule form, granule, powder in sachet or bag, capsule, tablet, pill, or other oral solid dosage form.

Aspect 71. The kit of any of Aspect 45-Aspect 70, wherein the second therapeutic agent is administered in an amount of from about 100 to about 600 mg/m$^2$ in a single dosage form.

Aspect 72. The kit of any of Aspect 45-Aspect 71, wherein the second therapeutic agent is bioavailable from about 1 to about 60 minutes before the first therapeutic agent.

Aspect 73. The kit of any of Aspect 45-Aspect 72, wherein the second therapeutic agent is administered orally.

Aspect 74. The kit of Aspect 73, wherein the use for oral administration has a dosage form comprising a layered tablet, a tablet-in-tablet form, a tablet-in-capsule form, or a capsule-in-capsule form, granule, powder in sachet or bag, capsule, tablet, pill, or other oral solid dosage form.

Aspect 75. The kit of any of Aspect 45-74, wherein the first therapeutic agent and the second therapeutic agent are formulated as a fixed dose combination.

Aspect 76. The kit of any of Aspect 45-75, wherein the first therapeutic agent is formulated as a first use and the second therapeutic agent is formulated as a second use.

Aspect 77. Product for use in the treatment of a hematological disorder, a disorder requiring increased expression of fetal hemoglobin, and/or a disease associated with abnormal cellular proliferation, e.g., a cancer; the product comprising (a) a first therapeutic agent and optionally a second therapeutic agent; wherein the first therapeutic agent is a compound of Formula I, a pharmaceutically acceptable salt thereof, or combinations thereof; and wherein, when present, the optional second therapeutic agent is tetrahydrouridine, a 2'-fluorinated tetrahydrouridine derivative, a pharmaceutically acceptable salt thereof, or combinations thereof; or (b) the pharmaceutical composition of any one of Aspects 1-18.

Aspect 78. The product of Aspect 77, wherein the hematological disorder is selected from sickle cell disease, thalassemia, anemia, blood cancer, and combinations thereof.

Aspect 79. The product of Aspect 77 or Aspect 78, further comprising administrating a gene therapy product including, but not limited to, ZYNTEGLO®, ARU-1801, EDIT-301, ST-400, CTX001, ET-01, or a combination thereof.

Aspect 80. The product of any one of Aspect 77-79, wherein the first therapeutic agent is selected from 5-aza-4'-thio-2'-deoxycytidine, 5-fluoro-2'-deoxycytidine, a pharmaceutically acceptable salt thereof, and combinations thereof.

Aspect 81. The product of any one of Aspect 77-Aspect 80, wherein the first therapeutic agent has the following structure:

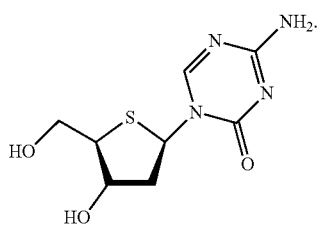 [SMILES: Nc1ncn([C@H]2C[C@@H](O)[C@@H](CO)S2)c(=O)n1]

Aspect 82. The product of any one of Aspect 77-Aspect 80, wherein the first therapeutic agent has the following structure:

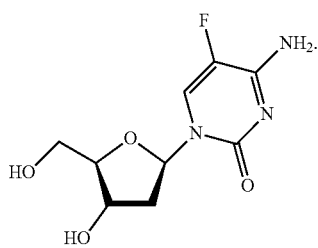 [SMILES: Nc1nc(=O)n([C@H]2C[C@@H](O)[C@@H](CO)O2)cc1F]

Aspect 83. The product of any one of Aspect 77-Aspect 81, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity a P-selectin binder; a pyruvate kinase M2 activator; a PDE9 inhibitor; a stimulator of soluble guanylate cyclase; an anti-hepcidin therapy; an iron chelator; a tetrahydrouridine derivative; a 2'-fluorinated tetrahydrouridine derivative; a pharmaceutically acceptable salt thereof, and combinations thereof.

Aspect 84. The product of Aspect 83, wherein the second therapeutic agent is selected from at least one HDAC (histone deacetylase) inhibitor; a PD1 inhibitor; a Janus kinase (JAK) inhibitor; a hydroxyurea analog; a hemoglobin oxygen-affinity such as Voxelotor (GBT440); AN-233; a P-selectin binder such as, for example, crizanlizumab or inclacumab, a pyruvate kinase M2 activator such as, for example, AG348 or FT-4202; a PDE9 inhibitor such as, for example, IMR-687; a stimulator of soluble guanylate cyclase such as, for example, olinciguat; an anti-hepcidin therapy such as, for example, PGT-300 or siRNA-GalNAc, or the like; an iron chelator such as, for example, desferasirox or deferiprone; a tetrahydrouridine derivative, a 2'-fluorinated tetrahydrouridine derivative; a pharmaceutically acceptable salt thereof, and combinations thereof.

Aspect 85. The product of Aspect 83, wherein the second therapeutic agent is selected from a tetrahydrouridine derivative, a 2'-fluorinated tetrahydrouridine derivative; a pharmaceutically acceptable salt thereof, and combinations thereof.

Aspect 86. The product of Aspect 84, wherein the second therapeutic agent is selected from tetrahydrouridine; 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl)tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone; a pharmaceutically acceptable salt thereof, and combinations thereof.

Aspect 87. The product of Aspect 84, wherein the second therapeutic agent is a tetrahydrouridine derivative.

Aspect 88. The product of Aspect 84, wherein the second therapeutic agent is a 2'-fluorinated tetrahydrouridine derivative.

Aspect 89. The product of Aspect 84, wherein the second therapeutic agent is a 2'-fluorinated tetrahydrouridine derivative; and wherein the 2'-fluorinated tetrahydrouridine derivative is selected from 2'-Deoxy-2',2'-difluoro-5,6-dihydrouridine; (4R)-2'-Deoxy-2',2'-difluoro-3,4,5,6-tetrahydrouridine; (4S)-2'-Deoxy-2',2'-difluoro-3,4,5,6-tetrahydrouridine; 1-(2-Deoxy-2,2-difluoro-β-D-erythro-pentofuranosyl)-tetrahydro-2(1H)-pyrimidinone; 2'-Deoxy-2'-fluoro-5,6-dihydrouridine; (4R)-2'-Deoxy-2'-fluoro-3,4,5,6-tetrahydrouridine; (4S)-2'-Deoxy-2'-fluoro-3,4,5,6-tetrahydrouridine; 1-(2-Deoxy-2-fluoro-(3-D-ribofuranosyl)tetra-hydro-2(1H)-pyrimidinone; 1-(2-Deoxy-2-fluoro-β-D-arabinofuranosyl)dihydro-2,4-(1H, 3H)-pyrimidinedione; (4R)-1-(2-Deoxy-2-fluoro-(3-D-arabinofuranosyl)tetrahydro-4-hydroxy-2(1H)-pyrimidinone; (4S)-1-(2-Deoxy-2-fluoro-(3-D-arabinofuranosyl)tetrahydro-4-hydroxy-2(1H)-pyrimidinone.

Aspect 89. The product of any one of Aspect 77-Aspect 89, wherein the first therapeutic agent and the second therapeutic agent are administered as the pharmaceutical composition of any one of Aspect 1-Aspect 18 to the subject.

Aspect 90. The product of any one of Aspect 77-Aspect 89, wherein the first therapeutic agent and the second therapeutic agent are administered sequentially or simultaneously.

Aspect 91. The product of any of Aspect 77-Aspect 90, wherein the subject is a human.

Aspect 92. The product of any of Aspect 77-Aspect 91, wherein the first therapeutic agent further comprises at least one at least one pharmaceutically acceptable excipient.

Aspect 93. The product of Aspect 92, wherein the at least one pharmaceutically acceptable excipient comprises mannitol, microcrystalline cellulose, crospovidone, or magnesium stearate.

Aspect 94. The product of any of Aspect 77-Aspect 93, wherein the second therapeutic agent further comprises at least one at least one pharmaceutically acceptable excipient.

Aspect 95. The product of Aspect 37, wherein the at least one pharmaceutically acceptable excipient comprises mannitol, microcrystalline cellulose, crospovidone, or magnesium stearate.

Aspect 96. The product of any of Aspect 77-Aspect 95, wherein the second pharmaceutical agent is administered as an enteric coated, stomach or gastric acid stable formulation.

Aspect 97. The product of any of Aspect 77-Aspect 96, wherein the first therapeutic agent is administered in an amount of from about 1 mg to about 50 mg in a single dosage form.

Aspect 98. The product of any of Aspect 77-Aspect 97, wherein the first therapeutic agent is administered orally.

Aspect 99. The product of Aspect 98, wherein the first therapeutic agent is administered orally as a dosage form comprising a layered tablet, a tablet-in-tablet form, a tablet-in-capsule form, or a capsule-in-capsule form, granule, powder in sachet or bag, capsule, tablet, pill, or other oral solid dosage form.

Aspect 100. The product of any of Aspect 77-Aspect 99, wherein the second therapeutic agent is administered in an amount of from about 100 to about 600 mg/m² in a single dosage form.

Aspect 101. The product of any of Aspect 77-Aspect 100, wherein the second therapeutic agent is bioavailable from about 1 to about 60 minutes before the first therapeutic agent.

From the foregoing, it will be seen that aspects herein are well adapted to attain all the ends and objects hereinabove set forth together with other advantages which are obvious, and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and sub-combinations are of utility and may be employed without reference to other features and sub-combinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Synthesis of Compounds

Compounds of the present disclosure can be prepared according to methods described in Tiwari, K. N. et al., "Synthesis and anti-cancer activity of some novel 5-azacytosine nucleosides," Nucleosides Nucleotides Nucleic Acids, 2003, 22:2161-2170, Secrist, J. A. et al., "Synthesis and biological activity of 2'-deoxy-4'-thio pyrimidine nucleosides," J. Med. Chem., 1991, 34:2361-2366, U.S. Pat. No. 5,591,722 to Montgomery et al., European Patent 0 421 777 to Walker et al., and international patent application publication WO 2019152459 to Morris et al., each of which is incorporated herein by reference.

The following scheme illustrates synthesis of 5-aza-2'-deoxy-4'-thio cytidine and can be applied to other cytidine analogs using appropriate starting materials. Protecting groups can be removed by any method known in the art.

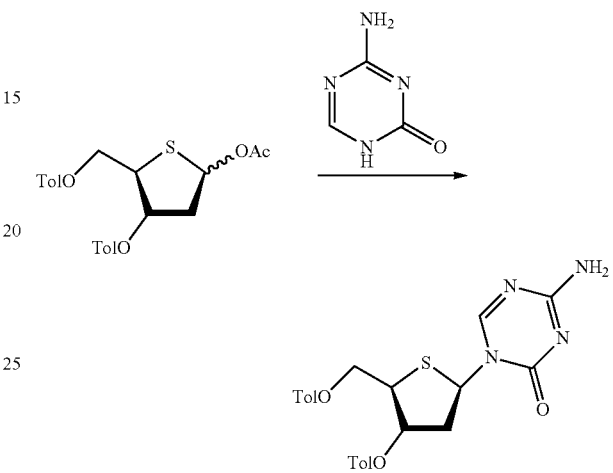

Example 2: Formulations

Example formulations for delivering the compounds disclosed herein are provided below.

Capsule Composition

An oral dosage form for administering a compound as disclosed herein is produced by filling a standard two-piece hard gelatin capsule with ingredients as follows: active compound 7 mg, lactose 53 mg, talc 16 mg, magnesium stearate 4 mg.

Injectable Parenteral Composition

An injectable form for administering a compound as disclosed herein is produced by stirring 1.7% by weight of active compound in 10% by volume propylene glycol in water.

Tablet Composition

A tablet is prepared with the following ingredients: 12 mg of active compound, 30 mg of calcium sulfate dihydrate, 4 mg sucrose, 2 mg starch 1 mg talc, and 0.5 mg stearic acid. Sucrose, calcium sulfate dihydrate, and active compound are mixed and granulated in the proportions shown with a 10% gelatin solution. Wet granules are screened, dried, mixed with starch, talc, and stearic acid, screened again, and compressed into a tablet.

Figure 5B:
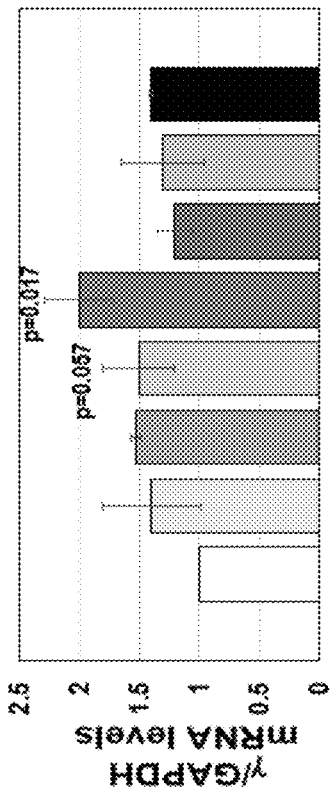
FIGS. 5A-5D show representative data for various aspects of treatment of K562 cells with control and disclosed compounds.
Figure 5D:
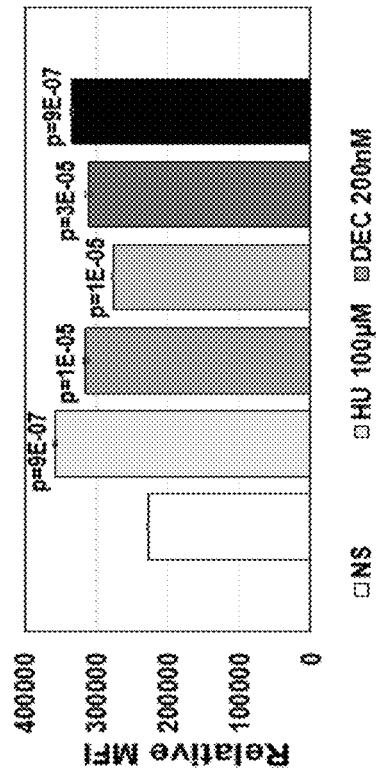
Figure 5A:
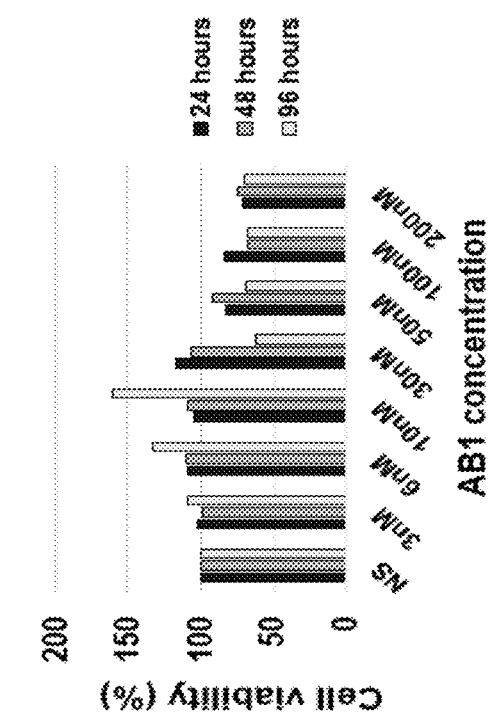
Figure 5C:
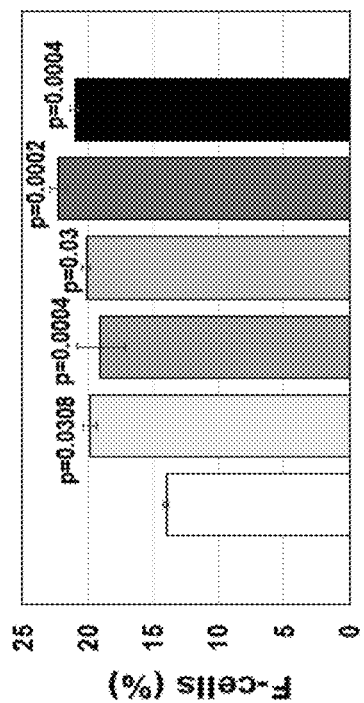

Example 3: In Vitro Studies in Elevation of HbF by AB1 in Sickle Cell Disease Progenitors Studies were carried out to evaluate AB1 in SCD mouse studies, in vitro experiments were conducted to establish the ability of AB1 to induce HbF using K562 cells and sickle primary erythroid progenitors. Screening studies in K562 cells, grown in Iscove's Modified Dulbecco Media (IMDM) and 10% fetal bovine serum at 37° C., 5% $CO_2$ for 24-96 hours, tested a dose range of 3-200 nM AB1. As shown in FIG. 5A, AB1 was tolerated without toxicity at 3, 6, and 10 nM; in fact, cell growth was stimulated at 96 hours. At 50-200 nM AB1, cell growth inhibition occurred at all time points. To study γ-globin gene transcription, reverse transcriptase-quantitative PCR (RT-qPCR) was conducted as previously published. See Biaoru Li, et al. *MIR-144-mediated NRF2 gene silencing inhibits fetal hemoglobin expression in sickle cell disease* Experimental Hematology 2019; 70:85-96, incorporated by reference herein. γ/GAPDH mRNA increased the greatest at treatment levels of 6 and 10 nM AB1 (FIG. 5B). It was next determined if the activation of the γ-globin gene was associated with an increase in HbF expression by established flow cytometry methods (i.e., see Biaoru Li, et al. *Fetal hemoglobin induction in sickle erythroid progenitors using a synthetic zinc finger DNA-binding domain* Haematologica 2018; 103:e384, incorporated herein by reference. The data show that AB1 increased the percent of HbF positive cells (F-cells) and the level of HbF protein per cell was measured by mean fluorescence intensity (MFI) at highly significant p values (FIGS. 5C-5D). It should be noted that HbF induction by AB1 was at least as good as that induced by control drugs HU (100 μM) and Dec 200 nM. Moreover, although 50 nM AB1 may be somewhat cytotoxic under the conditions of this study with these cells, nevertheless, HbF expression increased. These studies in K562 cells show that AB1 induces HbF in erythroid cells at low concentration.

Figure 6C:
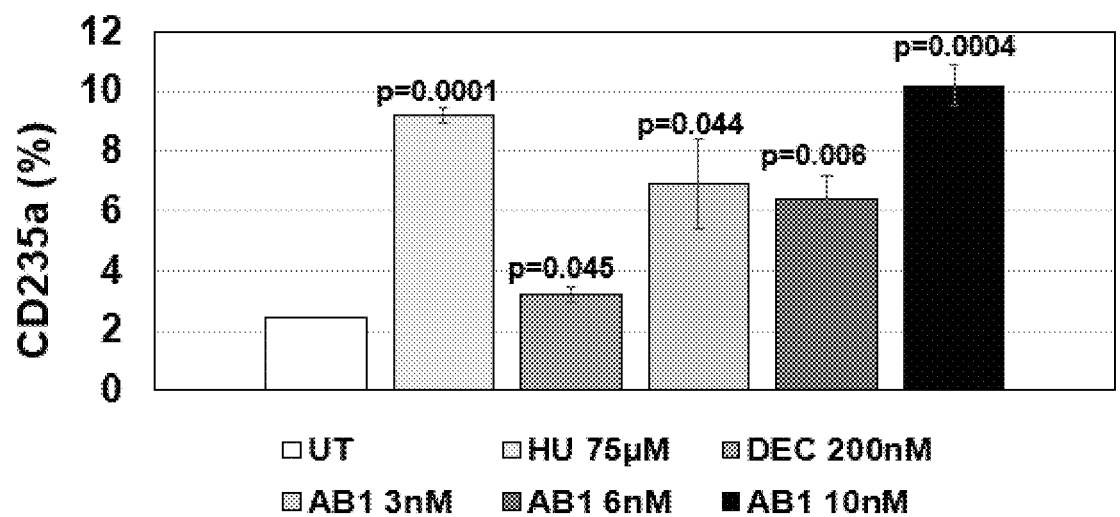
FIGS. 6A-6B show representative data pertaining to primary sickle erythroid progenitors generated from peripheral blood mononuclear cells isolated from sickle cell patients using a two-phase liquid culture system. Cells treated for 48 hours were analyzed.

Example 4: AB1 Induces HbF Expression and Reduce Sickling in Primary Sickle Erythroid Cells The foregoing studies demonstrate that AB1 activates γ-globin transcription in K562 cells. Additional studies were carried out in primary sickle erythroid progenitors were next conducted. Using a previously established two-phase culture system, (See *NRF2 mediates γ-globin gene regulation and fetal hemoglobin induction in human erythroid progenitors* Xingguo Zhu et al., Experimental Hematology 2019; 70:85-96, incorporated by reference herein) AB1 was evaluated in progenitors cultured from peripheral blood mononuclear cells (PBMC) isolated from sickle cell subjects, at concentrations of 3, 6, and 10 nM. PBMCs were isolated by Ficoll® Paque separation and cultured in IMDM supplemented with erythropoietin (2 IU), stem cell factor (10 ng/mL) and Interleukin 3 (10 ng/mL). On day seven, drug controls HU 75 μM, Dec 200 nM and AB1 (3, 6, and 10 nM) were added for 48 hours. Cell viability was assessed with Trypan blue, and markers of erythroid differentiation were assessed by flow cytometry using antibodies for CD71 and CD235a, to evaluate changes in differentiation. Proportions of F-cells and MFI were assayed by FACScan using staining with fluorescein isothiocyanate (FITC) anti-human HbF antibody (Bethyl). In our experience, primary erythroid progenitors are more sensitive to drug toxicity, so a lower dose range of AB1 was used. As shown in FIG. 6A, it can be observed that there was a 20%-22% drop in cell viability at the AB1 6 and 10 nM concentrations, compared with a 40% drop in viability produced by HU. It should be noted that AB1 at 3 nM actually appeared to enhance cell viability. As a marker of early erythroid differentiation, CD71$^+$ progenitors were not affected by Dec or AB1 at any dose tested. In notable contrast, there was a 7-fold increase in CD71$^+$ cells mediated by HU (FIG. 6B). In contrast, the level of CD235a$^+$ cells (a marker of terminal differentiation) were significantly increased by all drugs except Dec (FIG. 6C).

Figure 7A:
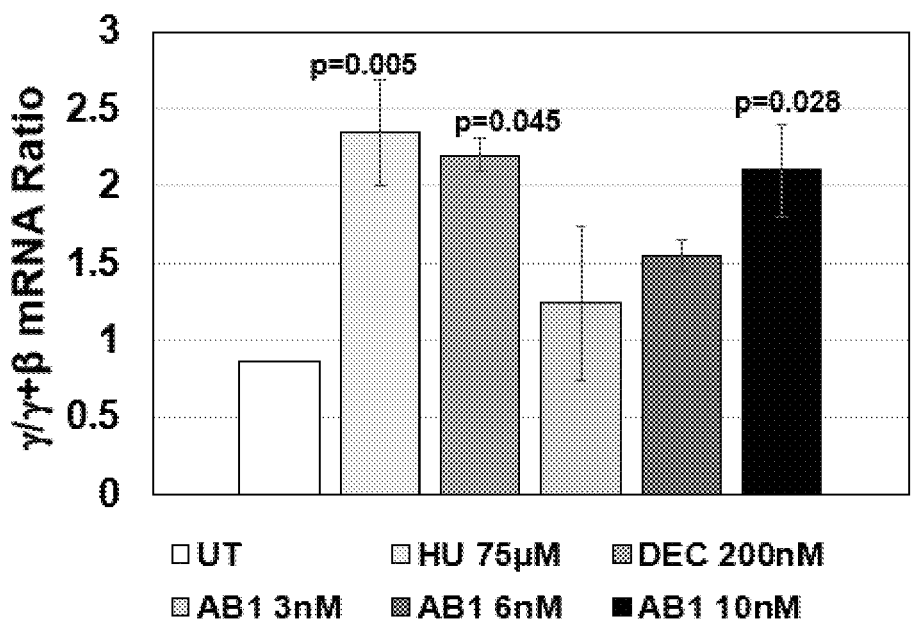
FIGS. 7A-7B show representative data pertaining to the activation of γ-globin gene transcription was produced by disclosed compound AB1. Sickle erythroid progenitors were treated with the various agents shown for 48 hours.
Figure 7B:
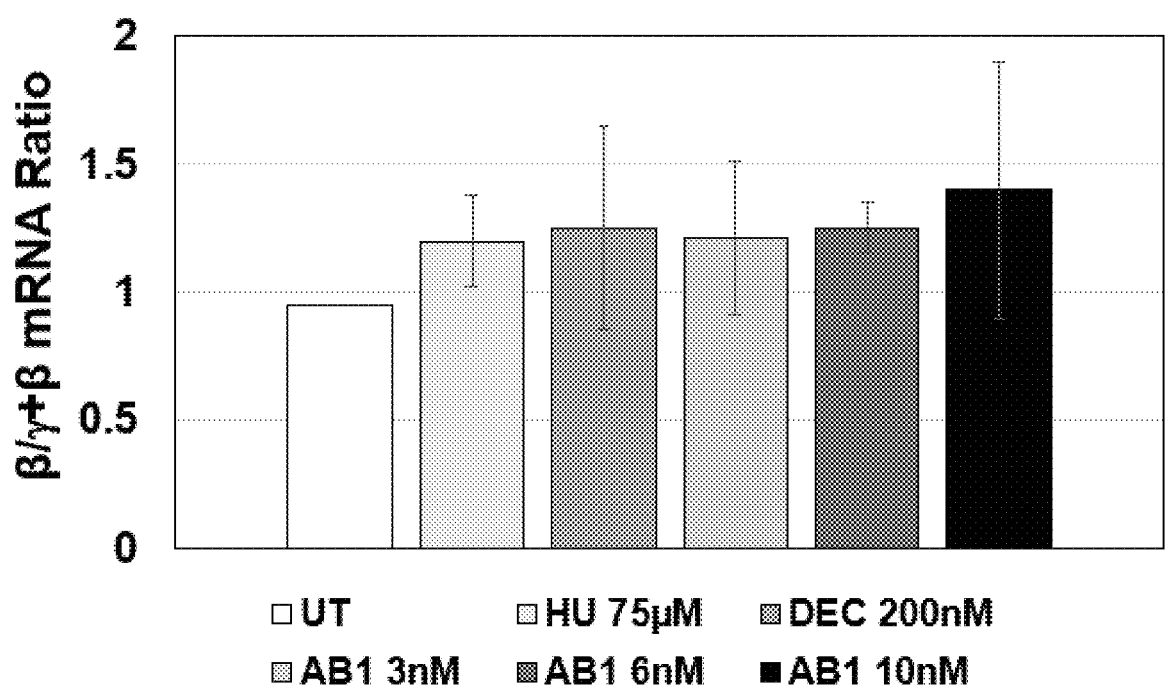
Figure 8A:
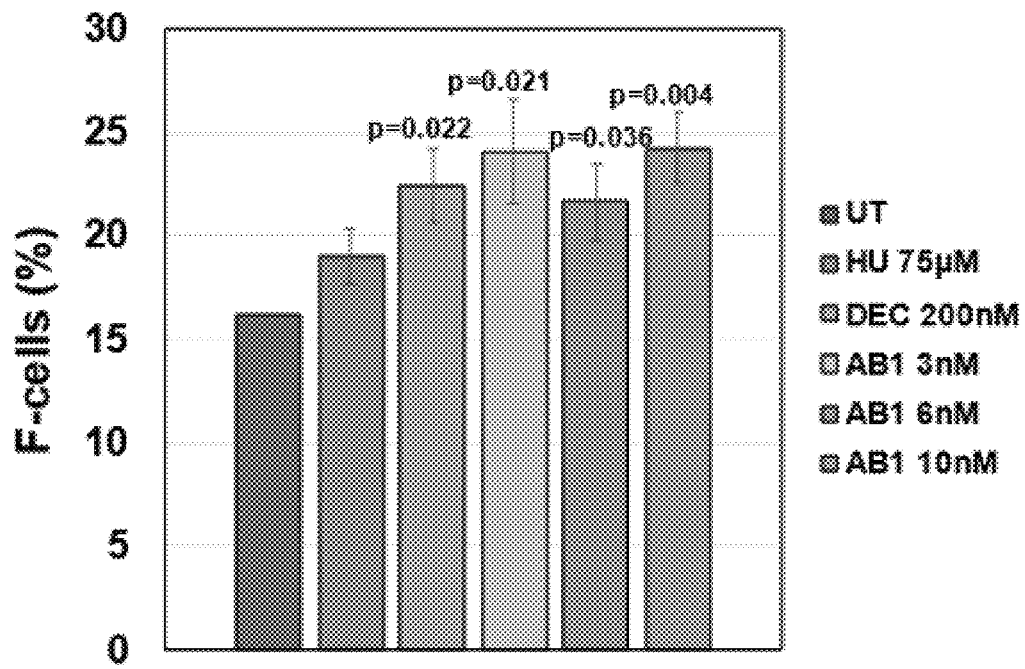
FIGS. 8A-8D show representative data pertaining to the induction of AB1 HbF and inhibition of DNMT1 levels. Sickle erythroid progenitors were treated with the various agents shown for 48 hours.
Figure 8B:
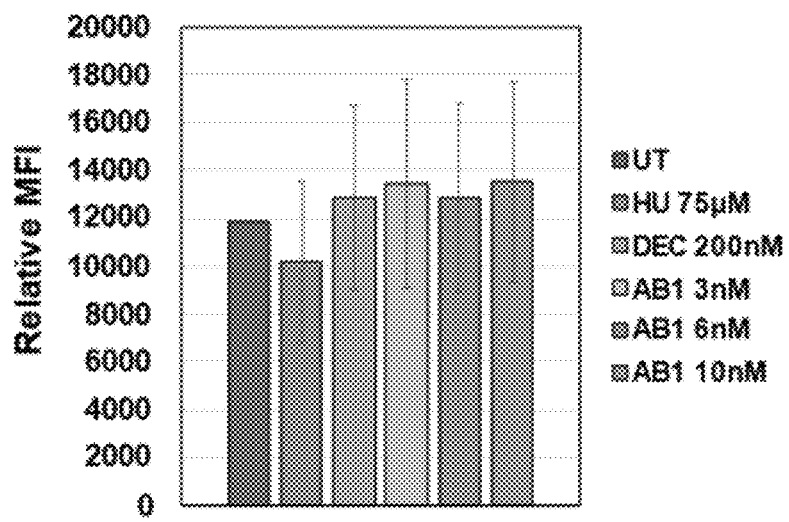
Figure 8C:
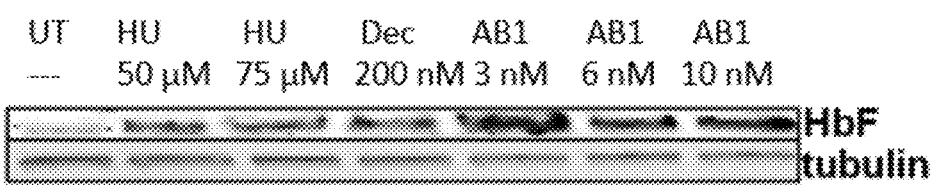
Figure 8D:
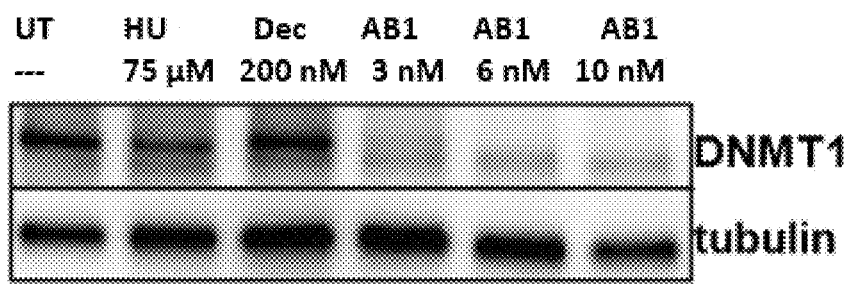
Figure 9A:
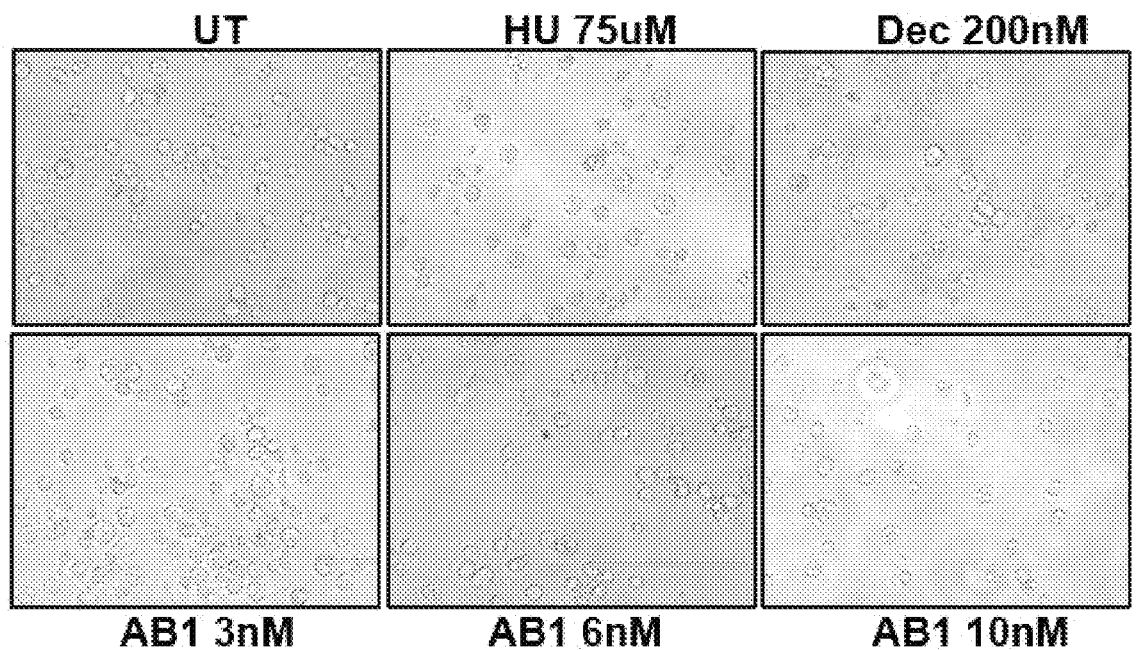
FIGS. 9A-9B show representative data pertaining to various treatments and reduction of the level of sickle erythroid progenitors. After sickle progenitors were treated with the various drugs for 48 hours as indicated, and then incubated overnight in hypoxia conditions.
Figure 9B:
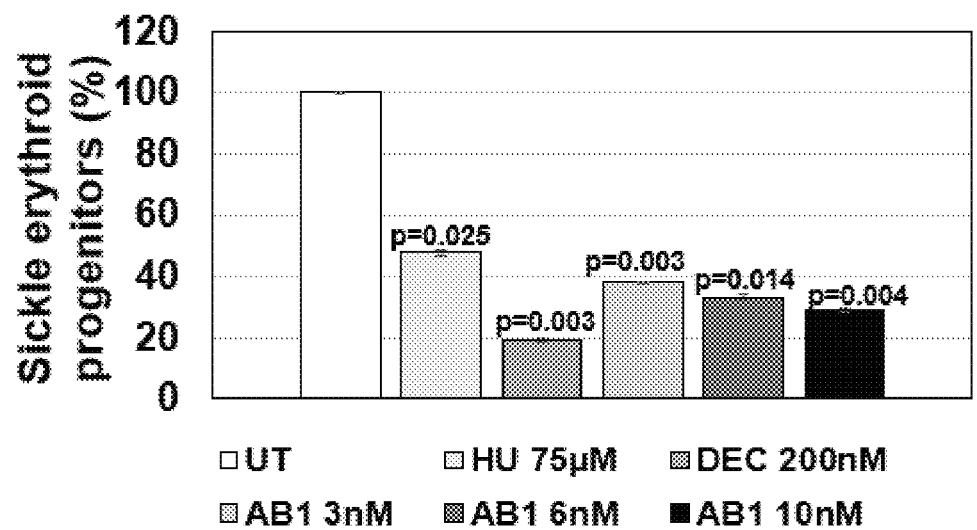

DISCUSSION OF EXAMPLES 3 AND 4: These findings suggest that AB1 does not cause a delay in erythroid maturation but, instead, supports terminal differentiation, while HU affects early erythroid progression. We assessed effects of AB1 at the transcription levels by RT-qPCR analysis. A dose-dependent maximal 3.5-fold increase (p=0.028) in γ/γ+β mRNA was produced by AB1 at 3, 6, and 10 nM without affecting β/γ+β mRNA levels (FIGS. 7A-7B), supporting preferential activation of γ-globin by AB1. Complementary studies at the protein levels were completed by flow cytometry and Western blot. Among the SCD patients tested, F-cell levels increase from 16% to 23%, on average, at all AB1 concentrations tested (FIG. 8A) comparable to that produced by Dec (22% F-cells). Interestingly, when all patient data were combined, F-cell induction was not observed with HU. The increases in MFI were observable, but did not reach statistical significance in these specific studies, although it is believed that statistical significance can be obtained in a larger sample size (FIG. 8B). To further support the notion that AB1 induces HbF expression, Western blot analysis was performed. As shown in FIG. 8C, it was observed that HbF was induced at all concentrations of AB1 tested, confirming efficacy in sickle erythroid progenitors. Interestingly, AB1 at 3 nM produced the highest HbF induction with the data showing at a 13.8-fold increase. In contrast, there were no significant changes in HbS expression observed in this study. Previous studies demonstrated the ability of AB1 to inhibit DNMT1 in tumor tissue. It was observed that there was a dose-dependent 80% decrease in DNMT1 in sickle erythroid progenitors at the highest AB1 10 nM concentration (FIG. 8 D). It was of interest to demonstrate whether the increase in HbF produced by AB1 was able to produce a phenotypic change in HbS polymerization and in vitro sickling in erythroid progenitors, and accordingly, hypoxia studies were carried out under conditions of overnight hypoxia. After treatment for 48 hours, with the various drugs, the cells were incubated overnight at 2% oxygen, then fixed with formalin and the number of sickle versus non-sickle cells counted by phase contrast microscopy, a method previously published by the Pace (PI/PD) group (see Zhu, X., Li, B. & Pace, B. S. Haematologica 102, e285-e288, doi:10.3324/haematol.2016.160788 (2017)). Representative images and quantitative data obtained from the image data are shown in FIGS. 9A-9B. The data show a notable decrease of 60% to 83% in sickle cells treated with AB1, which was comparable to the 80% decrease observed by treatment with decitabine. In contrast, there was only a 50% decrease achieved by treatment with HU.

Example 5: AB1 Induces HbF Expression in Human Subjects

Figure 10:
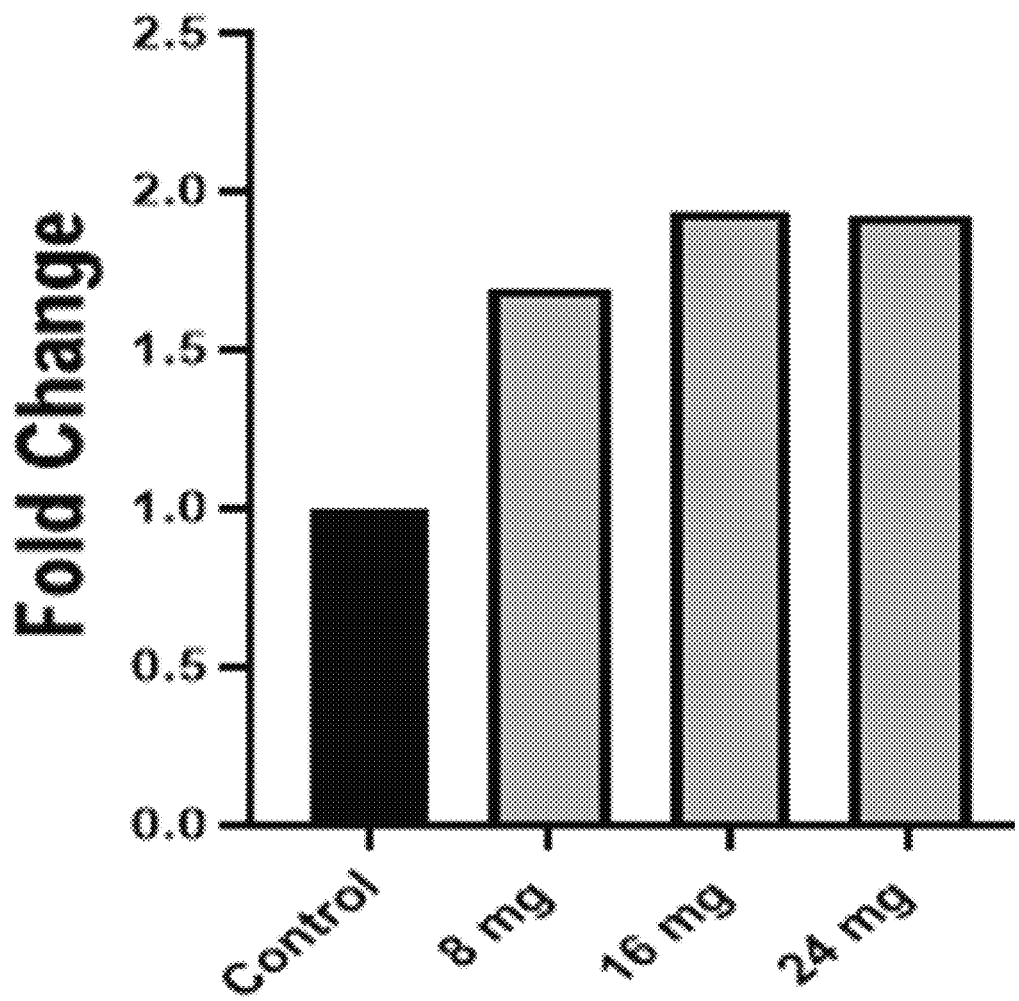
FIG. 10 shows representative data obtained in a clinical study with human subjects treated with the disclosed compound AB1. The determination of Fetal Hemoglobin was made after two weeks of AB1 treatment at the indicated dosage levels (8 mg, 16 mg, and 24 mg dose as indicated) versus control.

AB1 was dosed in human subjects in an approved clinical trial. Briefly, AB1 was utilized as monotherapy in patients compared to adjuvant therapy or standard of care. In samples isolated from three treated subjects at two weeks of dosing and it was observed that these subjects had measurable increases in HbF levels, and each subject had a two-fold elevation in their HbF levels at the end of two 5-day cycles of 8, 16 or 24 mg AB1 treatment (FIG. 10).

Example 6: Prophetic Example—Effects on Erythroid Progenitor Cells (EPCs) In Vitro Day 7 EPCs are cultured in duplicate plates with serially diluted 2'-deoxycytidine analogs for 5 days at 37° C. Wells are then analyzed for either induction of fetal hemoglobin (HbF, HbF ELISA) or cell growth (Cell Titer-Glo). In both cases, the signal is normalized to vehicle-control treated cells. Ideal candidate compounds induced an increase in HbF with an average $pEC_{50}$ of 6.5 and inhibited cell growth by 50% with an average $pGI_{50}$ of 5.9.

To assay the effect of 2'-deoxycytidine analogs on DNA methylation, EPCs treated for 3 days with representative compounds are harvested and genomic DNA is bisulfite sequenced. Methylation of CpG sites in or near the promoter regions of HBG1 and HBG2 gene loci are selected and analyzed based on previous characterization as sites of DNMT1 methylation during erythropoiesis. All sites showed reduction in methylation, averaging 65±5% decreases compared with vehicle-treated cells. Additional details on the experimental methods used for this assay are provided below.

Methods

All donors provided written informed consent for the use of their samples and the collection and use of samples received institutional review board approval. All cryopreserved human bone marrow CD34+ cells used herein are obtained from AllCells (Emeryville, CA) and are generally from different donors. The CD34+ cells are cultured to generate EPCs at day 7. Approximately 1,000,000 cells are cultured in 5% $CO_2$, 5% $O_2$ at 37° C. in H3000 Stemspan media (StemCell Technologies, Vancouver, BC, Canada) supplemented with 2 mM L-glutamine, 40 μg/mL human low-density lipoproteins (StemCell Technologies), 10 ng/mL recombinant human (rh) interleukin IL-3 (R&D Systems, Minneapolis, MN), 100 ng/mL rh stem cell factor (R&D Systems), and 0.5 U/mL rh erythropoietin (Invitrogen, Grand Island, NY). Cells are split and refed on day 4 with the complete culture media described above and harvested on day 7 for evaluation of erythroid marker expression and assessment of γ-globin induction. Day 7 EPCs are then frozen in liquid nitrogen at 5-10 million cells/mL in 95% fetal bovine serum (FBS; Invitrogen) with 5% DMSO for subsequent use.

At the time of compound treatment, frozen day 7 EPCs prepared as described above are thawed and re-suspended in complete culture media as described above with the exception of an increase of rhEPO to 3 U/mL. Cells are counted and diluted to $3.3 \times 10^3$ cells/mL for plating into assay plates. Cells are then dispensed at 30 μL per well with a Multidrop Combi Reagent Dispenser (Thermo Scientific) into 384-well culture plates into which test compounds had been pre-dispensed at 100 nL/well. Black Clear Bottom (Greiner Bio-One product 781090) and White (Greiner Bio-One product 781080) plates are used for ELISA and Cell Titer-Glo assays, respectively. The final cell density in the assays is 1000 cells per well, with final compound concentrations between 33 nM and 6.6 nM for a 22 point serial dilution.

To monitor cell health and cell growth, cell growth assays are performed at the time of cell plating (day 0) using Cell Titer-Glo (see below). For compound treatment, the cell culture plates are incubated for 5 days at 37° C. with 5% $CO_2$.

Fetal Hemoglobin (HbF) ELISA

Coating anti-HbF Ab (Bethyl Lab, product A80-136A) is diluted 100-fold in the coating buffer (0.05 M carbonate-bicarbonate at pH 9.6) and 20 μL/well is added to a 384-well MaxiSorp ELISA plate (Thermo Fisher product 464718). After 1 h incubation at room temperature, the plates are washed twice with ELISA washing buffer (50 mM Tris and 0.05% polysorbate 20 at pH 8.0) with an EL406 plate washer (BioTek, Winooski, VT). 40 μL/well of blocking buffer (50 mM Tris and 1% BSA at pH 8.0) is added to the plate and stored at 4° C. with cover sheet overnight or until time of the assay. Coated ELISA plates are stable for up to 30 days at 4° C. On the day of the assay, plates are washed twice with ELISA washing buffer prior to addition of cell lysate.

After 5 days at 37° C. with 5% $CO_2$, cell culture plates for the ELISA assay are frozen at −80° C. for a minimum of 2 h. After thawing at room temperature, 30 μL of cell lysis buffer (Invitrogen product FNN0011 supplemented with 1× protease inhibitor) are added to each well and the resulting cell lysate is mixed eight times with a Cybi-Well (Jena, Germany) pipettor. Following the mixing procedure, 20μ/ well of lysate is transferred to the coated ELISA plates described previously, followed by 1 h incubation at room temperature. The ELISA assay plates are then washed three times with ELISA wash buffer. 20 μL per well of 1:75,000 to 100,000 diluted horseradish peroxidase (HRP) conjugate detection anti-HBF Ab (Bethyl Labs product A80-136P, diluted in 50 mM Tris at pH 8.0, 1% BSA, and 0.05% polysorbate 20) is then added. After another 1 h incubation at room temperature, plates are washed four times and 20 μL per well of tetramethyl benzidine ELISA substrate (Thermo Scientific product 34028) are added. After 3-10 min incubation at room temperature in the dark, 20 μL/well of stop solution (0.2 M $H_2SO_4$) are added. The plates are ten read at 450 nm with an Envision plate reader (Perkin Elmer, Waltham, MA). The average reading of the control wells (16 wells in column 6 of each assay plate) containing DMSO only are used as the base level for normalization. The γ-globin level of each compound-treated well is calculated as a percentage of the base level.

The normalized responses of 22 concentrations of each test compound are subjected to curve fitting using a customized statistical computing tool based on R (R Foundation for Statistical Computing). An $EC_{50}$ value (compound concentration at % Max %) and the corresponding Max % are determined from fitted curves for each active compound.

Cell Growth Analysis in Day 7 EPCs

Cell growth assays are performed on cell culture plates after days incubation at 37° C. with 5% $CO_2$. 15 μL per well of Cell Titer-Glo (Promega, Madison, WI) assay reagent is added to the assay plates. The plates are then incubated at room temperature for 10 min prior to reading on a ViewLux 1430 (Perkin Elmer) using a luminescence protocol provided by the manufacturer. The average reading of control wells (16 wells in column 6 of each assay plate) containing DMSO only is used as the base level for normalization. The Cell Titer-Glo signal of each test well is calculated as a percentage of the base level. Normalized responses of the 22 concentrations of each test compound are subjected to curve fitting using a customized statistical computing tool based on R (R Foundation for Statistical Computing).

To monitor cell health and cell growth, the Cell Titer-Glo signal of DMSO control wells is compared to the signal obtained on day 0. For health cell growth, increase of approximately 20× is typically observed at day 5 compared to day 0.

It is anticipated that the disclosed compounds and formulations will show improved fetal hemoglobin inducer effect on erythroid progenitor cells in vitro in the foregoing erythroid progenitor cell assay compared to conventional compounds or formulations.

Example 7: Prophetic Example—Sickle Cell Assays In Vivo

A mouse model of sickle cell disease is used to measure the in vivo efficacy of test compounds shown to have potent in vitro activity in human primary erythroid progenitor cells derived from normal bone marrow or sickle cell patient peripheral blood mononuclear cells.

Methods

Experiments are conducted in accordance with US/UK standards of animal care. Male and female human hemoglobin transgenic mice [B6; 129-Hbatm1(HBA)Tow/Hbbtm2(HBG1,HBB*)Tow/J Mice (Jackson Laboratories, ME)] are approximately 6-8 weeks old and weighed approximately 15-25 g at the initiation of the studies. To the extent possible, groups are sex-balanced and contained 6 mice each.

Experimental Protocol

Mice are administered vehicle (10% DMA/90% PEG400), 10 mg/kg test compound, or 50 mg/kg test compound twice daily (BID) by an oral route 5 days per week over a two-week period. At the end of the dosing period, mice are euthanized by $CO_2$ asphyxiation and blood from the vena cava is collected into EDTA tubes for fetal hemoglobin analysis. % HbF protein is determined by HPLC and % F cells (HbF expressing erythrocytes) is determined by flow cytometry. The mouse monoclonal anti-human HbF antibody conjugated to APC (Life Technologies, Grand Island, NY) is used to identify HbF-expressing erythroid cells. Nuclear dye SYTO™ 16 (Life Technologies) is used to separate the reticulocyte and RBC populations. Protein and cellular data are collected on a Bio-Rad D10 analyzer (Bio-Rad, Benicia, CA) and an FACs Canto I (BD BioSciences, San Jose, CA), respectively. Flow cytometry data is analyzed with Flowjo v8 software, Treestar, Inc., Ashlant, OR). Group mean and standard deviation are determined for the control and treatment groups and data are graphed and analyzed using 1-way ANOVA with Tukey Test (GraphPad Prism v5, La Jolla, CA).

It is anticipated that the disclosed compounds and formulations will show improved fetal hemoglobin inducer effect on erythroid progenitor cells in vitro in the foregoing sickle cell assay compared to conventional compounds or formulations.

Example 8: Prophetic Example—Additional Assays—Tissue Culture and In Vivo Models The following assays and model systems, e.g., tissue culture and/or in vivo models, can be used to assess safety and efficacy of the disclosed compounds and formulations as fetal hemoglobin inducer which are anticipated to provide improved outcomes in these assays compared to conventional compounds or formulations.

Tissue Culture and Reagents

K562 cells are cultured in Iscove's Modified Dulbecco medium (IMDM) with 10% fetal bovine serum, penicillin (100 U/mL) and streptomycin (0.1 mg/mL). Drug inductions for K562 cells are conducted for 48 h and cell viability evaluated with 0.4% Trypan blue exclusion. Cell counts are performed a dual chamber apparatus and the percentage viability obtained using an Automated Cell Counter (Bio-Rad).

For primary cultures, erythroid precursors are generated from peripheral blood mononuclear cells isolated from discard blood of sickle cell patients under an IRB-exempt protocol. These cells are cultured in a two-phase liquid culture system that has been previously published. During phase 1, cells are grown in Iscove's Dulbecco Media with 15% fetal bovine serum, 15% human AB serum, 10 ng/mL interleukin 3, 50 ng/mL stem cell factor, and 2 IU/mL of erythropoietin (Peprotech, Rocky Hill NJ). Phase 2 of culture initiated on day 7 with a similar medium without stem cell factor or interleukin 3. On day 8, erythroid precursors are treated with AN-233 (0.125 mM and 0.25 mM), ethanol (EtOH; 0.0008% and 0.016%) and the positive control HU (100 μM) for 48 h and harvested for the various analyses.

Reverse Transcription-Quantitative PCR (RT-qPCR) Analysis

Total RNA is extracted from cells using Trizol (Ambion, Carlsbad CA) and analyzed by RT-qPCR using a previously published procedure. Gene-specific primers are used to quantify mRNA levels for γ-globin, β-globin, and an internal control of glyceraldehyde-3-phosphate de-hydrogenase (GAPDH). All mRNA levels are normalized to GAPDH before analysis.

Western Blot Analysis

Western blot analysis is performed according to a previously published procedure using whole cell lysates generated with RIPA buffer (ThermoScientific, Rockford, IL) supplemented with proteinase and phosphatase inhibitor cocktails. For histone acetylation studies, nuclear lysates are prepared by suspending cells in buffer containing 20 mM HEPES, pH 7.9, 50 mM KCl, 420 mM NaCl, 0.1 mM EDTA, 1 mM DTT, 10% glycerol and protease inhibitor mixture for 30 min, followed by centrifugation. Antibodies against HbF (51-7), HbA (37-8), and Tata binding protein (TBP; N-12) are purchased from Santa Cruz Biotechnology (Dallas TX); antibodies against β-actin (A5316) and rabbit IgG (18140) are purchased from Sigma (St. Louis MO). Acetylated histone H3 (AcH3; 06-599) and AcH4 (06-866) antibodies are purchased from Millipore (Burlington, MA).

Flow Cytometry Analysis

To measure percent HbF positive cells (F-cells), K562 cells and erythroid precursors are fixed with 1% formaldehyde, permeabilized with ice-cold acetone:methanol (4:1 ratio) and stained with fluorescein isothiocyanate (FITC) anti-HbF antibody (ab19365, Abcam Cambridge MA), while isotype control IgG antibody (MBS524511, MyBioSource, San Diego CA) is used to detect non-specific staining. The F-cells levels and HbF protein levels measured by mean fluorescence intensity (MFI) are analyzed on an LSR-II flow cytometer (BD Biosciences, San Jose CA) and by FlowJo analysis to generate quantitative data.

Heme Quantitation Assay

The total cellular heme content is determined using the QuantiChrom™ Heme Assay Kit (DIHM-250, BioAssay Systems, Hayward, CA) per the manufacturer's instructions. Briefly, 25 μL of cellular lysate is mixed with 100 μL of detection reagent. The mixture is incubated at room temperature for 5 min followed by measuring the absorbance at 400 nm on a microplate reader. The total heme concentration is calculated based on a formula provided by the manufacturer: Heme concentration=$(OD_{sample}-OD_{blank})$ $(OD_{calibrator}-OD_{blank})\times 125\times$ dilution factor. This value is normalized by total protein in each sample.

Sickling Assay

In vitro sickling studies are conducted according to a previously published procedure. Briefly, after drug inductions of sickle erythroid precursors for 48 h, cells are incubated in 2% oxygen overnight and then fixed with 2% formaldehyde. Erythroid morphology is evaluated microscopically and the number of sickled cells per high power field manually counted for 1000 cells, per triplicates per condition.

β-YAC Transgenic Mouse Treatment Protocol

The β-YAC is a transgenic mouse model containing the full-length 81 kb human β-globin gene locus including the LCR and surrounding region. The five functional human globin genes 5'-ε-Gγ-Aγ-δ-β-3' are present and undergo normal developmental regulation with the γ-globin gene silenced shortly after birth. β-YAC mice (5-6 months old) are administered AN-233 suspended in water (200 or 300 mg/kg) 5 days/week for 4 weeks by intraperitoneal injection; we treated five mice per group with 3 males and 2 females. Hydroxyurea (100 mg/kg) is included as a positive control. We collected blood by tail bleed at week 0, 2 and 4 and analyzed for automated complete blood counts with differential using a Micros 60 machine (HORIBA Medical/ABX Diagnostics). The level of F-cells and MFI are performed by flow cytometry as previously described. For reticulocyte counts, whole blood is stained with acridine orange and flow cytometry performed on an LSR-II flow cytometer (BD Biosciences).

α-Globin and Hemoglobin Determination

Cell lysates are run on SDS-PAGE as previously described (Berkovitch et al., 2008). Following blocking, the membranes are incubated with rabbit anti-hemoglobin (Dako, Glostrup, Denmark), rabbit anti-PBGD (a generous gift from HemeBiotech, Sweden). The membranes are washed with PBS-Tween and incubated with horseradish peroxidase (HRP)-tagged anti-mouse secondary anti-body (Jackson ImmunoResearch Labs Inc., West Grove, PA, USA) in the same solution used for blocking. The ratio of the protein level is normalized to HRP-conjugated mouse anti-β-actin (Santa Cruz Biotechnology, Santa Cruz, CA, USA). Immunoreactive proteins are visualized with the EZ-ECL-enhanced chemiluminescence detection kit according to the manufacturer's protocol (Biological Industries).

For hemoglobin determination, the cells are grown in the presence of inducing agents, pelleted by low-speed centrifugation, and washed twice with PBS. The washed cell pellets are then resuspended in an equal volume of distilled water. Cells are lysed by 3 cycles of freeze-thawing and centrifuged once at 2000 rpm for 10 min and again at 15,000 rpm for 45 min. The visible absorbance spectrum of the supernatant is recorded from 417 nm to 700 nm using a Epoch™ Microplate Spectrophotometer (Bio-Tek, US). Relative hemoglobin concentration of 5×17 cell lysates is measured at 540 nm.

Intracellular Heme Measurement

Following treatments, 500 μg of cell lysate are added to 100 μL ortho-toluidine reagent, 0.25 g ortho-toluidine (Sigma-Aldrich, Rehovot, Israel) and dissolved in 80 mL glacial acetic acid and 10 mL dd $H_2O$. After mixing, dd $H_2O$ is added to a final volume of 100 mL. Heme is oxidized to a green product by adding 100 μL of 1.2% $H_2O_2$ to the mixture and incubating for 10 min in the dark. The first oxidation product is then further oxidized to a yellow product by adding 1 mL of a 1:10 v/v diluted acetic acid.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for treating a hematological disorder in a subject, the method comprising:
orally administering a first therapeutic agent to the subject in a regimen for treating the hematological disorder, wherein the first therapeutic agent is 5-aza-4'-thio-2'-deoxycytidine, or a pharmaceutically acceptable salt thereof,
wherein the regimen for treating the hematological disorder does not include administering a cytidine deaminase inhibitor to the subject, and
wherein the hematological disorder is sickle cell disease or thalassemia.

2. The method of claim 1, wherein the hematological disorder comprises sickle cell disease.

3. The method of claim 1, wherein the subject is a human.

4. The method of claim 1, wherein the first therapeutic agent has the following structure:

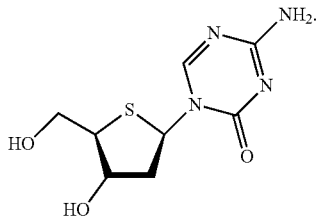 [SMILES: Nc1ncn([C@H]2C[C@@H](O)[C@@H](CO)S2)c(=O)n1]

5. The method of claim 1, wherein the first therapeutic agent is administered in an amount of from about 1 mg to about 50 mg in a single dosage form.

6. The method of claim 1, wherein the first therapeutic agent is administered orally as a dosage form comprising a layered tablet, a tablet-in-tablet form, a tablet-in-capsule form, a capsule-in-capsule form, granule, powder in sachet or bag, capsule, tablet, or pill.

7. The method of claim 1, wherein the first therapeutic agent further comprises at least one pharmaceutically acceptable excipient.

8. The method of claim 7, wherein the at least one pharmaceutically acceptable excipient comprises mannitol, silicon dioxide, microcrystalline cellulose, crospovidone, or magnesium stearate.

9. The method of claim 1, wherein the regimen for treating the hematological disorder further comprises administering a second therapeutic agent.

10. The method of claim 9, wherein the second therapeutic agent is selected from the group consisting of 1-(butyryloxy)ethyl-5-amino-4-oxopentanoate (AN-233); hydroxyurea; N-[4-[4-(cyclopropylmethyl)piperazine-1-carbonyl]phenyl]quinoline-8-sulfonamide (AG348); (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one (FT-4202); 2-hydroxy-6-[[2-(2-propan-2-ylpyrazol-3-yl)pyridin-3-yl]methoxy]benzaldehyde (voxelotor); 4-[3,5-bis(2-hydroxyphenyl)-1,2,4-triazol-1-yl]benzoic acid (deferasirox); 3-hydroxy-1,2-dimethylpyridin-4-one (deferiprone); luspatercept; crizanlizumab; inclacumab; and combinations thereof.

11. The method of claim 9, wherein the first therapeutic agent and the second therapeutic agent are administered sequentially.

12. The method of claim 9, wherein the first therapeutic agent and second therapeutic agent are administered simultaneously.

13. The method of claim 9, wherein the second therapeutic agent further comprises at least one pharmaceutically acceptable excipient.

14. The method of claim 13, wherein the at least one pharmaceutically acceptable excipient comprises mannitol, microcrystalline cellulose, crospovidone, or magnesium stearate.

15. The method of claim 9, wherein the second therapeutic agent is administered as an enteric coated, stomach or gastric acid stable formulation.

16. The method of claim 1, wherein the regimen for treating the hematological disorder comprises administering the first therapeutic agent to the subject once or twice per day.

17. The method of claim 1, wherein the regimen for treating the hematological disorder comprises administering the first therapeutic agent to the subject once, twice, or three times per week.

18. The method of claim 1, wherein the first therapeutic agent is administered in an amount of from about 1.5 mg to about 15 mg.

19. The method of claim 1, wherein the hematological disorder is thalassemia.

20. The method of claim 9, wherein the second therapeutic agent is a gene therapy product.

\* \* \* \* \*